United States Patent [19]

Lau

[11] Patent Number: 5,374,658

[45] Date of Patent: * Dec. 20, 1994

[54] USE OF OXIDIZED POLYAMINES, ESPECIALLY NN'-BIS-(3-PROPIONALDEHYDE)-1-4-DIAMINOBUTANE (SPERMINE DIALDEHYE) IN GRAFT TREATMENT

[75] Inventor: Catherine Y. Lau, Unionville, Canada

[73] Assignee: Ortho Phamaceutical Corporation, Raritan, N.J.

[*] Notice: The portion of the term of this patent subsequent to Dec. 15, 2009 has been disclaimed.

[21] Appl. No.: 85,242

[22] Filed: Jun. 29, 1993

Related U.S. Application Data

[63] Continuation of Ser. No. 931,667, Aug. 19, 1992, abandoned, which is a continuation of Ser. No. 769,129, Sep. 30, 1991, abandoned, which is a continuation-in-part of Ser. No. 586,326, Sep. 18, 1990, Pat. No. 5,171,754, which is a continuation of Ser. No. 262,760, Oct. 26, 1988, abandoned.

[51] Int. Cl.$^5$ ............ A01N 33/08; A61K 31/13; A61K 31/19; A61K 31/20
[52] U.S. Cl. ............ 514/557; 514/558; 514/666
[58] Field of Search ............ 514/557, 558, 666

[56] References Cited

FOREIGN PATENT DOCUMENTS

44646/79 of 1979 Australia .
0366451A2 5/1990 European Pat. Off. .
2908032 of 1979 Germany .
2017492 of 1979 United Kingdom .

OTHER PUBLICATIONS

Wang et al "Ex vivo spermine dialdehyde treatment prevents lethal 6VHD in a murine bone marrow transplantation model" Bone Marrow Transplantation (1990) 6, 235–242.
Gaugas, Polyamines in Biomedical Research (1980) John Wiley & Sons Chapter 22 pp. 343–362.
Br. J. Cancer, vol. 39, No. 5, 1979, pp. 548–557 J. M. Gaugas, et al. "Evidence for serum binding of oxidized spermine . . . ".
Euro. J. Immunology, vol. 11, No. 3, 1981, pp. 266–269, Verlag Chemie. Weinheim, DE R. S. Labib et al. "Enzymatic oxidation . . . ".
Israel. J. Med. Sci., vol. 1, No. 4, 1965, pp. 541–551, U. Bachrach et al. "Antiphage . . . ".
Chemical Abstracts, vol. 75, No. 19, 8th Nov. 1971, p. 190 Abstract No. 117960c Columbus, OH and JP-A-71 24 365 (Takeda Chemical . . . ).
Casero et al., Cancer Research 49, pp. 639–643, Feb. 1, 1989.
Casero et al., Cancer Research 47, pp. 3964–3967, Aug. 1, 1987.
Wang, et al., Bone Marrow Transplantation (1990), vol. 6, pp. 235–242.
Conant et al., Bone Marrow Transplantation–Abstracts–Effect of Spermine Dialdehyde on Ex Vivo Purging of Tumor Cells in Two Autologous Murine Bone Marrow Transplant Models.
Alarcon et al., Archives of Biochemistry and Biophysics 94 (1961).
Tabor et al, "Identificaton of the Aminoaldehydes Produced by the Oxidation of Spermine and Spermidine with Purified Plasma Amine Oxidase", Journal of Biological Chemistry, vol. 239, 2194–2203 (1964).
Fukami et al., Biochemical and Biophysical Research Communications, vol. 28, No. 1, (1967): "Phagocidal Action of Oxidized Spermine and Its Analogues".
K. Kremzner, Leon and Donald H. Harter, Biochemical Pharmacology, vol. 19, pp. 2541–2550, (1969), "An-
(List continued on next page.)

Primary Examiner—Nathan M. Nutter
Attorney, Agent, or Firm—Carmella O'Gorman

[57] ABSTRACT

Described herein is the use of a substantially pure form of an oxidized polyamine, and especially spermine dialdehyde, in the treatment of tissue grafts or other organs for transplantation. The compounds and treatment are especially useful in treating grafts for bone marrow transplants, whether they be allogeneic or autograft transplants.

41 Claims, 18 Drawing Sheets tiviral Activity of Oxidized Polyamines and Aldehydes".

Bachrach, U., and F. Don, Journal of General Virology, vol. 11, (1) 1-9: (1971): "Inactivation of Myxoviruses by Oxidized Polymines".

Kimes, Brian and David R. Morris, Biochimica et Biophysica Acta, vol. 228 (1971), pp. 223-234 (1970): "Preparation and Stability of Oxidized Polymines".

Bachrach, U. and E. Rosenkovitch, Applied Microbiology, vol. 23, No. 2, (1972) pp. 232-235: "Effective Oxidized Spermine and Other Aldehydes on the Infectivity of Vaccina Virus".

Byrd et al., Nature vol. 267, (1977) pp. 621-623: "Synthetic Polyamines Added to Cultures Containing Bovine Sera Reversibly Inhibit In Vitro Parameters of Immunity".

Allen et al., Nature vol. 267 (1967) pp. 623-625: "Identification of a Thymic Inhibitor (Chalone) of Lymphocyte Transformation as a Spermine Complex".

Bachrach et al., Advances in Polyamine Research vol. 3, Edited by C. M. Caldarera et al., Raven Press, New York, 1981: "Polyamine Biosynthesis and Metabolism in Transformed Human Lymphocytes".

Abbott, A. C. and C. C. Bird, vol. 115, No. 2, (1983), pp. 727-742, Biochemical and Biophysical Research Communications: "Cytolethal Sensitivity of Human Lymphoid Cells to Glucocorticoids and Oxidized Polyamines".

Labib, R. and Thomas B. Tomasi, European Journal of Immunology vol. 11, pp. 266-269 (1981): "Enzymatic Oxidation of Polyamines. Relationship to Immunosuppressive Properties".

Frolik, et al., Archives of Biochemistry and Biophysics, vol. 230, No. 1, April, pp. 93-102 (1984): "Inhibition of Transforming Growth Factor-Induced Cell Growth and Soft Agar by Oxidized Polyamines".

Smith, et al., Biochemical Society Transactions, pp. 326-329, vol. 13; "Inhibition of Cell Proliferation by Polyamines Does Not Depend on the Cytotoxicity of Acrolein".

A. Ferrante, Immunology, vol. 54, pp. 785-789, (1985): "Inhibition of Human Neutrophil Locomotion by the Polyamine Oxidase-Polyamine System".

Israel et al., vol. 16, No. 1, (1973): "Synthesis and Anti-Tumor Evaluation of the Presumed Cytotoxic Metabolytes of Spermine and N,N'-bis (3-amino propyl) Nonane-1,9-diamene".

GB patent application GB 2017492.

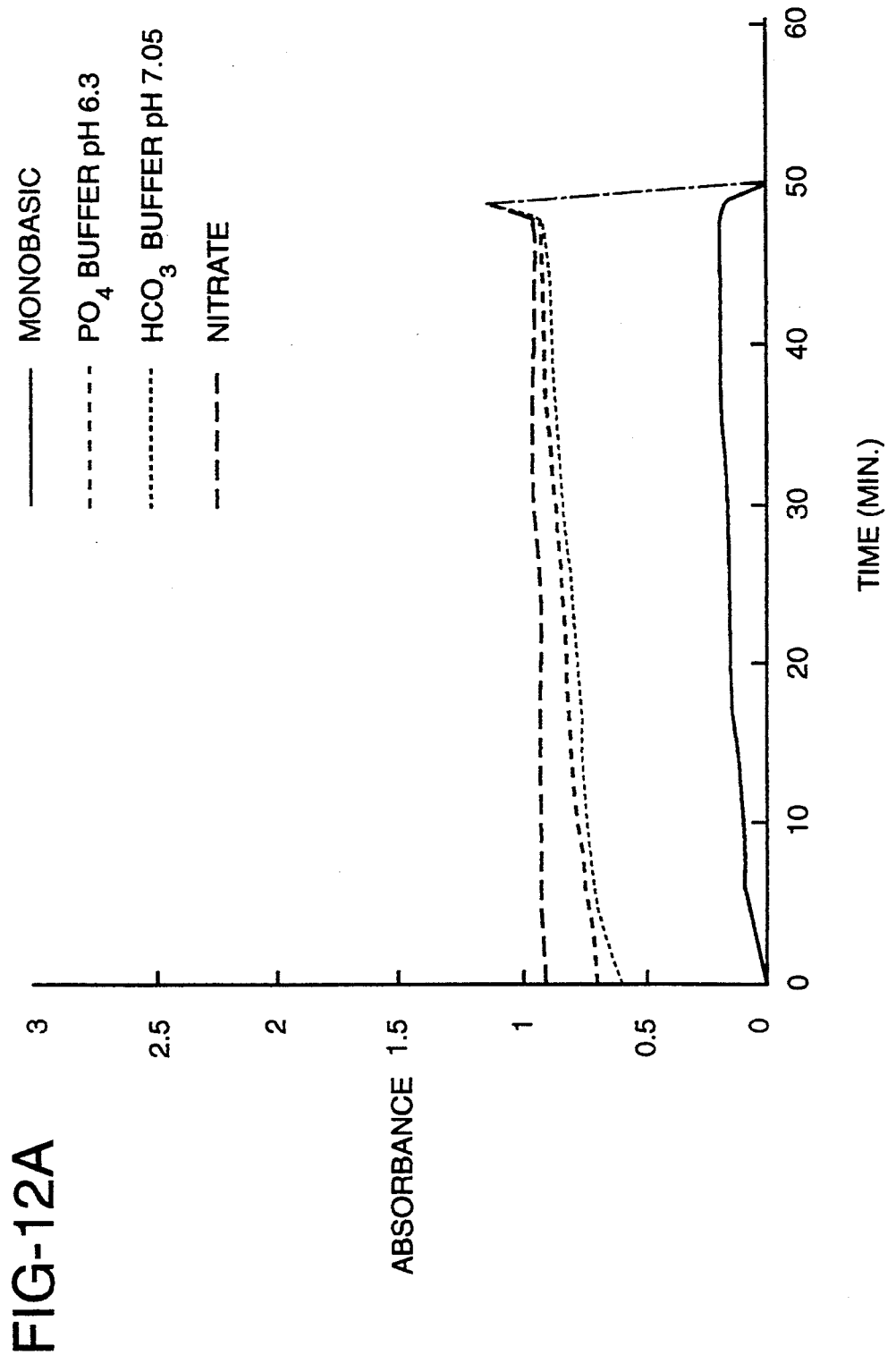

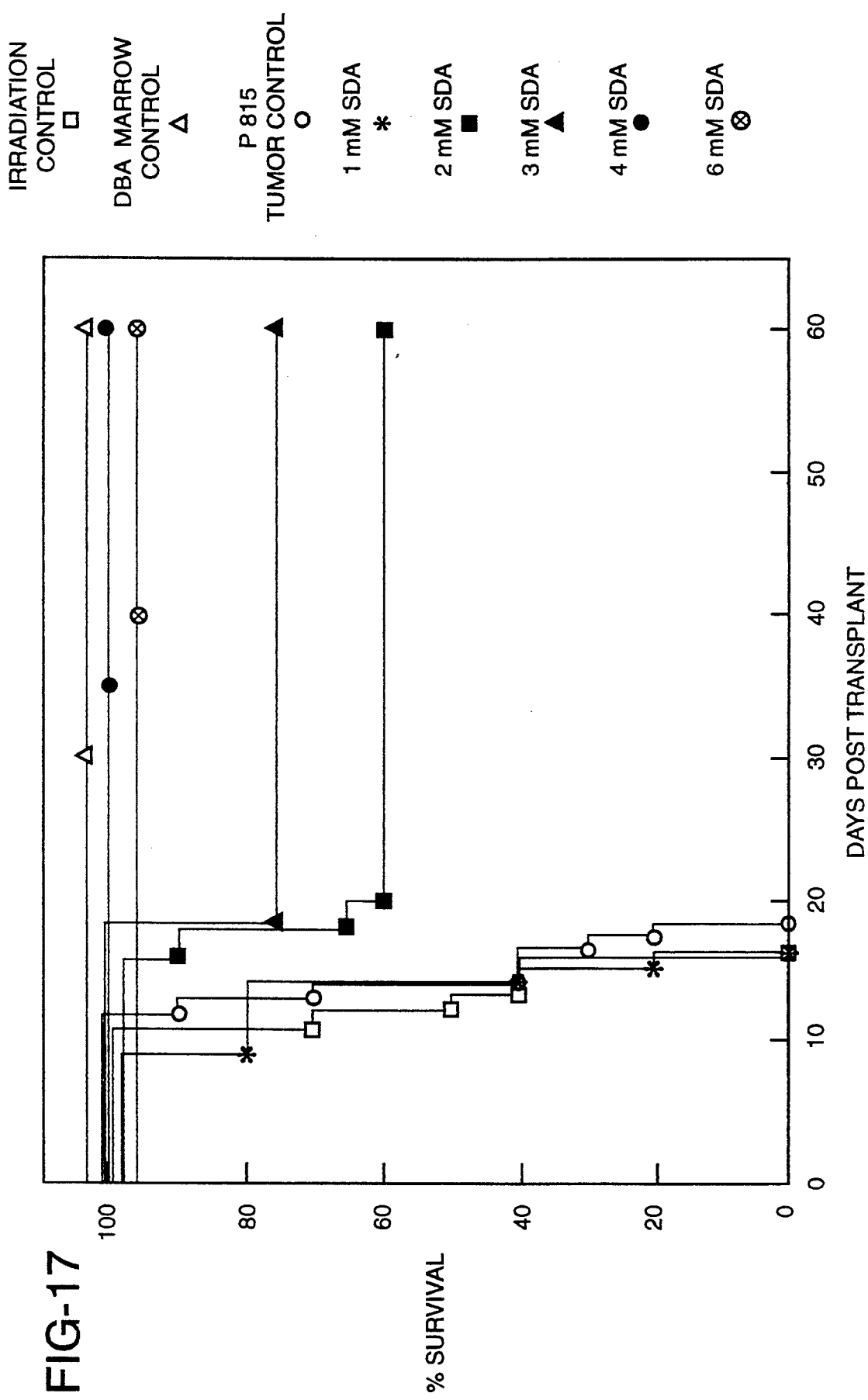

USE OF OXIDIZED POLYAMINES, ESPECIALLY NN'-BIS-(3-PROPIONALDEHYDE)-1-4-DIAMINOBUTANE (SPERMINE DIALDEHYE) IN GRAFT TREATMENT

This is a continuation of application Ser. No. 931,667, filed Aug. 19, 1992, abandoned, which is a continuation of application Ser. No. 769,129 filed Sep. 30, 1991, abandoned, which is a continuation-in-part of application Ser. No. 586,326 filed Sep. 18, 1990, now U.S. Pat. No. 5,171,759, which is a continuation of application Ser. No. 262,760 filed Oct. 26, 1988, abandoned.

FIELD OF THE INVENTION

This invention relates to the use of oxidized polyamines, and especially aminoaldehydes such as N,N'-Bis-(3-propionaldehyde)-1,4-diaminobutane (spermine bisaldehyde) in tissue or other organ transplantation treatment.

BACKGROUND OF THE INVENTION

The transplantation of tissues or other organs from a healthy donor to a recipient who has suffered irreparable damage or disease, has its origins in ancient medical history. Organ and tissue allo-transplantation, though artificial, is the short-term solution and long-term cure for maintenance of functional and disease-related failure of select organ systems. Kidney, heart, liver, cornea, and bone-marrow transplants are commonplace; steady progress in skin, pancreas and lung transplantation is evident.

Conventional immunosuppression is used to prevent or ameliorate allograft rejection; it is an anti-proliferative and anti-differentiation chemotherapy designed to disarm the immune system.

Many immunosuppressive drugs in use today were initially applied as therapy for cancer; they are highly toxic to dividing cells. Blanket immunosuppression, however, is dangerous, especially for cells residing in bone marrow and the small intestine. Opportunistic infections by cytomegalovirus and herpesvirus, by various fungi, mycobacteria and by protozoans, are also a problem; increased risk of neoplasia is a suspected result of prolonged immunosuppression.

When tissue is transplanted from one location to another within or on the same individual, the prefix "auto-" is used. Thus, as used herein, the term "autologous" or "autogeneic" refers to those tissue graft situations wherein the donor and recipient are the same individual. The donor tissue is genetically identical to that of the recipient since they are one and the same. As used herein, the term "allograft" or "allogeneic" refer to those tissue graft situations wherein the donor and recipient are genetically different individuals within one species.

Bone marrow transplant has been the treatment of choice in a variety of diseases such as breast cancer, Hodkin's disease, non-Hodkin's lymphoma, and especially certain leukemias, and immunodeficiency disorders. There are several deleterious phenomena associated with bone marrow transplantation. Incidences of bone marrow graft rejection and/or leukemic relapse are quite common. Bone marrow transplantation is also notable because the recipient may be immunoincompetent, but the bone marrow graft often contains immunocompetent cells. This arrangement can lead to yet another phenomenon deleterious to successful tissue engraftment, and that is graft-versus-host reactions.

For example, allogeneic bone marrow transplantation (BMT) has demonstrated clinical efficacy for the treatment of refractory leukemia and genetic hematological disorders. However, a major barrier to successful allogeneic transplant has been this development of severe, and sometimes fatal, post-transplantation graft vs. host disease (GVHD). Recent advances in immunosuppressive therapies for GVHD prophylaxis have demonstrated tremendous success in reducing GVHD after HLA-identical transplants. However, for HLA-nonidentical transplants, in addition to conventional immunosuppressive regimens, it is generally recognized that some form of ex vivo T cell depletion is essential to keep GVHD under control. Methods employed for T cell depletion include, inter alia, the utilization of monoclonal antibodies against T cell surface antigens together with complement to trigger selective cytolysis, antibody-coated magnetic beads, elutriation and physical separation by soya bean agglutinin. These procedures, despite being very effective in T cell depletion, are usually time consuming, labor intensive and occasionally result in low cell recovery.

Further, while several clinical trials indicate that both the incidence and severity of GVHD in engrafted patients are reduced if bone marrow is depleted of donor T-lymphocytes, there has been an increased incidence of graft rejection and leukemic relapses in these patients. It has recently been shown that the use of antibodies against selected T cell subsets or partial instead of complete T cell depletion appear to yield better results, at least in terms of graft rejection.

Secondly, during autologous bone marrow transplantation (ABMT), patients' bone marrow samples, though harvested during remission, usually still contain a small percentage of leukemic cells which give rise to a high rate of post transplantation relapses. However, if the marrow is purged free of leukemic cells with selective o reagents that exert minimum impact on marrow progenitors that are required to reconstitute the hemopoietic system of the patient, the chance of relapses will be much lower.

The reagent that is currently used by many centers to purge the leukemic contamination in bone marrow preparations is an activated form of cyclophosphamide, 4HC (4-hydroperoxy-cyclophosphamide). This reagent is very effective in removing leukemic cells (average $D_{10}$ for leukemic cells is about 30 ug, wherein $D_{10}$ is defined as 1 log of depletion) but is also quite toxic to marrow cells ($D_{10}$ is about 50 ug) and the therapeutic window is relatively small (therapeutic index $\approx 1.67$).

Polyamines such as sperminc, spermidine and putrescine are widely distributed in mammalian cells, although they are found to differ in their relative concentrations. The literature is replete with reports of these compounds or certain of their metabolites, possibly being involved in biological activity such as immunosuppression activity and other inhibiting activity. For example, oxidized polyamines are believed to inhibit growth of parasites (D. M. L. Morgan and J. R. Christensen, Adv. Polyamine Res., 4, 169–174 (1983); D. M. L. Morgan, U. Bachrach, Y. G. Assaraf, E. Harari and J. Golenser, Blochem. J., 236, 97–101 (1986)), suppress infectivity of selected strains of phage and bacteria (U. Bachrach, S. Don and H. Wiener, J. Gen. Virol., 13(Pt. 3), 415–22 (1971); K. Nishimura, T. Komano and H. Yamada, Blochim. Biophys. Acta, 247(1), 153–6 (1971)

J. G. Hirsch and R. J. Dubos, J. Exp. Med., 95, 919 (1952); C. W. Tabor and S. M. Rosenthal, J. Pharmacol., 116, 139 (1956)) and inactivate several strains of viruses (U. Bachrach and E. Rosenkovitch, Appl. Microbiol., 23(2), 232–5 (1972); U. Bachrach and S. Don, J. Gen. Virol., 11(Pt. 1), 1–9 (1971); U. Bachrach, C. W. Tabor and H. Tabor, Biochem. Biophys. Acta, 78, 768 (1963); U. Bachrach and J. Leibovici, Isr. J. Med. Sci., 1,541 (1965); J. Schindler, Experientia, 21,697 (1965); E. Katz, T. Goldblum, U. Bachrach and N. Goldblum, Isr. J. Med. Sci., 3,575 (1967)). The literature does not make clear however, whether the inhibitory effect is due to aminoaldehydes or other toxic side products such as hydrogen peroxide and ammonia released during the oxidation of spermine by PAO.

Hence, despite the impressive list of studies performed with oxidized spermine, the actual molecular structure(s) mediating the specific immunosuppressive or inhibitory activities is unknown. Oxidation of spermine by PAO revealed six major oxidation products in addition to ammonia and hydrogen peroxide (R. S. Labib and T. B. Tomasi, Jr., Eur. J. Immunol., 11,266–269 (1981)). The inhibitory effect of each of the products has not been analyzed but it was believed that the dioxidized sperminc or sperrnine dialdehyde (NN'-Bis-(3-propionaldehyde) -1-4-diaminobutane) would demonstrate activity. Israel et al, (Supra) (1973), synthesized this molecule together with another analogue and found that both compounds exhibited cell inhibitory activities in vitro. These investigations however failed to find significant in vivo efficacy with the dialdehydes they synthesized. Furthermore, these molecules were quite toxic, sperminc dialdehyde (NN'-Bis-(3-propionaldehyde)-1-4-diaminobutane) showed severe acute toxicity with an $LD_{100}$ at 40 mg/kg when given intraperitoneally.

Splenic cells were treated with various concentrations of SDA or an analogue for 30 min. at 37° C. Cells were washed and cultured in the presence of Concanavalin A for 3 days. [$^3$H] Thymidine 0.1 $\mu$Ci/well was added and cells were harvested after 18–24 hrs. SDA was the most potent antiproliferation drug, with an $IC_{50}$ of 0.70 $\mu$M. Although butyl dialdehyde was 30 fold less potent than SDA, it should be metabolically more stable and hence clinically relevant.

Figure 9:
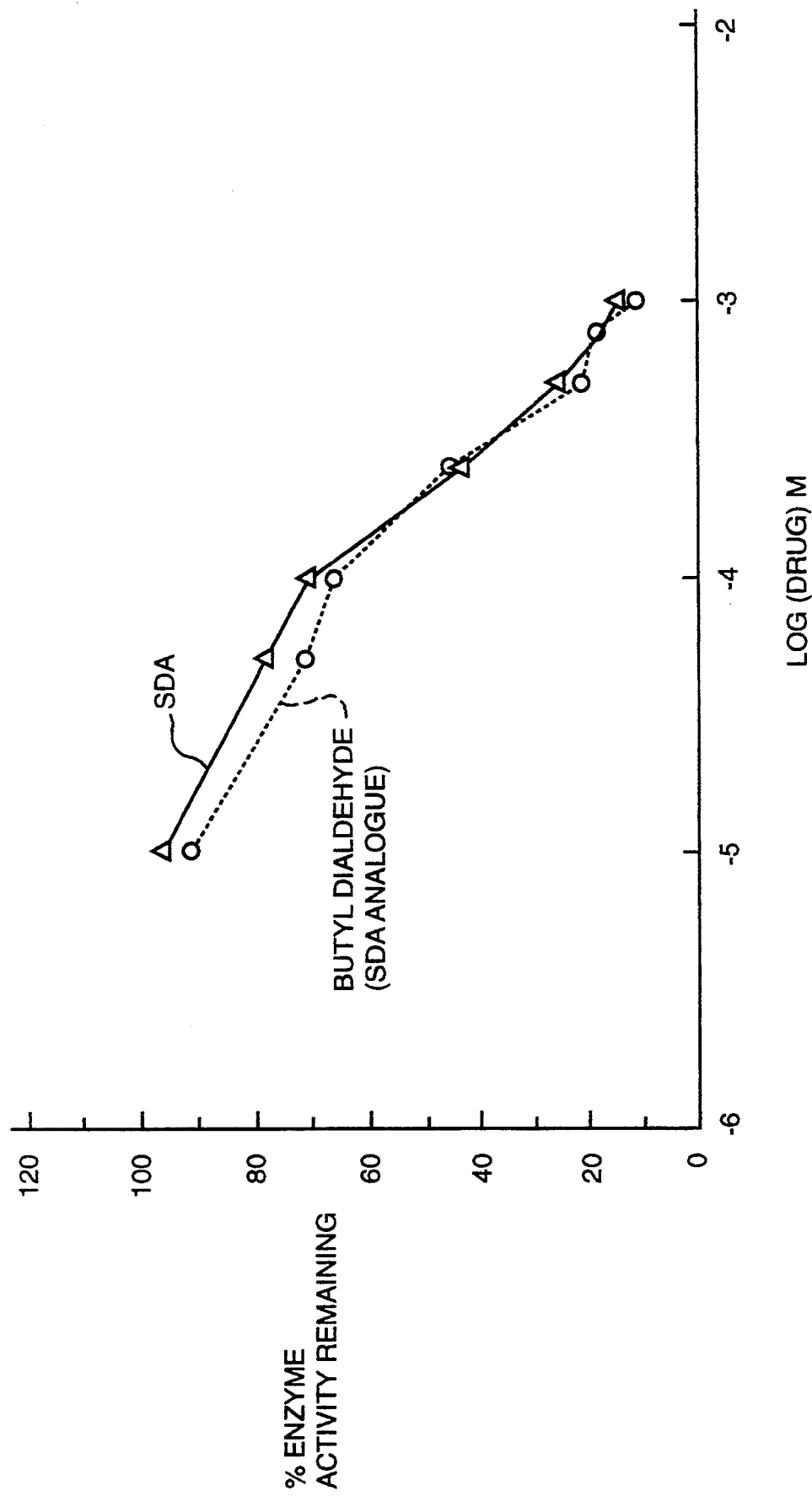

FIG. 9 Inhibition of S-Adenosylmethionine Decarboxylase (AdoMet DC) by SDA and its Analogue.

Murine leukemic L1210 cell supernatants were incubated with different concentrations of SDA or butyl dialdehyde, and AdoMet DC activity was estimated by monitoring the release of [$^{14}$C] $CO_2$. Inhibition curves for both drugs were superimposable with $IC_{50}$ values of $0.12$–$0.13 \times 10^{-3}$M.

Figure 10:
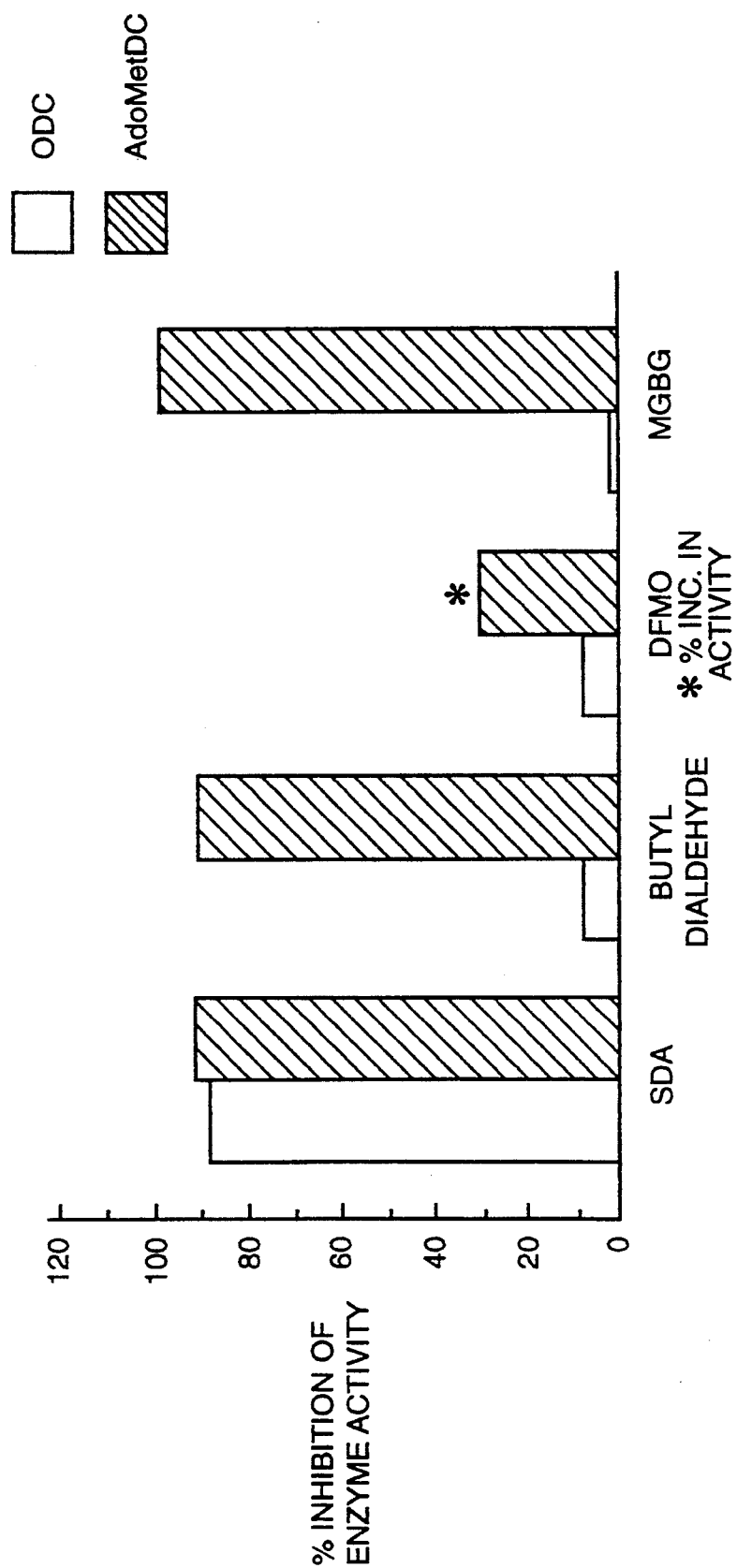

FIG. 10 Regulation of polyamine biosynthetic enzymes by SDA and other known inhibitors. The figure illustrates the comparative profile of the inhibition of key regulatory enzymes of polyamine synthesis by SDA, its analogue, butyl dialdehyde (BDA), difluoromethyl ornithine (DFMO) and methyl glyoxal bis (guanylhydrazone) (MGBG). DFMO inhibited ODC with high potency, while MGBG selectively reduced AdoMet IC activity. The analogue SDA was similar to MGBG in its selectivity to AdoMet DC. However, SDA was the only drug that inhibited both of the key enzymes, thereby eliminating the compensatory response (of DFMO on AdoMet DC) and ensuring complete inhibition of polyamine biosynthesis.

Figure 11:
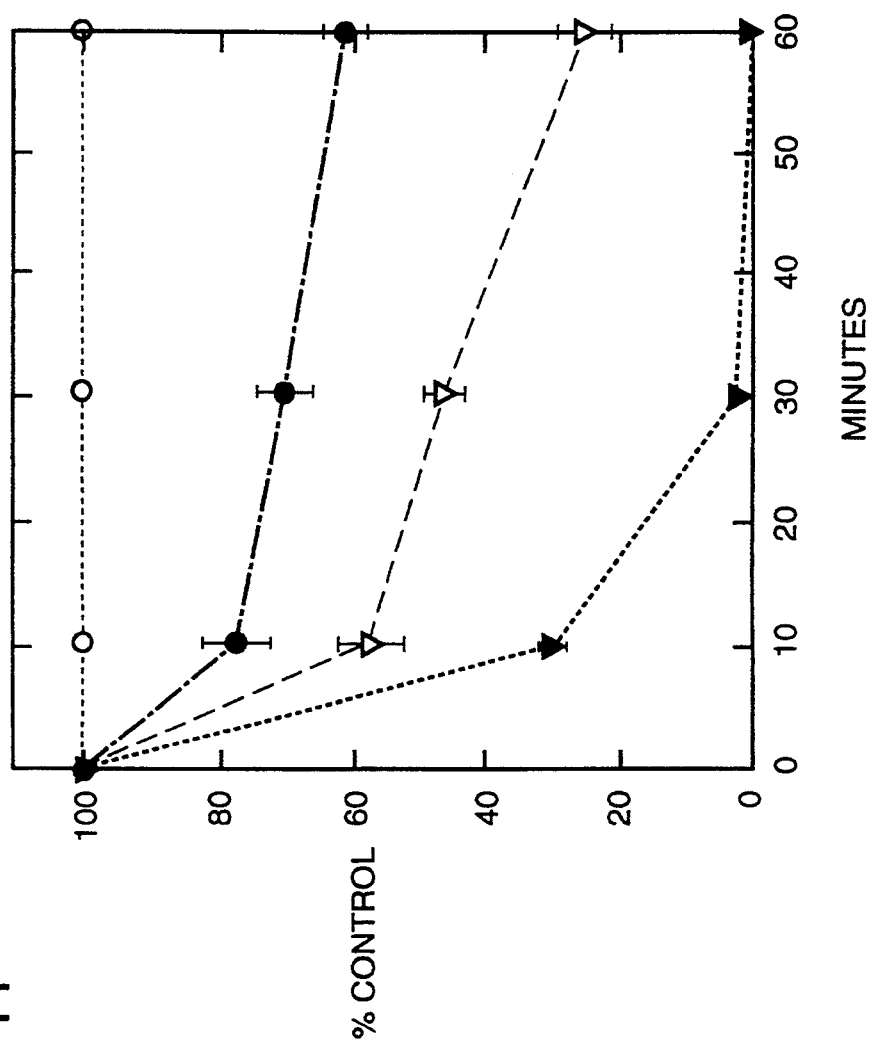

FIG. 11 Stability of SDA in various buffers. Saline (○), modified PBS (●), PBS (▽) and RPMI (▼). SDA (stock solution 20 mM in saline) was diluted to 1 mM in buffers indicated in the figure and incubated at 37° C. At different times after incubation, samples were removed and the DNP derivative was made and loaded onto a reverse phase column. The molar concentration was calculated by comparing to the reference standard.

$$\% \text{ control} = \frac{\text{molar concentration of SDA at different times}}{\text{molar concentration at time zero}}$$

Results represent the mean and standard deviation of replicate runs.

Figure 12B:
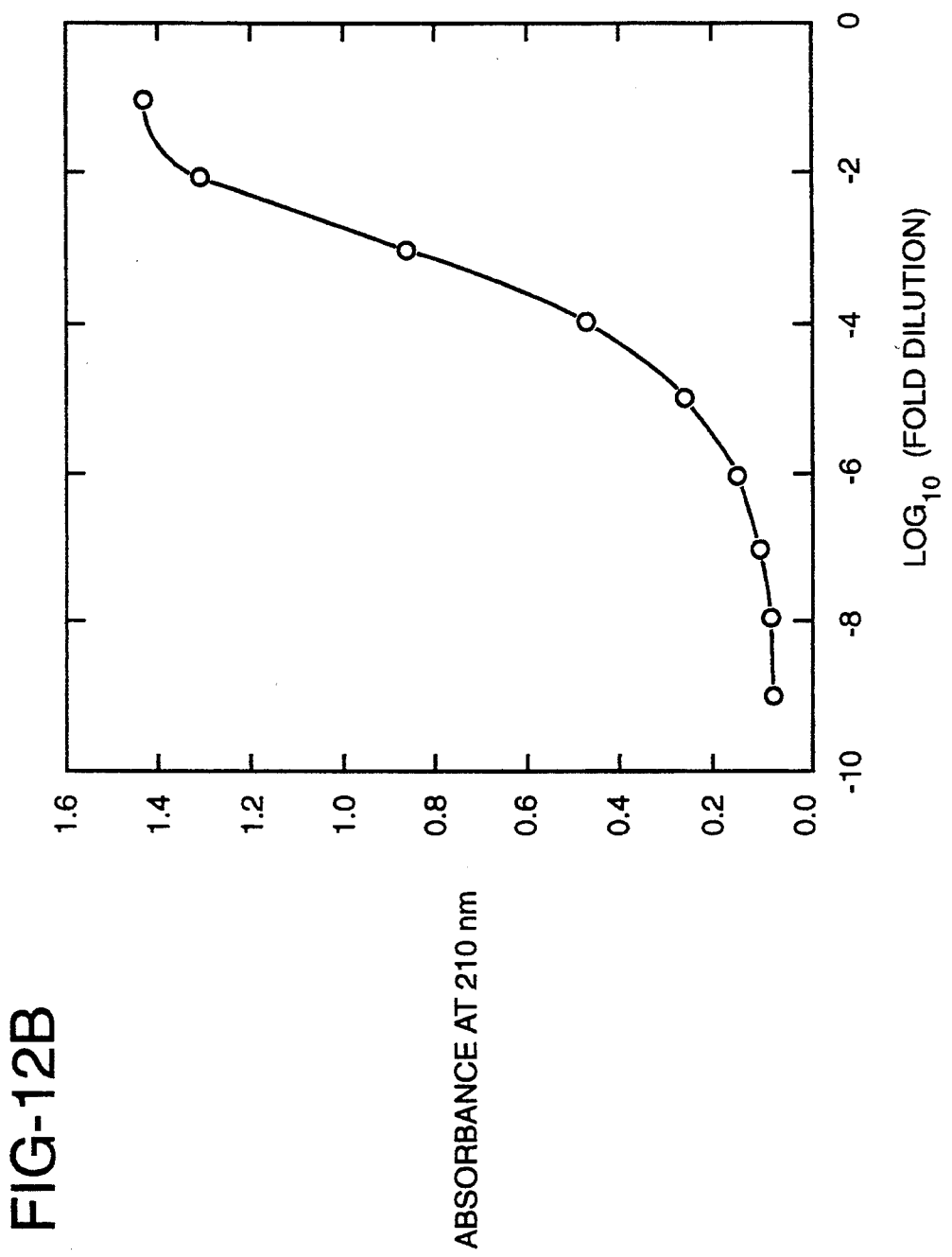

FIG. 12 Measuring the release of acrolein from SDA. SDA at 20 mM was diluted into buffers indicated in the figure until the final concentration was 1 mM. Different preparations were put into cuvettes and absorbance was read at 210 mM in a Gilford Model spectrophotometer equipped with a Haake constant temperature circulator. Insert shows absorbance spectrum of authentic acrolein at 210 mM. Phosphate bicarbonate and nitrate buffers showed high background absorption in these studies.

Figure 13:
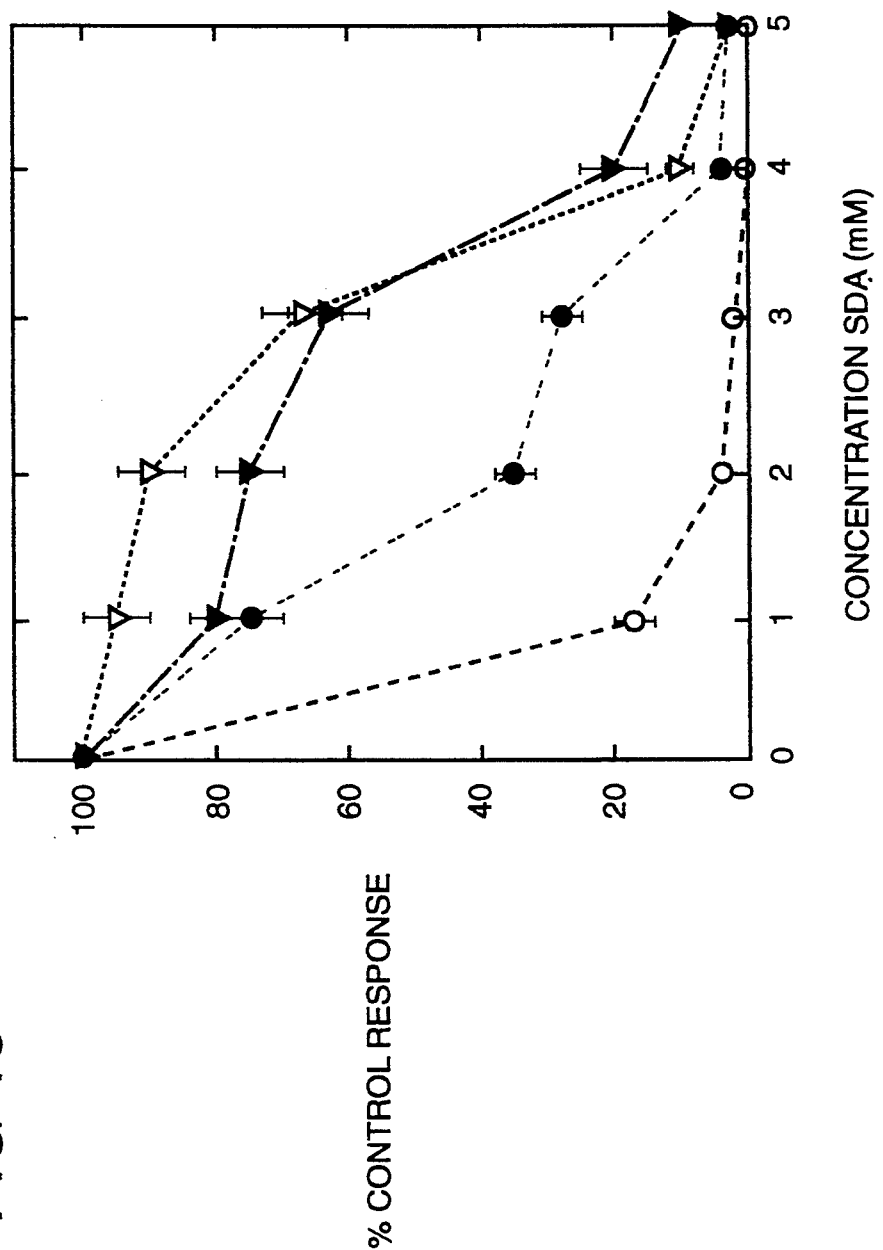

FIG. 13 Effect of SDA on T cell proliferation and myeloid colony growth after incubation in different buffers: T cell in PBS (◯)), myeloid in PBS (●), T cell in saline (▽), myeloid in saline (▼). Spleen cell and bone marrow cell mixture from Balb/c mice were incubated in the presence of saline (30 min) or PBS (10 min) as described in Materials and Methods. T cell proliferation was assayed by Con A induced stimulation and myeloid growth was assayed by methylcellulose culture. The mean cpm for $^3$H-thymidine uptake into stimulated T cells was 55,765 in the control group and the mean total CFU's in control culture was 256.

$$\% \text{ control response} = \frac{\text{cpm or total CFU's in different SDA treated samples}}{\text{cpm or total CFU's in control samples}}$$

Data represents mean of triplicate cultures and 2 additional experiments show similar results.

Figure 14:
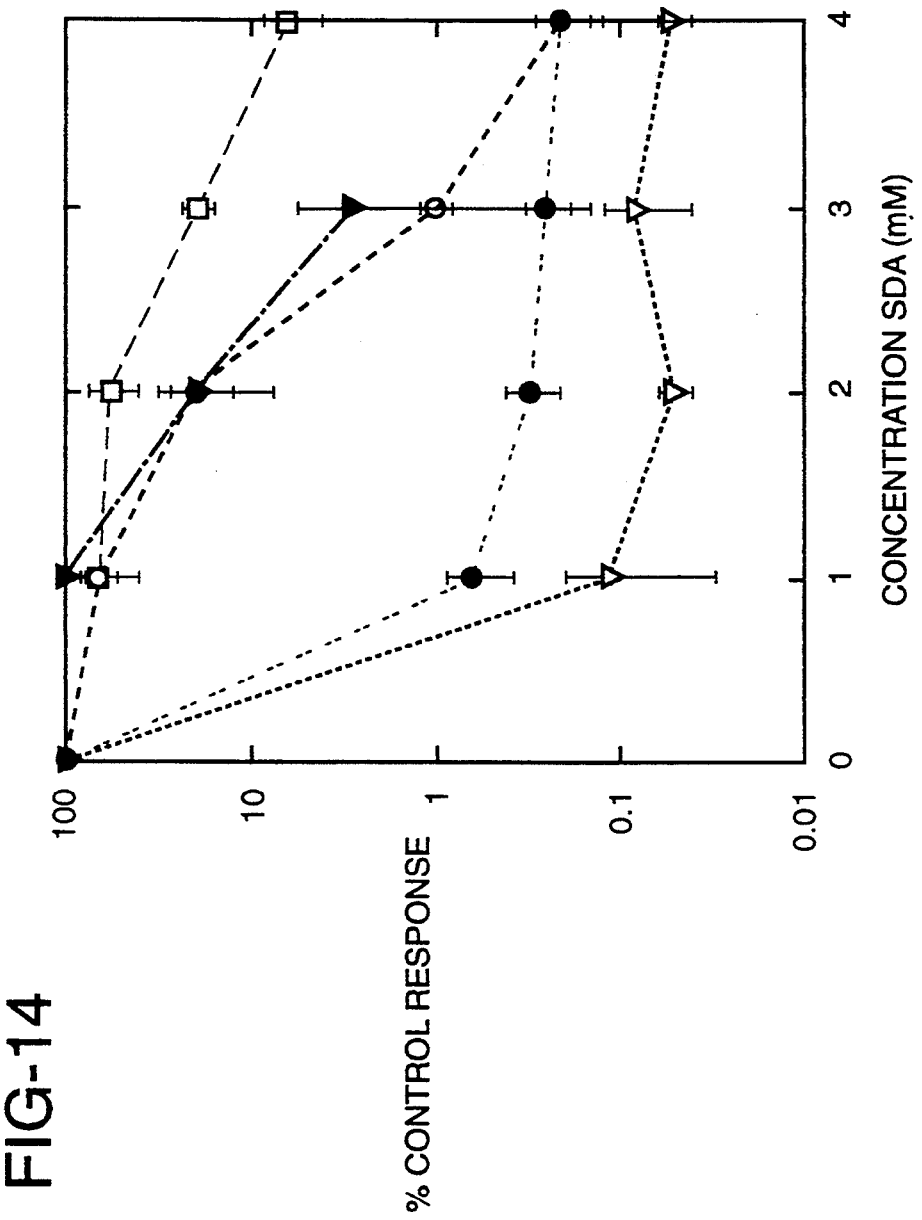

FIG. 14 The inhibitory effect of SDA on the murine tumor cell lines, L1210 leukemia (◯), YAC-1 lymphoma (▽), P815 mastocytoma (●), V/EHI-164 fibrosarcoma (▼) and normal murine myeloid CFU (□). Data points represent the mean ±SD of percent control response of treated cells compared to untreated controls in 3-5 experiments. Tumor proliferation results are based on $^3$H-thymidine incorporation 3 days following drug treatment and myeloid results are based on % recovery of BFU-E, CFU-6M and GEM in a methylcellulose containing clonogenic assay.

Figure 15:
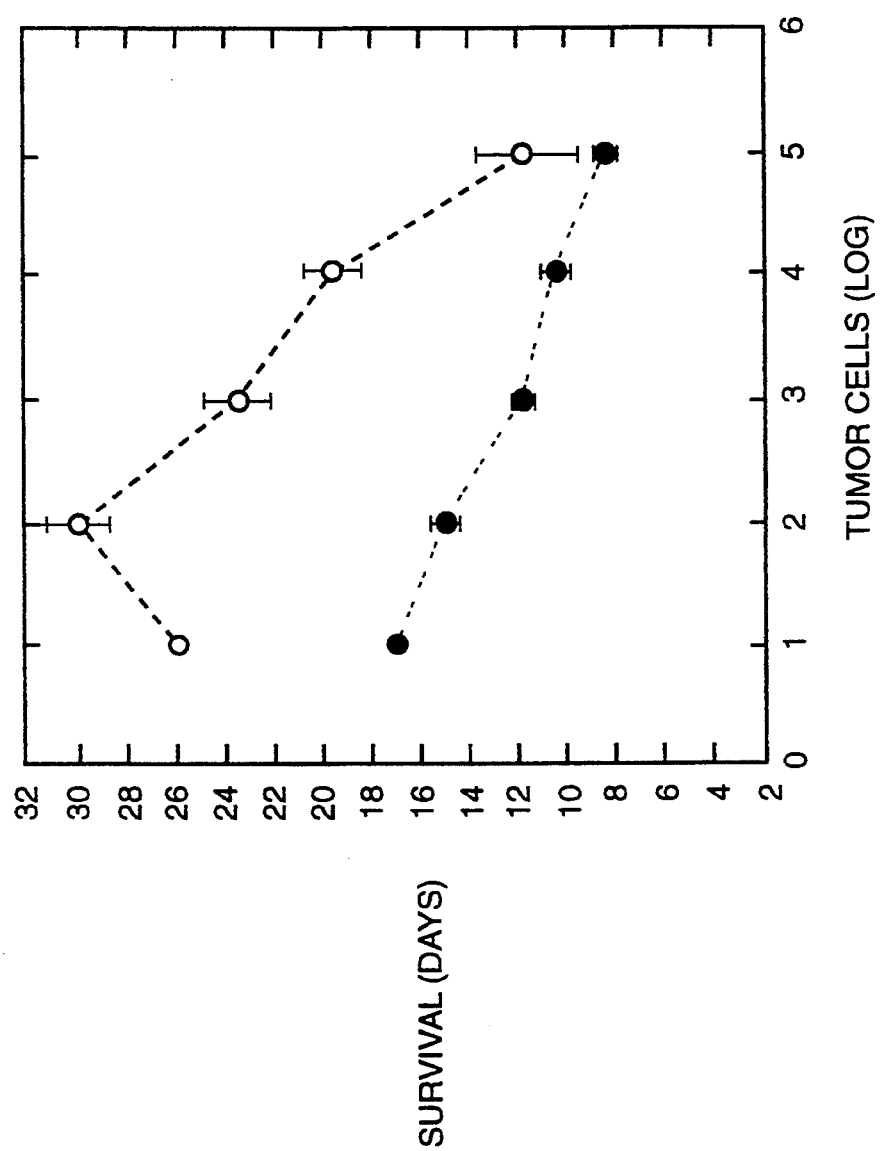

FIG. 15 Tumorigenicity of murine tumor cell lines. Lethally irradiated syngeneic mice (n=5) received intravenous injections of $10^6$ bone marrow cells mixed with varying numbers (log 10) of L1210 leukemia (◯) or P815 mastocytoma cells (●). Those groups receiving $10^2$ to $10^5$ tumor cells presented 100% death rate in a dose response manner, whereas 80% (i.e. 4/5) mice infused with 10 tumor cells became long term survivors (>60 days). Data showed the mean of the ±SD days of survivors.

Figure 16:
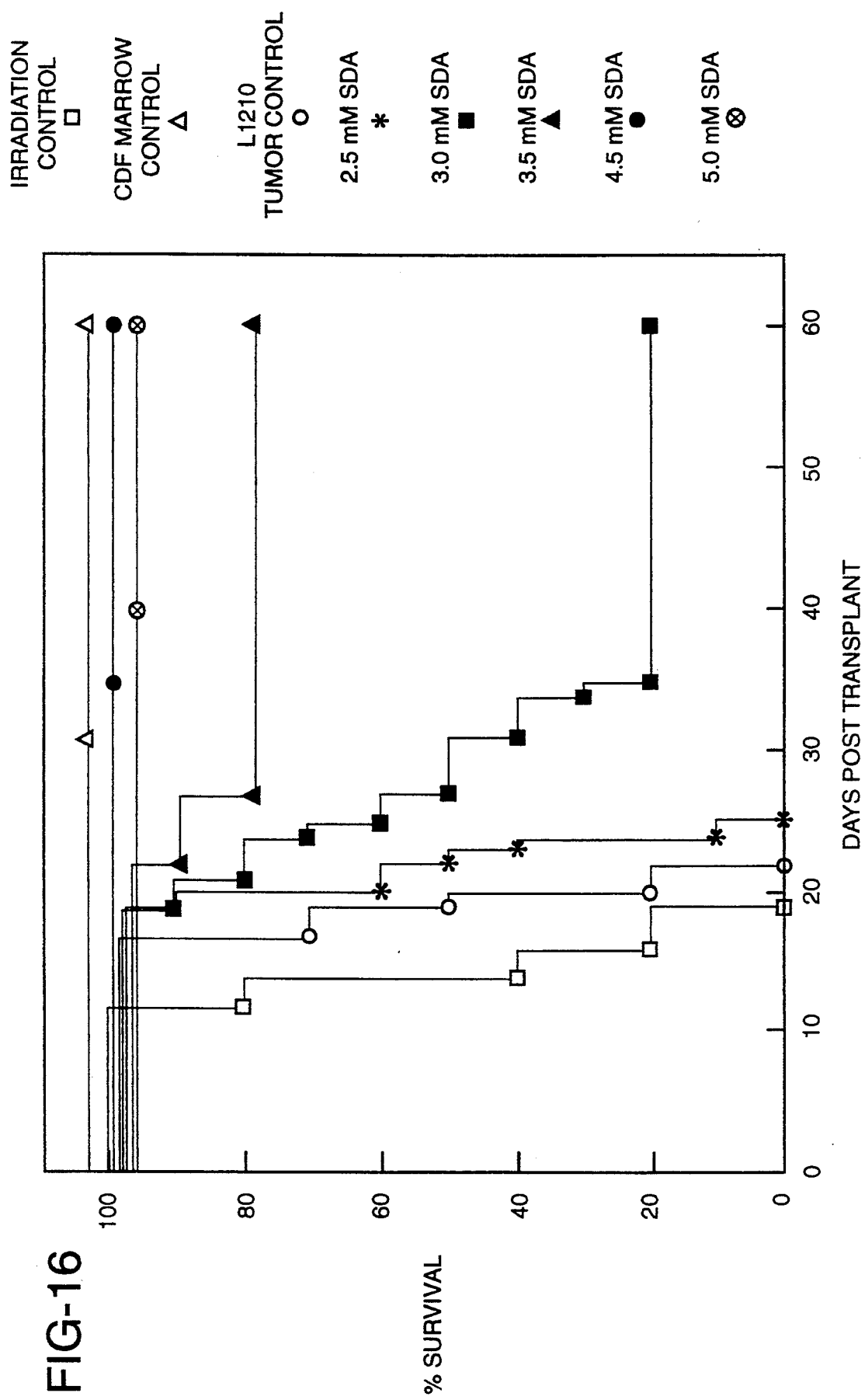

FIG. 16 Survival curve of lethally irradiated CDF, mice receiving syngeneic bone marrow cells mixed with L1210 tumor cells with and without SDA pretreatment. Animals in the irradiation control group (□) received no cells. Animals in the marrow control group were infused with vehicle treated CDF marrow cells only (▽). The tumor control group received vehicle treated L1210 bone marrow cell mixture (◯) and the remaining groups received tumor marrow mixture treated ex vivo with 2.5 mM (*), 3.0 mM (■), 3.5 mM (▲), 4.5 mM (●) and 5.0 mM (⊗) SDA (n=10 for each group).

FIG. 17 Survival curve of lethally irradiated DBA mice receiving syngeneic bone marrow cells mixed with P815 tumor with and without SDA pretreatment. Animals in the irradiation control group received no cells (□), while those in the marrow control group received vehicle treated DBA maxrow cells only (▽). The tumor control group was infused with vehicle treated P815 tumor marrow cell mixture (◯), and remaining groups received tumor marrow mixture treated ex vivo with 1 mM (*), 2 mM (■), 3 mM (▲), 4 mM (●) and 6 mM (⊗) SDA (n=10 for control groups and n=20 for treated groups).

SUMMARY OF THE INVENTION

The present invention provides a method for selective suppression of subpopulations of deleterious cells within a tissue or other organ graft population of cells, which comprises administering to said graff population of cells, in substantially pure form, a compound having the formula:

in an amount, and for a period of time suitable to suppress phenomena deleterious to graft transplantation, without substantial suppression of other cells within said graft population of cells, said other cells capable of facilitating tissue or organ engraftment.

This immunosuppressive response is particularly selective for the suppression of the function and/or proliferation of lymphoid cell populations, especially the natural killer population, helper T cell and cytotoxic T cell subpopulations.

Also provided are methods for inducing a suppressive response in a living organism which comprises the administration of a compound having the above formula to said organism, in substantially pure form and in an amount effective to induce said response.

The methods as described herein are particularly suitable in the therapeutic control of various immunologically-related disease states such as tissue or other organ graft rejections, graft vs. host rejections, delayed hypersensitivity and the like, especially in bone marrow transplantation situations. In the preferred embodiments, the compound of the invention could be used as an effective prodrug for both allogeneic and autologous bone maxrow transplantation procedures, and enhance the tissue engraftment and the overall clinical success of each type.

The compounds as used herein suppress the proliferation or the particular function of cells that are deleterious to successful engraftment, including T cells, NK cells, and residual leukemia cells, while sparing those cells, such as myeloid cells, required for successful graft acceptance and cellular hematological/immunological reconstitution. Other cells, such as mature red blood cells may also be spared or even added during the transplant procedure to facilitate the successful grafting process. The incubation procedure in the treatment as presented herein is operationally more simple than monoclonal antibody depletion methods currently known to the art or other available therapeutic regimes. Further, the present compounds offer a much wider safety margin than many of the therapeutic regimes currently available.

DETAILED DESCRIPTION OF THE INVENTION

The present inventors have discovered that compounds, particularly those obtained by synthetic methods, having the General Formula:

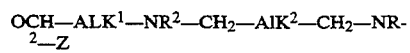

wherein

ALK$^1$ is independently alkylene;

R$^2$ is independently hydrogen or —CH$_2$R$^3$;

R³ is independently alkyl;
ALK² is alkylene;
Z is H or ALK¹—CHO;
or the acid addition salt thereof.

[General Formula I]

are useful in facilitating the success of tissue or other organ transplantation procedures when applied to a population of graft cells in substantially pure form. Particularly useful are compounds of General Formula I wherein ALK¹ALK², and R³ are each independently straight or branched chain alkylene of about 1 to about 8 carbons, preferably about 1 to about 6 carbons, more preferably about 1 to 4 carbon atoms, and most preferably about 1 to about 2 carbon atoms. In more preferred embodiments, R² is hydrogen. In the particularly preferred embodiments, Z is ALK¹—CHO₁, R² is hydrogen, and ALK¹ and ALK² are each independently about 1 to about 6 carbon atoms, preferably about 1 to about 4 carbon atoms, most preferably about 1 to about 2 carbon atoms. Of the most preferred compounds for use herein may be mentioned sperminc dialdehyde.

The presently described compounds are also useful in the therapeutic inducement of a suppressive response in a living organism. In particular, one of the compounds, synthetic sperminc dialdehyde, used according to the present invention has demonstrated enhanced efficacy and a substantially reduced toxicity [not lethal up to 400 mg/kg, contrary to what was reported in the literature (LD₁₀₀ 40 mg/kg, Israel (1973) Supra)]. The use of these molecules, particularly sperminc dialdehyde, both in in vitro applications as well as in vivo applications, to bone marrow cells is therefore described in detail herein.

As used herein, the term "suppressive response" refers to a suppression in the proliferation of cell types originating from hemopoietic stem cells, particularly the lymphoid lineage, and/or the particular functions attributed to such cells, such functions being demonstrated by the cells when they are alone or in combination with other cell types. The use of the compounds as described herein is particularly suitable in the selective suppression of natural killer cells (NK cells—presently understood to be large granular lymphocytes which do not express T-cell markers, such as CD3, but do express a CD16 marker), a T-cell population, particularly the T-cytotoxic subpopulation, and certain leukemia cells, especially those that are residual to a patient's bone marrow, or develope in a transplantation situation. This suppression may also be described as antigen nonspecific, which is exemplified by a 99 % suppression of mitogen-induced T cell proliferation. In some cases, contrary to the art, this selective suppression has been shown to be irreversible.

As used herein, the term "graff" refers to an organ in solid organ transplantation, or any tissue or other population of living cells intended to be taken from a donor, treated in accordance with the method set forth herein, and transplanted into a recipient, even when donor and recipient are the same.

The compounds for use as described herein may be obtained in any convenient manner. The compounds are preferably used in "substantially pure form" which means substantially free of enzymes or other agents that might be present during its formation, and that will interfere with its efficacy or that might increase toxicity. Hence, in its preferred form, the compounds are preferably 95% pure, more preferably 99% pure, and most preferably 100%, as measured by nuclear magnetic resonance, mass spectro analysis, and HPLC. Inert materials may be present in trace amounts.

The compounds may be obtained by enzymatic oxidation of naturally occurring polyamines by techniques known to the art, as long as the product is purified from the enzymes using conventional purification means such as chromatography and the like. Suitable enzymes for use in an enzymatic oxidation process are those effective to bring about the rapid oxidative deamination of the natural polyamine. Illustrative of such enzymes are amine oxidases obtained from ruminant sera such as beef serum, sheep serum, fetal calf serum and the like. Also applicable are oxidases obtained from mouse amniotic fluid, human pregnant sera, and the like.

To avoid interference with contaminants, it is preferred that the compound be synthesized de novo, using organic synthesis techniques such as those described below. In the particularly preferred embodiments, compounds for use herein are amino dialdehydes. The dialdehyde compound is synthesized by conversion of a diacetal in the presence of an acid. Preferred diacetals are represented by Formula:

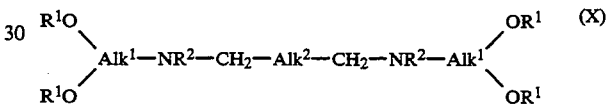

wherein
R¹ is independently alkyl or benzyl
ALk¹ is independently alkylene;
R² is independently hydrogen or —CH₂R³
R³ is independently alkyl; and
ALk² is alkylene.

Preferred reactions may be exemplified by the following schemes:

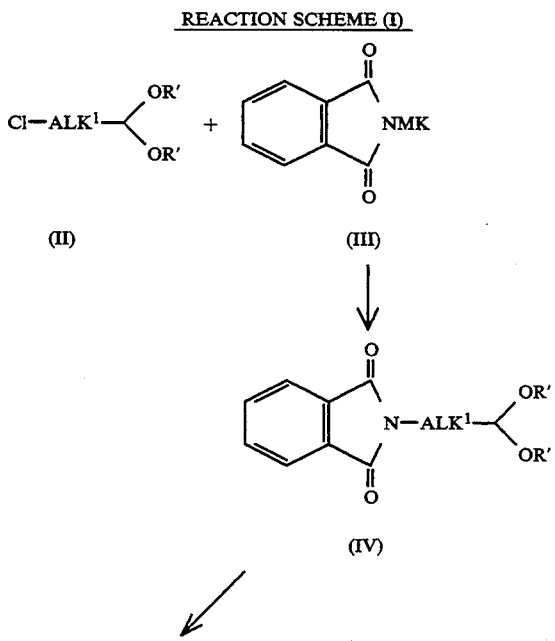

-continued
REACTION SCHEME (I)

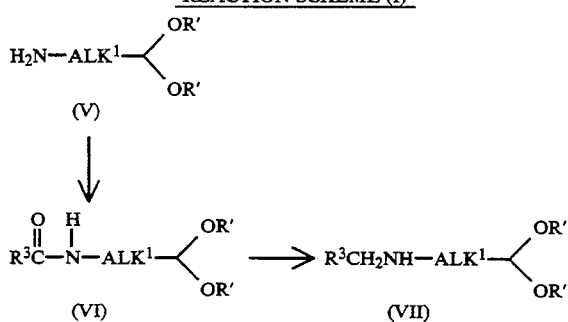

REACTION SCHEME (II)

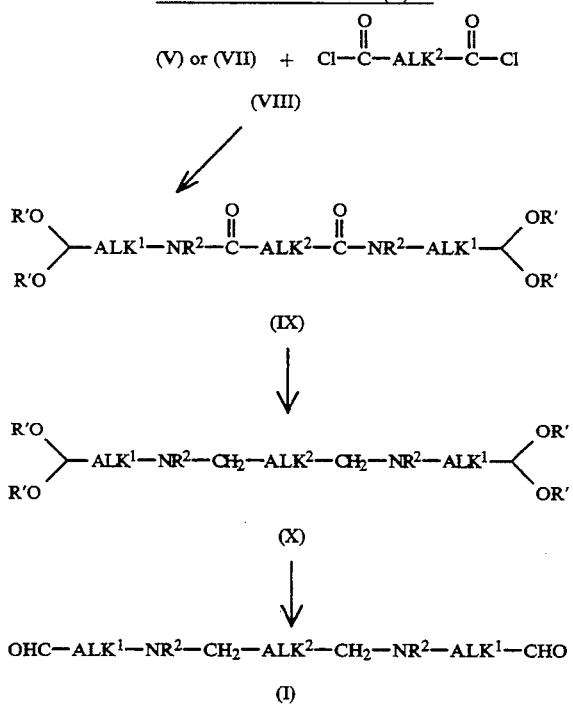

The above reaction Schemes I and II set forth a summary of preferred syntheses for compounds of Formula (X) which may be stored and used to generate compounds of General Formula (i).

A chloroaldehyde of Formula (II) in acetal form is reacted with potassium phthalimide of Formula (III) in equal molar amounts at an elevated temperature to yield the phthalimide of Formula (IV). Examples of the compound of Formula (IF) are 3-ehloroacetaldehyde diethyl acetal and 3-chloro propionaldehyde diethylacetal. The amine is then released by reaction with hydrazinc at an elevated temperature, yielding the primary amine of Formula (V). The primary amine (V) can then be taken on as shown in Reaction Scheme II or can be modified to produce a secondary amine. For the secondary amine, the primary amine of Formula (V) is reacted with an arthydride such as formic-acetic arthydride or acetic anhydride at temperatures that can vary from about 0° C to about room temperatures to yield the amide of Formula (VI). The amide is then reduced with lithium aluminum hydride in tetrahydrofuran at reflux to yield the secondary amine of Formula (VII). In Formulae (II), (IV), (V), (VI), and (VII), $R^1$, $ALK^1$ and $R^3$ are as defined for Formula (X) above.

To prepare the dibenzyl acetal of Formula (V) or (VII) the corresponding diethyl compound may be dissolved in a solvent and reacted with benzyl alcohol in the presence of a small amount of acid such as trichloracetic acid followed by distillation to drive off the ethanol byproduct. For a different alkyl moiety, the diethyl compound may be dissolved in the alcohol, e.g. methanol for the dimethyl acetal, and reacted as in the benzyl case. To avoid cyclization, it may be preferable to subject a compound of Formula II to this treatment, due to the presence of the acid.

In Reaction Scheme II, the primary or secondary amine, designated as compound (V) or (VII), respectively, is reacted with a aliacid chloride of Formula (VIII). Examples of diacid chlorides are succinyl chloride and glutaryl chloride. The reaction is conducted at a low temperature of about −70° to −20° in the presence of a mild base such as triethylamine to yield the diamide of Formula (IX). The diamide (IX) is then reduced with a reducing agent such as lithium aluminum hydride in tetrahydrofuran at reflux to yield the aliamine diacetal of Formula (X). The diamine diacetal (X) can be stored for extended periods and brought to the site of administration to a patient for the conditions described above. After reduction with lithium aluminum hydride, the final product is preferably purified by making the crystalline salt form of the aliamine (X) with an acid. The free amine can then be resynthesized from the salt. However, storage may be easier with the salt form. It should be noted that creation of the salt with acid must be carried out carefully since excessive amounts of the acid will destroy the acetal moieties.

For release of a dialdehyde of General Formula (I), the diacetal (X) would be reacted with an acid such as hydrochloric acid to yield the free dialdehyde. Sodium hydroxide may be used to regenerate (X) from the salt form, if desired.

For a compound of Formula (IX), and thus of (X) and (i), where the two $ALK^1$ moieties are not the same, a single mole of the amine (V) or (VII) is reacted with the anhydride corresponding to the diacid chloride of formula (VIII), e.g. succinic anhydride. The thus-produced mixed carboxylic acid-amide is then reacted with a mole of a different amine of formula (V) or (VII) using a peptide coupling reagent such as (2-ethoxy-1-ethoxycarbonyl-1,2-diahydroquinoline, known as EEDQ, or 1,3-dicyclohexylcarbodiimide, known as DCC, to yield an amide of formula (IX) wherein the two $ALK^1$ moieties are not the same.

One skilled in the art will understand that concentrations of oxidized polyamines suitable for use herein are concentrations effective to induce the desired selective suppression of deleterious cells and/or to suppress phenomena deleterious to successful tissue engrafiment or other transplantation without substantial suppression of those cells capable of facilitating such engraftment, such as myeloid cells, hemopoietic stem cells, and the like. Effective concentrations may vary widely according to the particular cells it is desired to suppress, and the organism from which these cells are obtained. Additional cells may be added to the treatment of the graft to optimize overall tissue engraftment and the reconstitution success. Suitable cells are those that serve to reduce myeloid toxicity while mediating deleterious cell suppression, such as red blood cells, red cell ghosts, serum proteins, and the like. Particularly preferred for use herein is the maintenance in a transplant procedure of a graft tissue hematocrit of 3% to about 10%, with about 5% to about 7% particularly preferred.

The suppressive response induced by the techniques described herein, and the efficacy of the dosing, may also be measured in vitro by methods conventional to the art. This may be accomplished by the incubation of cells to be suppressed with various concentrations of the compound, and comparison of the ensuing proliferation or function of these cell populations with that of control samples that have not been treated with the compound as described herein.

In the method of the invention, the oxidized polyamines are administered to the cells of a graft in any suitable physiologically compatible vehicle such as saline, phosphate buffer saline, methycellulose solutions, and the like. Solutions of the compound or homogeneous dispersions are preferred for such administration. Such solutions or dispersions may also be used to perfuse a solid organ, prior to its transplantation (See Brewer et al., The Lancet, "Effect of Graft Peffusion with Two CD45 Monoclonal Antibodies on Incidence of Kidney Allograft Rejection", Oct. 21, 1989, pp. 935-937, as well as references cited therein for typical perfusion techniques).

SDA in nonionic buffer media is preferred for use in arresting tumor cell growth, such as leukemic cells, while preserving mature T cell proliferation. By "nonionic" is meant a buffer that does not ionize or only ionizes very weakly at neutral pH. Particularly preferred nonionic buffers are saline and triethanolamine, and most particularly saline. Mature T cells may be playing an immunosurveillance role in these instances. Hence, selective suppression of leukemia cells may be a preferred treatment to reduce minimal residual disease in autologous tissue grafts, while preserving normal multipotent progenitor cells in those grafts. This selective suppression may be preferred in the treatment of certain autologous tissue transplantations, especially bone marrow transplantation, to prevent leukemic relapse. Preferred concentrations for SDA in a non-ionic medium range from about 2 mM to about 10 mM, with about 2 mM to about 4 mM particularly preferred. Incubation of a graft with such preferred formulations generally ranges from about 30 minutes to about 60 minutes, with about 30 minutes to about 45 minutes particularly preferred.

SDA used in accordance with the invention may also be a potent inhibitor of T cells and NK cell proliferation and/or function. Preferred for selective suppression of such deleterious cells is SDA in an anionic buffer formulation. By "anionic buffer" is meant a buffer which ionizes readily at neutral pH. Suitable for use herein are those buffer formulations containing one or more compounds selected from the group consisting of phosphates, carbonates, and other compounds that influence the ionic strength of the buffer. Examples of such buffers are serum culture media such as PPMI 1640, αtMEM and TRIS buffer, and the like. For example, ten (10) minutes of incubation at 37° C. in the presence of RPMI 1640, which contains both phosphates and carbonates, could irreversibly inactivate T cells and NK cells as measured by Con A induced proliferation and cytolysis. Preferred anionic buffers are PBS, RPMI 1640, αMEM, and TRIS buffers. Preferred concentrations of the anions in these buffers range from about 0.4 mM to about 2 mM, with about 0.3 mM to about 1 mM particularly preferred.

Thus, in this second preferred embodiment, the cells are allowed to incubate with the compound in a suitable artionic medium such as minimum essential medium (MEMVI), RPMI 1640 and other suitable tissue culture media containing anions. This incubation generally takes place for a period of time sufficient to induce suppression of cell function or proliferation of at least about 25%, and preferably at least about 50%, as compared to control values of cellular growth. The incubation generally ranges for a period of time of about 10 minutes to about 1 hour, preferably about 10 minutes to about 30 minutes. Preferred concentrations of SDA generally range from about 0.01 mM to about 0.2 mM, more preferably about 0.03 mM to about 0.1 mM, and most preferably about 0.03 mM to about 0.06 mM.

Treatment of grafts in accordance with the method of the invention is particularly suitable for ex vivo bone marrow graft treatment for bone marrow transplantation, be it autologous or allogeneic. In the preferred embodiments of the method of the invention, bone marrow extracts are treated ex vivo with sperminc dialdehyde, prior to transplantation of these extracts into a patient. Treatment with the sperminc dialdehyde can inactivate deleterious T lymphocytes, as well as other deleterious cells, without exhibiting toxic effects on the marrow cells themselves, especially the early myeloid progenitor cells in the bone marrow cellular population and red blood cells. This phenomenon has been shown to alleviate typical graft vs. host reactions, which are noted as being lethal to patients undergoing bone marrow transplantations. Suitable treatment parameters for such bone marrow extracts in human subjects may be the ex vivo treatment of cells as described above.

The present inventors have also discovered that direct in vivo administration of the compounds may also be effective to elicit an immunosuppressive response in an organism. For example, it has been discovered that in vivo administration of the compound sperminc dialdehyde can greatly reduce graft vs. host reactions in a living organism. It has further been discovered that administration of this compound will suppress the generation of cytotoxic T cells. It is believed that cytotoxic T cells play a role in the mediation of organ graft rejections, and thus, in vivo suppression of these cells will lead to prolonged graft survival. Hence, it should be appreciated that the in vivo administration of these compounds has far-reaching therapeutic advantages.

Compounds to be administered therapeutically by the in vivo method may be prepared as described above, and are also preferably dialdehydes synthesized from a diacetal. Formulations containing the oxidized polyamines or pharmaceutically acceptable salts thereof may also be used in this method, including ingredients such as conventional pharmaceutically acceptable carriers, like saline or sterile water, or ingredients to aid solubility or preservation of the formulation.

The preferred in vivo mode of administration of the compounds according to the method of this invention to achieve the desired immunosuppression is parenteral, more preferably intravenous or subcutaneous, and most preferably subcutaneous. It is not believed, however, that the specific mode of administration is critical to the practice of the present method so long as an effective amount of the compound enters the blood stream.

In certain embodiments, the present inventors have found that about 5–10 mg/kg of sperminc dialdehyde administered intravenously or subcutaneously was effective to suppress graft vs. host reactions, as detailed in the Examples section. However, it is believed to be well within the skill of a practitioner in the field to determine other appropriate doses of compounds and frequencies of administration to achieve the desired immunosuppressive response. Subcutaneous dosing of about 10 mg/kg i.p. −20 mg/kg i.p. correlated well with the i.v. dosing. It is contemplated that for subcutaneous administration, those skilled in the art would recognize the necessity to increase the dose. Accordingly, the only practical limits are dictated by optimum efficacy, and hence, all such doses, frequencies of administration, and modes of administration are intended to be included within the subject method.

Efficacy of the method of the invention may be determined by one skilled in the art through the use of many direct or indirect observations of the clinical manifestations of graft vs. host reactions (either in the human or in one or more animal species) such as hunched back, diarrhea, alopecia, poor physical condition, wasting, and in the most drastic cases, death. Reduction of these symptoms would be an indication that the compound is exerting its effect, at the chosen dosing. Signs of toxicity, for example, leukopenia, anemia, lack of reconstitution, and the like would indicate that the dosage should be reduced.

Indirect measurement of efficacy may also be useful in establishing and monitoring dosage levels. For example, many routine assays may be carried out to track the efficacy of the treatment regime. Those skilled in the art may assay the cytotoxic T cell populations by mixed lymphocyte reaction assays, using peripheral T cells. Secondly, skin graft prolongation has long been used by immunologists to predict the efficacy of compounds in suppressing organ rejection. For instance, anti-thyl antibody (mouse equivalent of Orthoclone OKT3) (R. M. Gorcyzynski, M. Boulanger and C. Lau. J. Immunol. 138:3197–3202 (1987)), FN18 (Frans J. M. Nooij and Margreet Jonker, "The effect on skin allograft survival of a monoclonal antibody specific for a polymorphic CD3-like cell surface molecule in rhesus monkeys". Eur. J. Immunol. 1987. 17:1089–1093), (monkey equivalent of Orthoclone OKT3) were all effective in suppressing skin graft rejection and Orthoclone OKT3 turned out to be effective in suppressing solid organ rejection in humans (Cosimi, A. B., Burton, R. T., Colvin, R. B., Goldstein, G., Delmonico, F. L., Laguaglia, M. P. Tolkoff-Rubin, N., Rubin, R. H., Herrin, J. T., and Russell, P. S., Transplantation 1981.32:535). CsA, a potent immunosuppressive molecule for organ transplantation is also effective in skin graft experiments. Taken together, these data suggest that sperminc dialdehyde, which is more effective than a comparable dose of CsA, should be at least as active as CsA in stopping organ rejection after transplantation.

Hypersensitivity is involved with allergic reactions (DeWeck, A. 1983. Regulation of IgE responses, New Trends in Allergy, J. Ring and G. Burg (eds.). Springer-Verlag, Berlin) and autoimmunity (allergic encephalomyelitis) (Weigle, W. O. 1980, Analysis of autoimmunity through experimental models of thyroidiris and allergic eneephalomyelitis, Adv. Immunol. 30, 159). The fact that sperminc dialdehyde suppressed DTH suggests that it might be useful in certain forms of autoimmunity. One injection in the footpad would suppress swelling and inflammation, suggesting that it can be used for treatment of inflamed joints in Rheumatoid Arthritis (RA) patients through direct injection into the joint. For RA patients experiencing acute flare of the disease, direct injection into the joint with prednisone is a very common treatment. Sperminc dialdehyde could supplement or substitute for prednisone in the treatment of inflamed joints in RA patients.

Bone marrow toxicity and tumor cell or immune responsive T lymphocyte resistance are the two major limiting factors in bone marrow transplantation. Identification of different ALDH isozymes (in hemopoietic cells and contaminating cells) using specific immunological probes and inhibitors would facilitate the development of optimal conditions for SDA to selectively eliminate the uneconomic species and thereby possibly offer an enhanced therapeutic margin of safety.

The following examples more specifically describe certain embodiments of the present invention but should not be considered limitative thereof.

EXAMPLES

I. Chemical Synthesis of N'N'-Bis(3,3-diethoxypropyl-1,4 butanediamine nitrate spermine (bis-acetal)

All materials were obtained from Aldrich. All reactions are run under an atmosphere of nitrogen, and solvents are either HPLC grade (methanol, methylene chloride, NMP, ethyl acetate) or anhydrous "Gold Label" grade (THF).

1. Preparation of N-(3,3-diethoxypropyl)phthalimide (Compound 1), A mixture of 3-chloropropionaldehyde diethyl acetal (16.7 g, 0.10 mol) and potassium phthalimide (18.5 g, 0.10 mol) in N-methylpyrrolidinone (200 ml) was stirred overnight at 125° C under nitrogen. The resulting solution was cooled and poured into water (400 ml) and the resulting mixture was extracted with ether (2×200 ml). The ether extracts were washed with water (2×100 ml), dried (MgSO4), filtered, and evaporated to leave an orange oil. Chromatography on silica (200 g) with 95:5 methylene chloride-ether provided pure Compound 1 as a pale orange oil (16.5 g, 60%).

2. Preparation of 3,3-diethoxypropylamine (Compound 2), A solution of N-(3,3-diethoxypropyl)phthalimide (1) (16.5 g, 59.5 mmol) and hydrazine (3.8 g, 120 mmol) in methanol (300 ml) was stirred at reflux for 4 hours (a mechanical stirrer was necessary as the mixture thickened considerably). The mixture was cooled with continued stirring, and filtered, washing the precipitate with methanol. The tiltrate was evaporated to a semi-solid mass, which was taken up in methylene chloride (150 ml) and filtered again. The tiltrate was concentrated and the residue was distilled in vacuo to provide Compound 2 as a colorless liquid (6.5 g, 70%). (The reported boiling point is ca. 60° C at 4 mm of Hg, ca. 70° C. at 20 mm of Hg.).

3. Preparation of N,N'-bis(3,3-diethoxypropyl)succinamide (Compound 3), A solution of succinyl chloride (3.25 g, 21.0 mmol) in methylene chloride (50 ml) is added dropwise with vigorous stirring to a cold (−50° C.) solution of Compound 2 (6.14 g, 41.7 mmol) and triethylamine (6.3 ml, 45 mmol) in methylene chloride (200 ml). The mixture was allowed to warm to room temperature and stirred under nitrogen overnight. The solvent was evaporated and the residue was taken up in ether (200 ml). The resulting suspension was filtered, and the filtrate evaporated. The residue was chromatographed on silica (150 g) with 6:1 ethyl acetate-isopropanol, and the product recrystallized from hexane to provide compound 3 as a colorless solid, mp 89°–90° C.

(4.2 g, 53%). The material decomposed over a period of two months when stored at room temperature.

4. Preparation of N,N'-bis(3,3-diethoxypropyl)butane-1, 4-diamine dinitrate (Compound 4), A mixture of Compound 3 (4.0 g, 10.6 mmol) and lithium aluminum hydride (0.84 g, 22 mmol) in tetrahydrofuran (200 ml) was refluxed under nitrogen for 40 hours, then cooled. Water (1.0 ml), 15% aqueous o sodium hydroxide (1.0 ml), and more water (3 ml) were added dropwise with vigorous stirring. The mixture was stirred for 30 minutes, then filtered. The filtrate was evaporated, leaving a pink oil. This was taken up in ethanol (20 ml), diluted with 50 ml ether, and concentrated nitric acid (1.3 ml) was added dropwise with vigorous stirring. A precipitate formed quickly, which was collected by filtration and washed with ether. Drying in vacuo provided Compound 4 as a white solid, mp 145°–146° (2.5 g, 50%).

B. Preparation Of Spermine Dialdehyde from Spermine bis-acetal

Spermine bis-acetal is dissolved in 1N HCl at a concentration of 100 mM (47.5 mg/ml). The solution is incubated in a 37° C. water bath for an hour. At the end of the incubation period, the 100 mM solution is diluted to 20 mM with purified water. The pH of the 20 mM solution is adjusted to between 5.0 and 6.5 using 10N NaOH. This pH adjusted 20 mM solution is the stock for all test material.

Preparation of Control Article

Control vehicle stock solution is obtained by titrating a 0.2M HCI solution with 10N NaOH and adjusting the pH to between 5.0 and 6.5. To obtain a control working solution, the stock solution is then diluted accordingly as with the test solution.

Material Used for Bioassays

The following materials were used in the Examples. Purified phytohemagglutinin (PHA-P) was obtained from Wellcome. Pokeweed mitogen (PW1VI) was obtained from Gibco. Tritiated thymidine and chromium (51Cr) were obtained from New England Nuclear. Con A was obtained from Sigma. C57/B6, DBA/2, C3H and Balb/C mice were obtained from the Jackson Laboratory. Growth medium for human cell lines consisted of δ-minimum essential medium (δ-MEM) (Gibco) supplemented with penicillin (Gibco, 50 Mg/ml), streptomycin (Gibco, 100 Mg/ml), L-glutamine (Gibco, 2.0 mM) and 2–10% fetal calf serum (FCS, Gibco). The medium for the T cell proliferation assay was the same except RPMI 1640 (Gibco) was used instead of δ-MEM; 10% FCS was used at all times.

C. Preparation of Mouse Bone MaXrow and Spleen Cells

Mice were sacrificed by cervical dislocation and disinfected by dipping in a Dettol solution. Bone maxrow cells were obtained from suitable long bones by flushing with a 0.25 gauge needle. Cells were then washed three times with RPMI before use.

Spleen cells were prepared by passing the spleen through a fine wire mesh. Cells were resuspended in RPMI and washed three times before use.

D. Preparation Of Human B and T Lymphocytes and Lymphocyte Proliferation

Peripheral blood lymphocytes (PBL) were obtained from the blood of normal donors by using standard Ficoll-Hypaque gradient techniques. The T and non-T cells were separated by standard sheep red blood cell (SRBC) rosetting technique. Briefly, $5 \times 10^6$/ml PBL were incubated with 1% neuraminidase-treated SRBC, and rosetted cells were separated from non-rosetted cells on a Ficoll-Hypaque gradient. The rosetted cells were designated as T cells. Purified B lymphocytes were obtained from non-rosetted cells by removal of residual T cells using the Pan T monoclonal antibody OKT 11 and complement.

E. Human Lymphocyte Proliferation

T cell proliferation: $7 \times 10^4$–$10^5$ human T lymphocytes were cultured in flat bottom microtiter plates (Flow) in the presence of 0.1% PHA-P or 1/64 PWM for 4 days. 3H-thymidine (0.1 MCi/well) was added for the last 6 hours of the culture period. T cell dependent B cell proliferation: $4 \times 10^4$ T cells and $10^5$ B cells were cultured together in the presence of 1/64 dilution of PWIVI for 4 days. 3H-thymidine was added for the last 6 hours of the culture period. B cell proliferation was carried out in exactly the same manner with no T cells added to the culture. In all cases, cells were subsequently harvested onto filter paper using a multiple-channel automated cell harvester (Flow) and washed repeatedly with distilled water. Cell associated radioactivity was determined by scintillation counting in an automated counter. All of the results were expressed as % response calculated according to the formula:

$$\% \text{ response} = \frac{\text{cpm of supernatant-treated cultures}}{\text{cpm of control cultures}} \times 100$$

F. Mouse Lymphocyte Proliferation

Mouse spleen cells were cultured for 3 days in fiat bottom microtiter plates at $10^5$ cells per well in the presence of 2 mg/ml of Con A. 3H-thymidine (0.1 microcurie/well) was added for the last 4–6 hours of the culture period. Cells were harvested as described above.

G. Bone Marrow Transplantation in the Mouse Model

In bone marrow transplantation, bone marrow cells from normal donor mice were transplanted to totally histoincompatible and lethally irradiated recipients. All recipient mice received 9.5 Gy (950 rads) total body irradiation on day 0 and were then housed in microisolator cages thereafter. They were given autoclaved rodent laboratory chow throughout the whole study and also were allowed to feed ad libitum. Recipients also received 1.5 mg/kg of gentamicin subcutaneously for 20 days after irradiation. On the day of irradiation, bone marrow cells mixed in 3:1 ralo with spleen cells were removed from donors and incubated for an hour with different concentrations of sperminc dialdehyde. Spleen cells were added to intensify subsequent graft vs. host disease (GVHD). After incubation, cells were washed 3 times and then injected intravenously into irradiated recipients. Signs of GVHD and survival were scored every day thereafter.

H. Graft Vs. Host Reaction in Rat (Popliteal Lymph Node Study) According to Method of Ford et al. Transplantation. Vol. 10. pp. 258-266 (1970), Graft vs. host reaction in rats was measured by popliteal lymph node enlargement induced by reinjection of parental spleen cells into F1 recipients. (Lewis x BN) F1 rats were divided into groups of 10 and given daily IV injections of different doses of the test compound (spermine dialdehyde) or control preparation. Two days after the first injection, they received $9 \times 10^6$ spleen cells from the parental Lewis strain (0.3 ml of a $27 \times 10^6$ cells/ml preparation was injected under the skin of the ventral surface of each of the recipient's right hind foot). Injection of test compound and control article continued for 6 more days. On the seventh day, rats were sacrificed by $CO_2$ treatment. Both left and right popliteal lymph nodes were removed and cleaned of any adhering tissue. The extent of enlargement was measured by weighing both left and right lymph nodes and differences between the two were calculated.

I. Generation of Cytotoxic T Cells in Mice (In Vivo)

In vivo generation of cytotoxic T cells was performed according to the method described by Faanes et al., Clin. Esp. Immunol., Vol. 27, pp. 502-506 (1977). C57BL mice were arranged into groups of 10 and injected IP with different doses of sperminc dialdehyde or control preparation. Two days after first injection, they received i.p. injections of $10^7$ DBA spleen cells which were prepared as described previously. Ten days after cell injections, C57 mice were sacrificed by cervical dislocation and cytotoxic T cells generated in the spleen were quantified by measuring the ability of those cells to lyse 51Cr labelled P815 taxget cells (a mastocytoma, cells of DBA origin or Con A stimulated DBA spleen blasts). P815 cells or blasts were suspended at $10^7$ cells/ml and incubated with 200 mci of 51Cr for 1 hour at 37° C. Cells were then washed 3 times and then mixed with C57BL spleen cells at ratios of 20: 1, 10:1 and 5:1 (C57BL:P815) in a V-bottom microliter plate with a final volume of 200 ml. Cells were spun for 6 minutes and incubated for 4 hours at 37° C. After incubation, 100 ml of supernatant was removed and counted in the gamma counter. The percentage of cytotoxic T cells was calculated:

$$\% \text{ total cytotoxicity} = \frac{51Cr \text{ released by spleen cells} - \text{spontaneous release}}{\text{Total release} - \text{spontaneous release}} \times 100$$

J. Acute Toxicity

Two pairs of Swiss Webster mice were injected intraperitoneally at 200 mg and 400 mg/kg respectively and observed for toxic effects. Control groups were injected with control preparation. Two weeks after dosing, animals were necropsied and organs were examined for abnormalities.

K. Aldehyde Test

Aldehyde test was performed according to the method described by Sawicki et al., Analytical Chem., 33, 93-96 (1961). Briefly, 50 Ml of 0.4% solution of 3-methyl-2-benzothiazolone hydrazone (MBTH) was added to 50 Ml of the test solution. The mixture was allowed to stand at room temperature for 30 minutes, then 200 Ml of a 0.2% solution of ferric chloride was added and the mixture was then left at room temperature for 10 minutes. Six hundred and fifty Ml of acetone was then added to the sample with slow agitation and the color intensity of the sample was quantitated by spectrophotometric reading at wavelength 670.

L. In a skin graft transplant experiment, Balb/c ($H2^d$) skin grafts were transplanted onto C3H mice according to the procedure described in 1. Sperminc dialdehyde was administered s.c. right after transplantation and continued throughout the study. Cyclosporin A (CsA) was run along as a positive control.

M. Delayed Type Hypersensitivity

Figure 7:
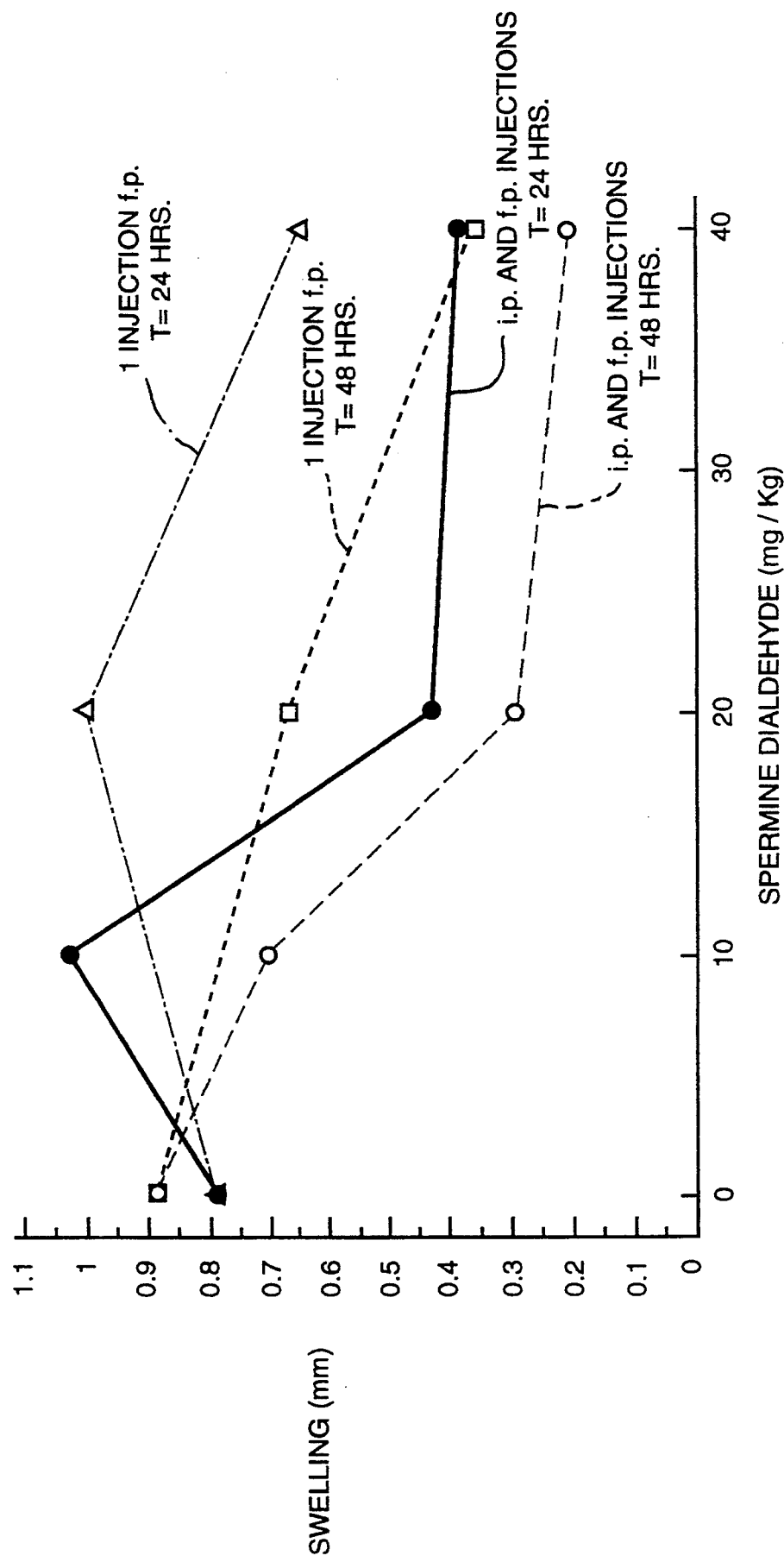
FIG. 7 Delayed type hypersensitivity was induced in the footpad of B6D2F1 mice and swelling measured in min. Sperminc dialdehyde was administered i.p. and i.m. at various time periods.

Delayed type hypersensitivity was induced in the footpad of B6D2F1 mice by using sheep red blood cells (SRBC) as the antigen. Briefly, 0.2 ml of 0.01% SRBC was injected i.v. into B6D2F1 mice. Four days later, they were challenged in the footpad with 50 $\mu l$ of 20% SRBC. Swelling of the footpad was measured 24, 48, and 72 hours later. Sperminc dialdehyde was administered i.p. initiating from the day before immunization. After challenge in the footpad, B6D2F1 mice were given an intramuscular (i.m.) injection beside the challenge site one hour after challenge. Some mice received no i.p. administration and were only given one i.m. injection after the challenge. Results are shown in FIG. 7.

N. Bioassay For Screening of Analogues

In order to establish suitable bioassays for screening of analogues, it was considered appropriate to ascertain whether or not SDA is equal to or better than the well-known polyamine interfering agents. As shown in the table below, the potency of SDA was similar to certain polyamine analogues, bis (ethyl) spermine (Porter et al. 1987) and to DFMO, an irreversible inhibitor of ornithine decarboxylase (Metcalf et al. 1978).

Moreover, unlike DFMO and bis-spermine, SDA was capable of inhibiting both of the key enzymes of polyamine biosynthesis, thereby eliminating the compensatory response and ensuring complete inhibition of polyamine synthesis. SDA, like the other two agents did not inhibit the enzymes of unrelated pathways indicating the specific interaction with polyamines. Similar bioassays may be used by those skilled in the art to identify desired SDA analogues taught herein.

| Drug | T cell Proliferation | Leukemic cell growth | Ornithine decarboxylase | AdoMet decarboxylase | Acid phosphatase | Alkaline phosphatase |
| --- | --- | --- | --- | --- | --- | --- |
| Spermine Dialdehyde | +++ | +++ | +++ | +++ | − | − |
| *Difluoro Methyl Ornithine | ++ | ++ | ++++ | ± | − | − |
| **Bis(ethyl) | +++ | +++ | ++++ | − | − | − |

| Drug | T cell Proliferation | Leukemic cell growth | Ornithine decarboxylase | AdoMet decarboxylase | Acid phosphatase | Alkaline phosphatase |
|---|---|---|---|---|---|---|
| Spermine | | | | | | |

*Metcalf et al., J. Am. Chem. Soc. 100, 2551-2553 (1978),
**Porter et al., Cancer Research 47, 2821, 1987

II. RESULTS

A. Effect of Sperminc Diaaldehyde on Human T and B Lymphocytes

Figure 1:
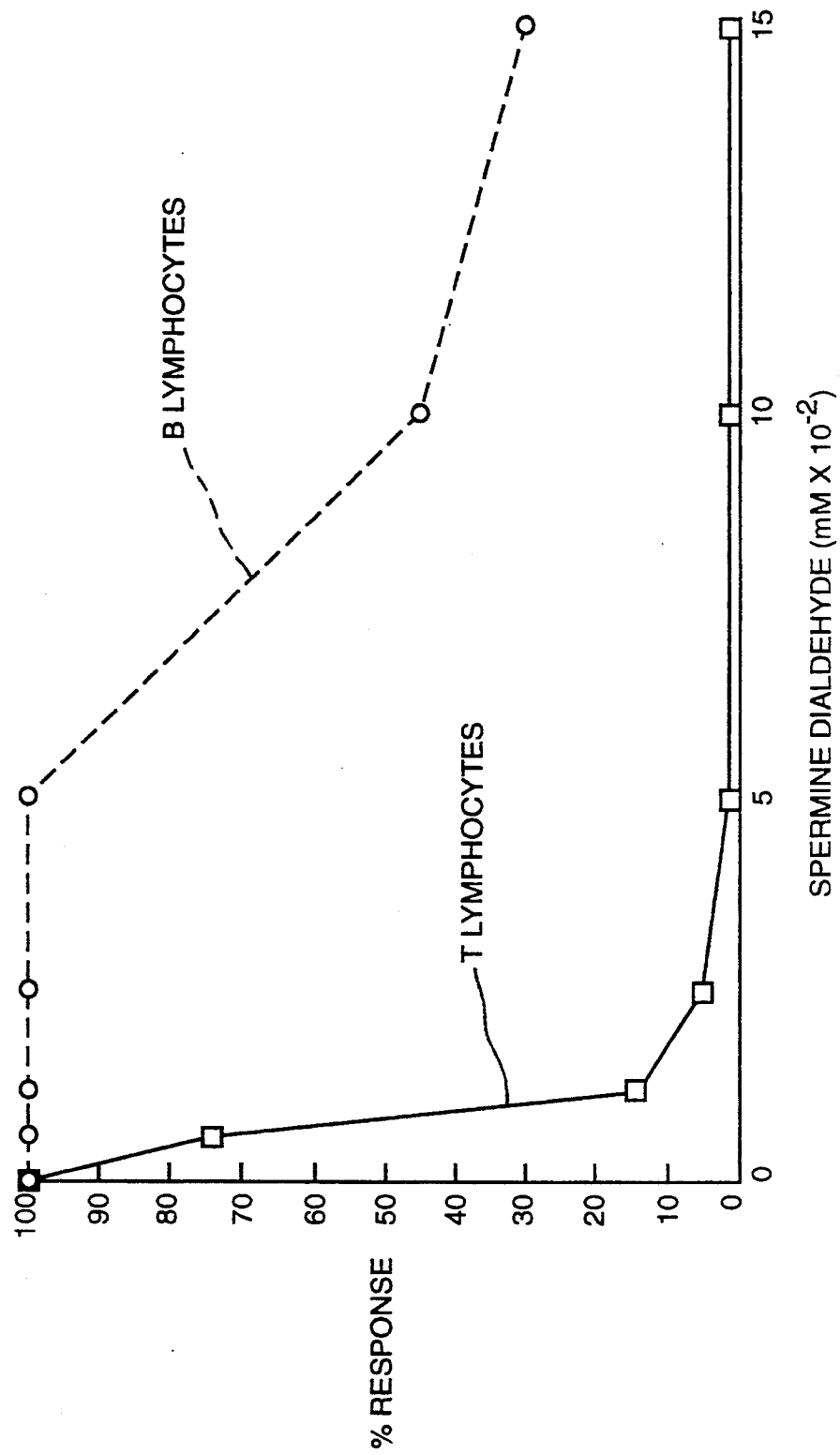
FIG. 1 Human T & B lymphocytes were incubated separately with different concentrations of spermine dialdehyde in vitro for 1 hour. Cells were washed extensively and set up in a PHA (for T cell) or PWM (B cell) proliferation assay. A graph is depicted wherein percentage of response is plotted as a function of concentration of sperminc dialdehyde.

Human lymphocytes were prepared and separated into T and B lymphocytes as described previously. T and B lymphocytes were incubated with different concentrates of sperminc dialdehyde for 1 hour at 37° C. Cells were washed 3 times with RPMI and were then set up in a PHA driven T cell proliferation assay or pokeweed mitogen (PWM) driven B cell proliferation assay. Results are illustrated in FIG. 1. As can be seen, sperminc dialdehyde inhibited T cell proliferation by 85% at $0.62 \times 10^{-2}$ mM whereas a much greater quantity was required to suppress B lymphocyte proliferation. Thus, sperminc dialdehyde preferentially suppresses T cell proliferation with a much less suppressive effect of B lymphocytes. Furthermore, these data suggest that sperminc dialdehyde could irreversibly inactivate T lymphocytes after a brief incubation of 1 hour (5-10 minute incubation was in fact sufficient—data not shown). This novel property distinguishes sperminc dialdehyde from other immunosuppressive molecules such as cyclosporine A or prednisone which are all reversible in nature.

B. Effect of Spermine Dialdehyde on Mouse Spleen and Bone Maxrow Cells

Figure 2:
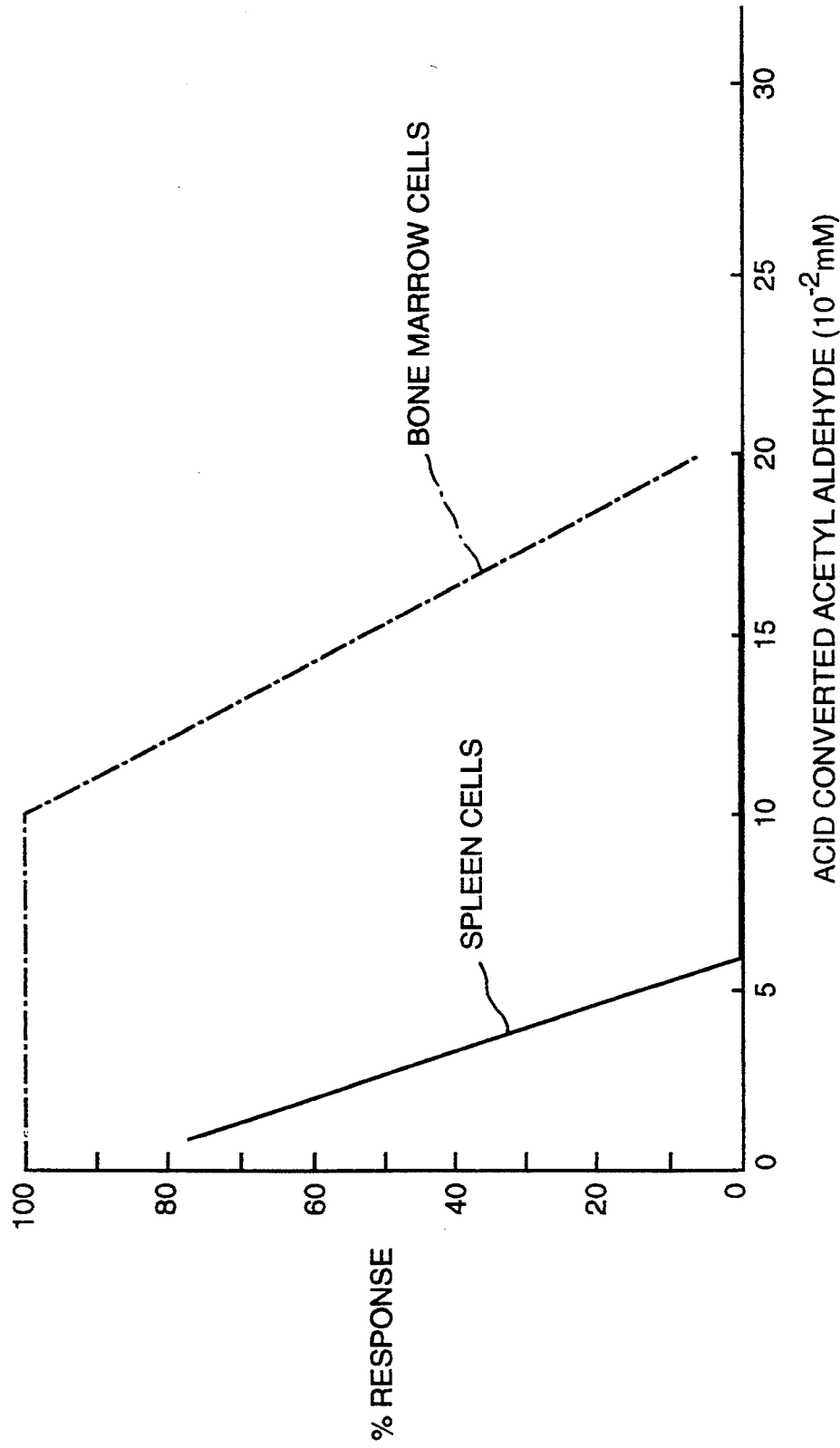
FIG. 2 Mouse spleen and bone marrow cells were incubated separately with different concentrations of sperminc dialdehyde in vitro for 1 hour. Cells were washed extensively and set up in a Con A stimulated proliferation assay. A graph is depicted wherein percentage response is plotted as a function of various concentrations of sperminc dialdehyde.

Mouse bone marrow and spleen cells were each incubated for 1 hour with different concentrations of sperminc dialdehyde. Cells were then washed 3 times with RPMI and set up in a Con A driven proliferation assay. Results are depicted in FIG. 2. Spleen cells, as can be seen, were much more susceptible to suppression mediated by spermine dialdehyde than bone marrow cells.

Figure 3:
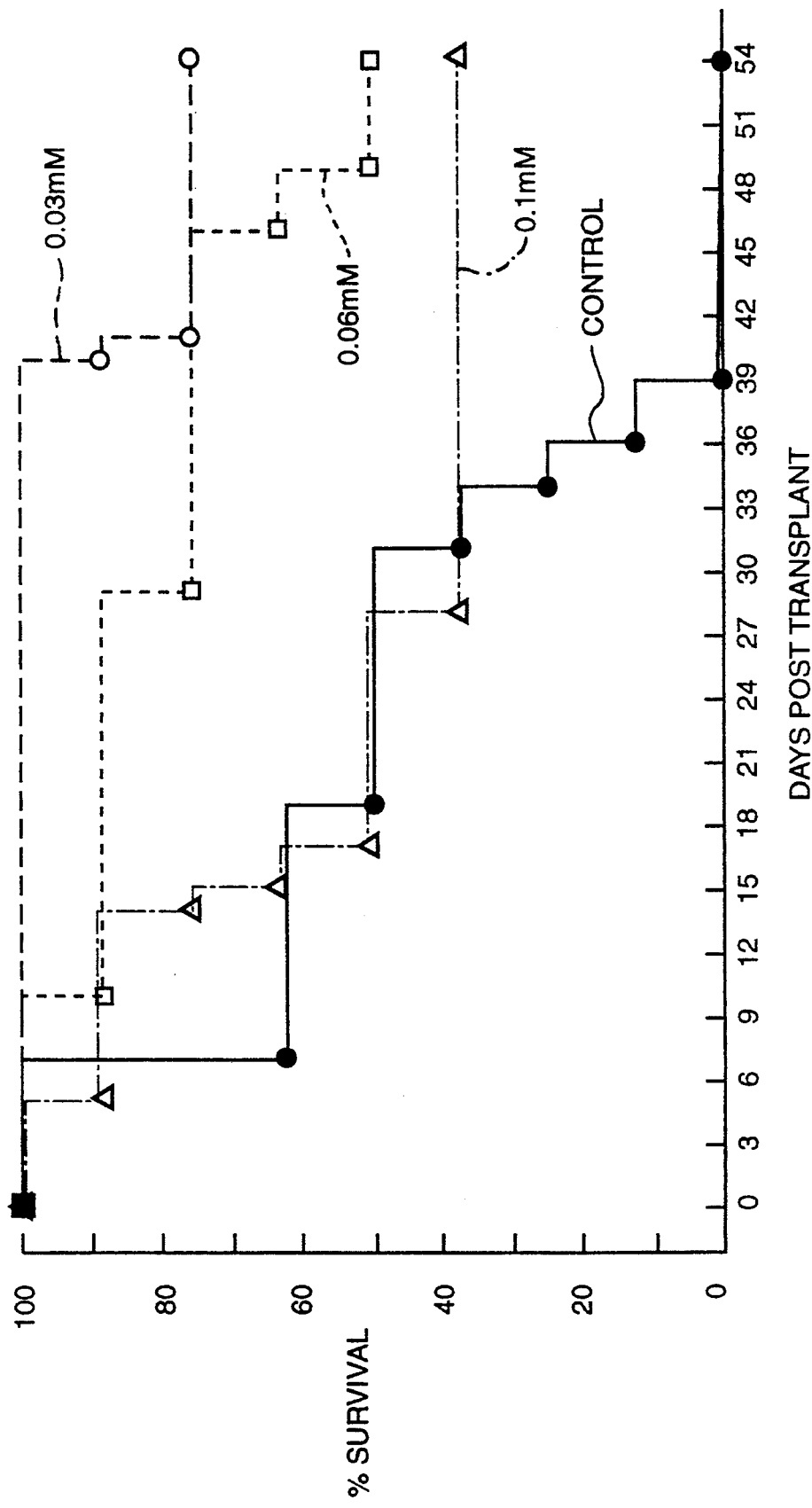
FIG. 3 C57BL spleen and bone marrow cell mixtures were treated with different concentrations of sperminc dialdehyde or control preparation and injected i.v. into lethally irradiated AKR mice. A graph is depicted wherein percentage survival is scored as a function of time.

C. Ex Vivo Treatment of Bone Marrow Graft With Sperminc Dialdehyde Alleviated Graft Vs. Host Disease in Recipients and Prolonged Survival Time Bone marrow and spleen cell mixtures (3:1 ratio) from C57BL mice were incubated with control preparation or various concentrations of sperminc dialdehyde for 1 hour. Cells were then washed extensively and injected intravenously into lethally irradiated histoincompatible AKR mice. Signs of graft vs. host diseases such as hunched back, diarrhea, alopecia, and physical conditions were recorded daily. Survival times of reconstituted mice are shown in FIG. 3. Control mice showed severe signs of acute GVHD initiating around 10 days after transplantation. Mice receiving bone marrow treated with spermine dialdehyde manifested only mild signs of GVHD. The very high dose groups of 0.2 mM exhibited marrow toxicity and animals died around the same time as the irradiated controls probably due to lack of reconstitution. Mice receiving marrow treated with lower doses of spermine dialdehyde (0.03-0.06) showed significantly prolonged survival time. Thus treatment with lower doses of sperminc dialdehyde inactivated T lymphocytes without being toxic to marrow cells and allowed animals to reconstitute with little sign of GVHD. These data suggest that sperminc dialdehyde could be employed to treat human bone marrow samples ex vivo before bone marrow transplantation to alleviate subsequent GVHD which is usually lethal to the patients.

Figure 4:
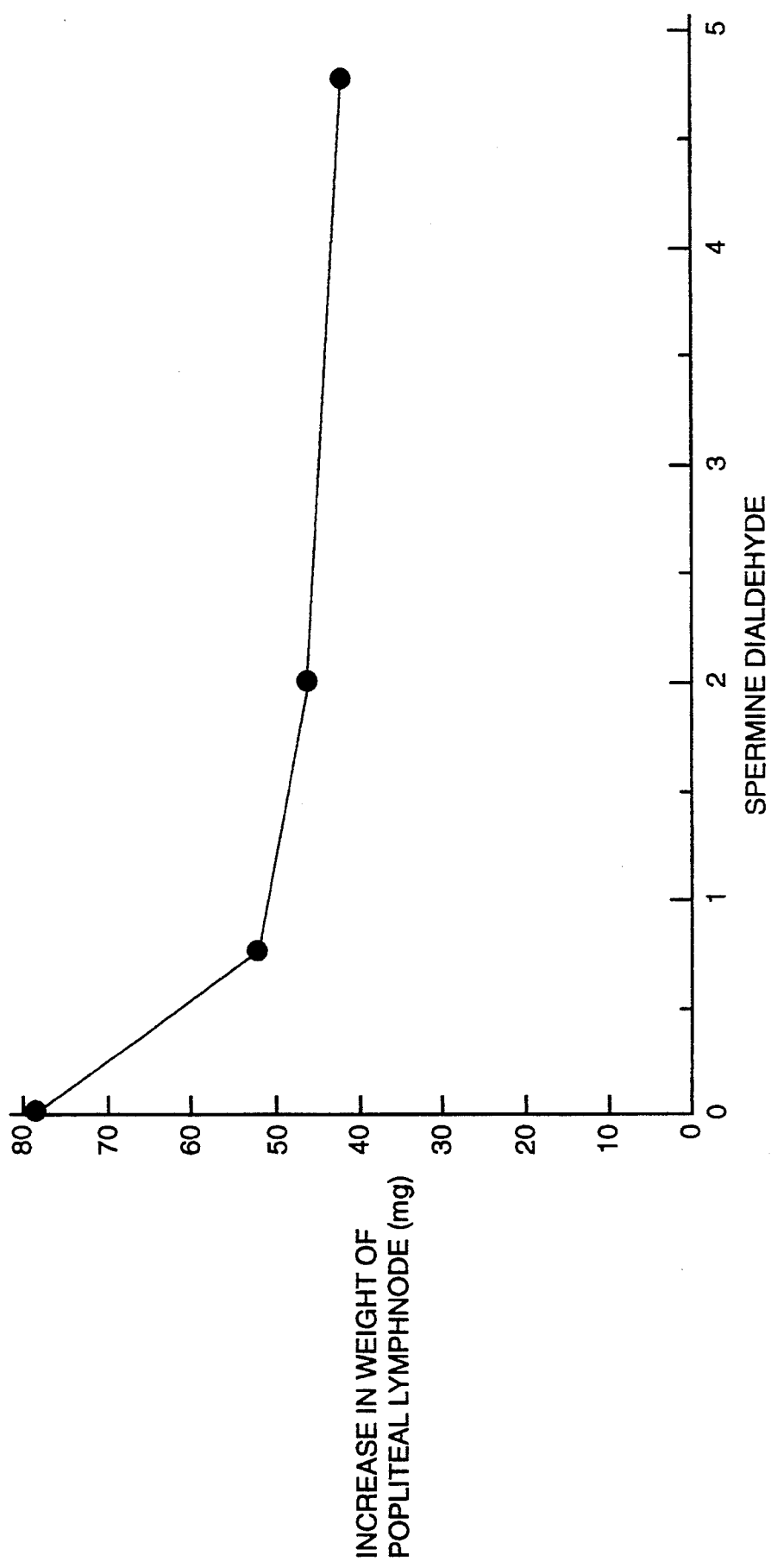
FIG. 4 (LewXBN) rots were injected i.v. daily for 8 days with different doses of spermine dialdehyde. On day 2, BN rat spleen cells were injected subcutaneously into the left foot pads of the (LewxBN)F 1 rats. These rats were sacrificed in 7 days and weights of both left and right popliteal lymph nodes were removed. The difference in weight is plotted as a function of sperminc dialdehyde concentrations used.

D. Suppression of Graff Vs. Host Reaction in Rats by In Vivo Injection of Sperminc Dialdehyde Graft vs. host reaction was generated in the form of popliteal lymph node in F1 recipients by subcutaneous injection of parental spleen cells. Sperminc aldehyde was administered intravenously starting 2 days before parental spleen cell injection and continued until the day of lymph node measurement. Increase in popliteal lymph node swelling was scored by difference in weight between test (left) and control (fight) lymph node. Results were shown in FIG. 4. Substantial swelling was observed in test lymph nodes. Intravenous injection of sperminc aldehyde significantly suppressed the GVH reaction as depicted by diminutive popliteal lymph node swelling. This GVH reaction is a typical manifestation of MHC class II reaction involving allogenic T lymphocytes. Sperminc dialdehyde, when given intravenously suppressed this reaction, suggesting that this molecule mediates the same effect in vivo as in vitro, that is, it acts as a potent suppressor of T cell reactivity.

Figure 5:
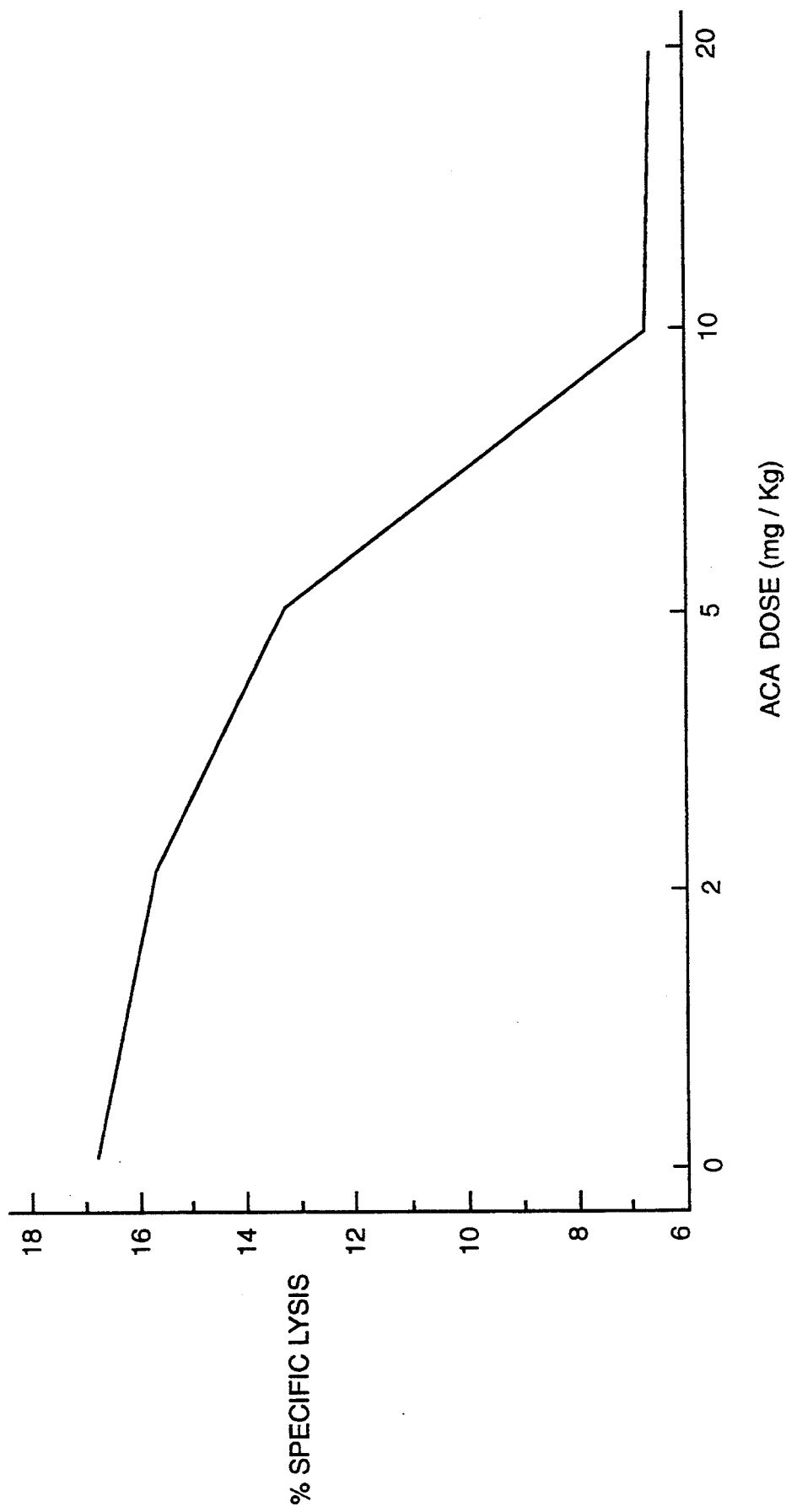
FIG. 5 C57BL mice were injected i.p. daily with different doses of spermine dialdehyde. On day 2, they also received 107 DBA spleen cells. Seven days later, animals were sacrificed and percentage of cytotoxic T cells (measured by % specific lipes generated in the spleen was calculated and plotted as a function of concentration of spermine dialdehyde.

E. In Vivo Suppression of Generation of Mouse Cytotoxic T Cells by Spermine Dialdehyde About 10 days after receiving DBA spleen cells, C57BL mice will generate cytotoxic T cells in their spleens which lyse P815 mastocytoma cells beating DBA specific antigens. Since cytotoxic T cells play an important role in the mediation of organ graft rejection, in vivo suppression of cytotoxic T cell generation may lead to prolonged graft survival. Sperminc dialdehyde, when administered i.p., suppressed the generation of cytotoxic T cells in a dose related manner (FIG. 5). Dose of 10 mg/kg i.p. appeared to attain maximum suppression which corresponds well with the dose required to achieve maximum suppression of GVH reaction in vivo (5 mg/kg i.v., FIG. 4).

The two models described above demonstrated for the first time that synthetic sperminc aldehyde is effective as an immunosuppressive compound in vivo.

F. Acute Topology Results

Two pairs of Swiss Webster mice were injected intraperitoneally at 200 mg and 400 mg/kg for toxic effects. Sperminc dialdehyde appeared to be acutely irritating in these test animals as indicated by squinting and writhing. Mice receiving 200 mg/kg exhibited no other toxic effect whereas those injected with 400 mg/kg showed abdominal or whole body edema for five days. At necropsy 14 days after injection, only the 400 mg/kg group showed any positive findings which consisted of a mildly distended abdomen and scab formation at the injection site. This data differed significantly from results reported by Israel et ai Supra which showed that the LD100 of this molecule is 40 mg/kg.

G. Prolontation of Skin Graft Surval

Figure 6:
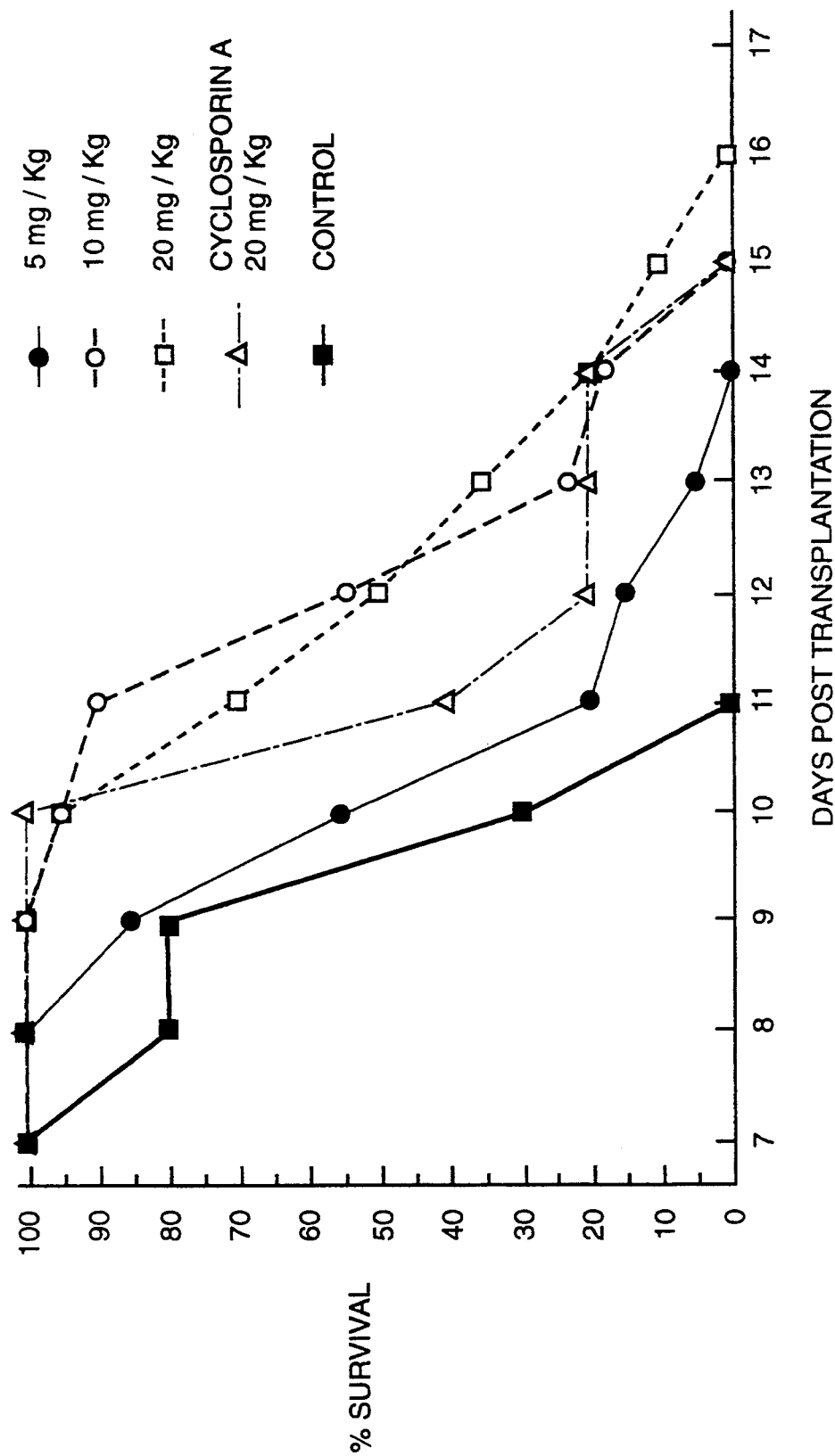
FIG. 6 In a skin graft transplant experiment, BAH/C ($H2^d$) skin grafts were transplanted into C3H mice. Sperminc dialdehyde was administered S.C. right after transplantation, and continued throughout the study. Cyclosporin A was run as a positive control. % skin graft survival was plotted versus days post transplantation.

As depicted in FIG. 6, CsA and all 3 doses of sperrnine dialdehyde prolonged skin graft survival, especially 10 mg/kg and 20 mg/kg of sperminc dialdehyde.

B6D2F1 mice receiving both i.p. administrations and one injection in the footpad showed significant reduction in swelling when measured 24 hours after challenge and also 48 hours later. Mice receiving 1 injection in the footpad did not exhibit reduction in swelling 24 hours later, but did so 48 hours later.

Results suggest that mice receiving spermine dialdehyde both systemically and locally showed reduced swelling measured at 24 or 48 hours after challenge. Mice receiving spermine dialdehyde only after challenge showed swelling similar to that of mice receiving control vehicles 24 hours later. However, 48 hours later, reduced swelling compared to that of the control group was observed.

Delayed type hypersensitivity is a T-cell mediated immune response. After immunization with the antigen, mice would be sensitized with specific T cells responding to the antigen. These T cells will migrate to various parts of the body including the footpad. During challenge with the same antigen, these T cells will be reactivated and result in the release of lymphokines, some of which will be chemotactic for monocytes, macrophages and neutrophils. Accumulation of these cells then leads to a local inflammatory response causing substantial swelling. When sperminc dialdehyde was administered i.p. before and fight after sensitization, it probably suppressed T cell responses to the antigen and after challenge the injection at the footpad suppressed T cells and other cells involved in inflammation (reduction of swelling was not significant if the footpad injection was omitted). However, if injection was given only after challenge in the footpad, suppression of inflammatory response could also be observed 48 hours later. These findings suggest that sperminc dialdehyde suppressed T cell response to the antigen both at the sensitization and inflammatory stages. Suppression, however, was most significant when spermine dialdehyde was administered before and during sensitization and also after challenge. Combined injections suppressed both the generation of sensitized T cells and the de novo inflammatory response.

H. Results of a Bioassay of SDA Analogues—Comparative Studies

Comparative SDA analogues 1–6, listed in the Table below, represent substitution of aldehyde end groups by ester or ketone and reduction in carbon chain length beside the nearest nitrogen. Both methyl and ethyl esters were ineffective in inhibiting the proliferation of T cells/tumor cells or polyamine synthesis. Both methyl ketone (3) and its chloroderivative (4) might show more chemical and metabolical stability than SDA, and one could postulate that they might be suitable for systemic use. However, preliminary in vitro alkylation studies revealed these compounds to be nonspecific alkylating agents, presumably causing DNA breaks/cross-linking, to result in cell death. Subsequently, the chloride was removed and C-chain was reduced, while retaining the ketone group, to yield compounds 5 and 6. The reduction in C-chain from propyl to methyl or ethyl resulted in complete loss of activity (see Table).

Figure 8:
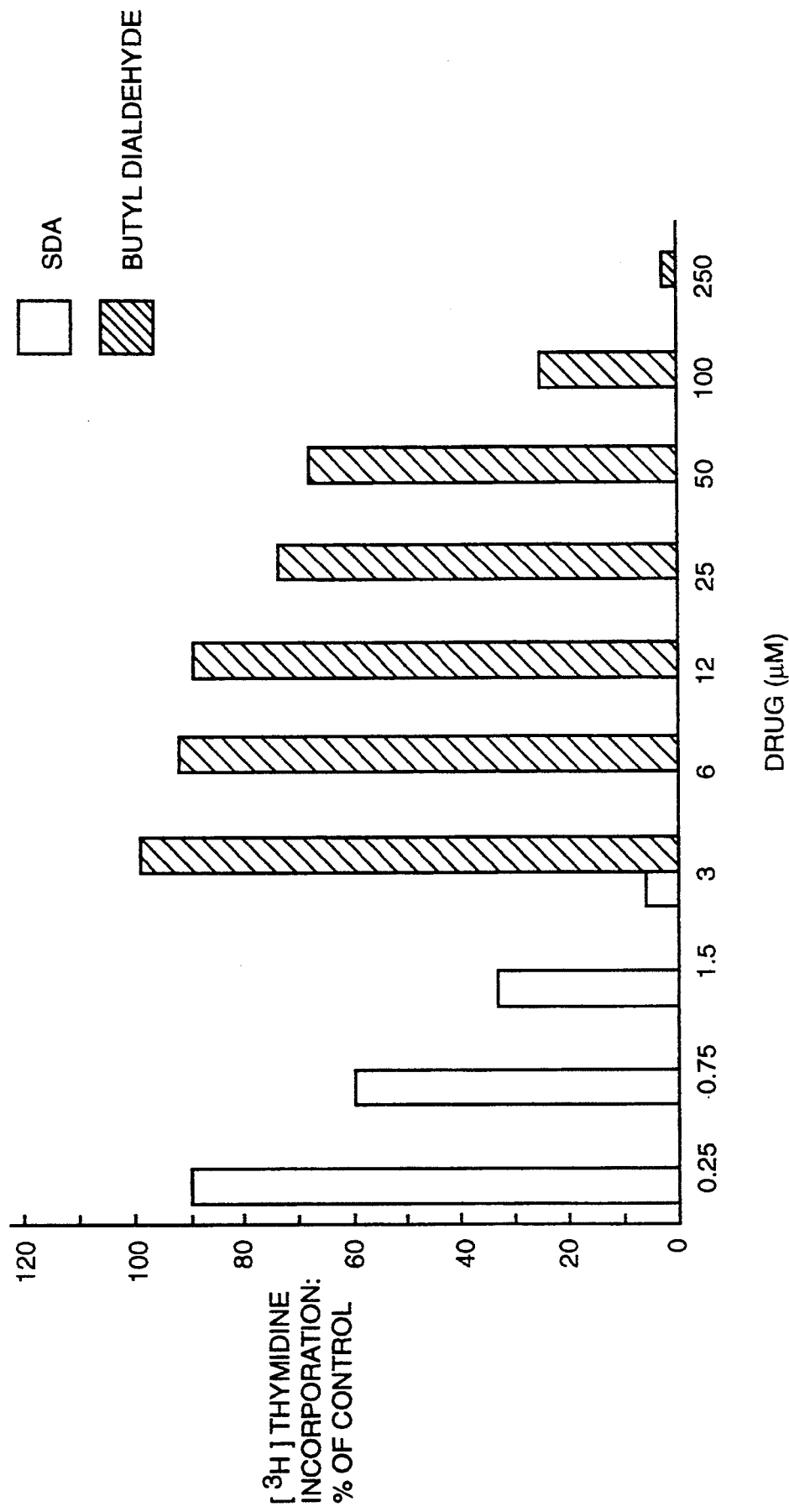
FIG. 8 Effect of SDA and its analogues on Concanavalin A-stimulated splenic T cell proliferation.

Since the aldehyde group in SDA appeared to be critical to antiproliferation activity with intervention in polyamine metabolism, the present inventors have initially sought an aldehyde analogue with a longer C-chain beside the central nitrogen (7). The butyl configuration should make the aldehyde relatively resistant to $\beta$-elimination reactions, yielding a more stable in vivo agent than SDA. Butyl dialdehyde (7) was found to be less potent than SDA in proliferation assays (FIG. 8). However, the compound selectively inhibited adenosylmethionine decarboxylase (FIG. 9), indicating specific interaction with polyamine biosynthesis. The inhibition curves for SDA and butyl dialdehyde were superimposable with $IC_{50}$ values of $0.12–0.13 \times 10^3 M$.

Since DFMO caused a compensatory increase in AdoMetDC, and methyl-glyoxai-Coisguanylhydrazone) (MGBG) inhibited AdoMetDC (FIG. 10), the present inventors have discovered that a SDA-like compound is ideal for the inhibition of polyamine biosynthesis. Analogues which inhibit both the key enzymes and are metabolically more stable than SDA, such as butyl dialdehyde, and its analogues, might be very useful in this regard. Moreover, in vivo characterization of butyl dialdehyde may also offer further insights into the mechanism of action of SDA.

In summary, both ketone and aldehyde analogues of SDA have been shown to be suitable for inhibition of the growth of T cells and tumor cells. However, the studies to date have indicated that only aldehydes cause a suppression of polyamine biosynthesis, and accordingly, are preferred as claimed herein. Chloromethyl ketone was a highly alkylating and non specific toxic agent. Analogues with a shorter carbon chain beside the ketone group showed some attenuation of the biological activity. Based on these observations, aldehyde analogues with an increased C-chain in the side or central part of the molecule, or with an asymmetric configuration (e.g. a monoaldehyde) may also be used in the methods described herein.

| COMPARATIVE STUDIES | | | | |
|---|---|---|---|---|
| | STRUCTURE - FUNCTION RELATIONSHIP | | | |
| SDA AND ITS ANALOGUES | T cell Proliferation | Leukemic cell growth | Ornithine decarboxylase | AdoMet decarboxylase |
| SDA | +++ | +++ | +++ | +++ |

-continued

COMPARATIVE STUDIES
STRUCTURE - FUNCTION RELATIONSHIP

| SDA AND ITS ANALOGUES | T cell Proliferation | Leukemic cell growth | Ornithine decarboxylase | AdoMet decarboxylase |
|---|---|---|---|---|
| ANALOGUE #1 | − | − | − | − |
| ANALOGUE #2 | − | − | − | − |
| ANALOGUE #3 | ++ | + | − | − |
| ANALOGUE #4 | +++ | +++ | − | − |
| ANALOGUE #5 | − | − | − | − |
| ANALOGUE #6 | − | − | − | − |
| ANALOGUE #7 | ++ | ++ | − | +++ |

I. Studies on the Effect of Aldehyde Dehydrogenase in Relation to SDA Treatment

It has been reported in the literature that inhibitors of aldehyde dehydrogenase (ALDH) potentiate the cytotoxic action of cyclophosphamide on pluripotent hemopoietic stem cells and myeloid progenitor cells. Hilton, J. (1984) Cancer Res. 44, 5156–5160; Kohn, F. R., and Sladek, N. E. (1985) Biochem. Pharmacol. 34, 3465–3471; Kohn, F. R., Landkamer, G. L., Manthey, C. L., Ramsay, N. K .C., and Sladek, N. E. (1987) Cancer Res. 47, 3180–3185; Sahovic, E. A., Colvin, M., Hilton, J., and Ogawa, M. (1988) Cancer Res. 48, 1223–1226. Studies were undertaken to determine if ALDH could exert similar modulation to confer differential sensitivity to different cell types for SDA, particularly in purging bone marrow cells contaminated with T lymphocytes and/or tumor cells. Investigations indicate that the antineoplastic and immunosuppressive activity of SDA could be modulated, at least in part, by intracellular ALDH present in target cells. The involvement of ALDH was obvious with the following observations: 1) NAD linked cytosolic ALDH could oxidize SDA to a presumably nontoxic product (spermic acid); 2) murine leukemic cells L1210/CPA and L1210/0, having different levels of ALDH differ in their sensitivity to SDA and 3) the ALDH inhibitor, DEAB, o potentiated the antitumor and lethal effect of SDA on L1210/CPA cells and on specific colonies of hemopoietic progenitor cells.

SDA could be used as a high affinity substrate for cytosolic ALDH in both liver and tumor cells. The known inhibitors, disulfiram, DEAB, and acrolein inhibited ALDH with SDA as substrate, consistent with previous reports on ALDH using other aldehydes. The potent inhibition by acrolein may be particularly important in toxicities associated with SDA treatment. Based on the chemical dynamics of the SDA molecule in solution and its comparison with the metabolism of cyclophosphamide, it can be postulated that SDA could give rise to acrolein by the process of β-elimination under favorable, base catalytic conditions. If acrolein produced by metabolism of SDA were to inhibit ALDH, there would be an increase in the formation of acrolein and an increase in the chances of unrelated toxic effects.

The increased expression of ALDH activity has been shown to be the mechanism of antitumor drug resistance to cyclophosphamide in two experimental murine leukemia cell lines (see above-cited references). ALDH activity was 200 fold higher in L1210/CPA cells compared to wild type sensitive L1210/0 cells. When these cells were treated with SDA, proliferation assays showed that L1210/0 cells were only 2 fold more sensitive than L1210/CPA cells. However, it does not necessarily undermine the impact of ALDH on SDA activity, because in certain studies, the present inventors have found that DEAB pretreatment resulted in equisensitivity for both cell types. Different isozymes of soluble ALDH have been reported to be present in various bone marrow derived cell lines and SDA may not interact with the isozyme(s) present in L1210/CPA as efficiently as cyclophosphamide derivatives. (Russo, J. E., and Hilton, J. (1988) Cancer Res. 48, 2963-2968).

Murine bone marrow cell proliferation, based on [$^3$H]-thymidine incorporation, indicated relatively less cytotoxicity at lower concentrations of SDA; DEAB pretreatment, however, caused dramatic enhancement of SDA action. It may be pointed out that the influence of ALDH on SDA activity would be relevant only at lower concentrations (<20 $\mu$M). At higher concentrations of SDA, the nonspecific toxicity of the drug appears to predominate, irrespective of intracellular ALDH levels. A good correlation was observed between proliferation and appearance of hemopoietic progenitor colonies with respect to SDA dosage. In agreement with previous reports on cyclophosphamide, BFU-E and CFU-GM were found to be more sensitive to SDA in the presence of an ALDH inhibitor. Although the present inventor does not wish to be bound by theory, it is noted that since splenic T cells did not show a differential response to SDA in the presence of similar inhibitors, the selective purging effect of SDA on T cells observed earlier may be attributed to the different ADH levels in different cell types.

Materials and Methods

Materials: SDA was prepared by acid hydrolysis of the corresponding bioacetal supplied by the Department of Pharmaceutical Development at our Institute. [$^3$H]-Thymidine was purchased from New England Nuclear, Boston, Mass. Concanavalin A, horse serum, RPMI-1640 and HEPES were from Gibco, Grand Island, N.Y. NAD and NADP were purchased from Boehringer, Mannheim. Acrolein and disulfiram were obtained from Aldrich Chemical Co., Milwaukee, Wis. Propionaldehyde and benzaldehyde were from Eastman Kodak Chemical Co., Rochester, N.Y. Diethyl aminobenzaldehyde (DEAB) was kindly provided by Dr. John Hilton, Johns Hopkins School of Medicine, Baltimore, Md.

Cell Culture: Murine lymphocytic leukemia cell lines, L1210/CPA and L1210/0 (also known as Le/CPA and Le/0) were kindly provided by Dr. F. Struck, Southern Research Institute, Birmingham, Ala. Cells were grown in RPMI-1640, supplemented with 10% horse serum, 100 units/ml penicillin and 100/$\mu$g/ml streptomycin. The cultures were incubated at 37° C. in a humidified atmosphere with 5% $CO_2$ in air. Bone marrow cells were flushed from femurs of mice with RPMI-1640, using a tuberculin syringe fitted with a 25 gauge needle. For spleen cells, spleens were removed and passed through a fine wire mesh to get a single homogenous cell suspension. In either case, cells were centrifuged, washed twice and resuspended in the drug exposure medium (see below). Cell viability was determined by trypan blue exclusion and the cell suspension was diluted to the desired concentration.

Murine leukemic cells and bone marrow/spleen cells were treated with SDA ($1\times10^{-6}$M to $5\times10^{-5}$M) in RPMI-1640 or PBS based solution. Wherever mentioned, cells were pretreated with DEAB (10–30/$\mu$M) for 30–60 min at 37° C. and then exposed to SDA.

Cell Proliferation Assay: For [hu 3H]-thymidine incorporation, drug or vehicle treated bone marrow or spleen cells were plated in RPMI-1640, containing 10% fetal bovine serum, 10 $\mu$M $\beta$-mercaptoethanol, 25 mM HEPES and 2 mM glutamine. Con-A (4 $\mu$g/ml and 8/$\mu$g/ml) was used as mitogens for bone marrow and spleen cells. Three days later, [$^3$H]-thymidine (0.2 $\mu$Ci/well) was added and cells were harvested after 12–18 hrs. L1210/CPA and L1210/0 cells (0.1–1$\times10^5$ cells/well were plated in RPMI-1640 containing 10% horse serum. [$^3$H]-thymidine was added after 24 hrs and cells were filtered on GF/B filter paper for scintillation counting.

ALDH AShy: Cultured murine leukemic cells and livers (excised from mice immediately after cervical dislocation) were homogenized in 3 volumes of ice-cold 1.15% KCl and 1 mM EDTA. The homogenate was centrifuged at 100,000 g for 45 min and the resulting supernatant was used to measure cytosolic ALDH activity. For particulate ALDH assay, the pellet (and homogenate for total ALDH) was resuspended in homogenizing buffer and treated with 0.25% Triton X-100 for 30 min at 4° C. The solubilized preparations were centrifuged at 48,000 g for 30 min and the supernatants were drawn off for ALDH determinations.

ALDH activity was measured by monitoring the reduction of NAD or NADP for 5–6 rain at 340 nM at 37° C. in DU70 spectrophotometer (Beckman). The assay mixture contained 50 mM potassium phosphate buffer, pH 7.4, 2.0 mM NAD (or NADP) and 1.0 mM EDTA. The reaction was started by adding the substrate (SDA or other aldehyde) to the prewarmed (5 min at 37° C.) assay mixture containing enzyme preparation. Pyrazole (0.1 mM) was added particularly for liver enzyme, to inhibit alcohol dehydrogenase. The apparent $K_m$ and maximum velocity ($V_{max}$) values were calculated using a Lineweaver-Burk plot based on the estimation of the slope by regression analysis. Enzyme activity was expressed as mU (nmoles/min) per mg of protein. Protein contents were determined by the Bradford method, using bovine serum albumin as the standard.

Hemopoietic Colony Formation Assay: Hemopoietic colony forming cells were cultured as described in the art by Iscove & Sieber with minor modifications. SDA/DEAB treated or vehicle treated cells were added to murine hemopoietic culture mixture with erythropoietin and conditioned medium Terry Fox Laboratories, Vancouver, Canada). The mixture was vortexed and 1–2 ml portions ($1\times10^5$ bone marrow cells) were plated in duplicate in 35 mm plastic petri dishes (lux suspension dishes, Flow Laboratories). The culture dishes were incubated in a humidified atmosphere (95% air: 5% $CO_2$) at 37° C. Colonies were counted on day 8 or 10 for BFU-E, CFU-GM and CFU-mix. Colony types were confirmed with Wright-/Giemsa Stain.

Results: Initial studies were designed to investigate the properties of ALDH with SDA as the substrate. In the cytosolic fraction of mouse liver and leukemic L1210/CPA cells, both propionaldehyde and SDA acted as high affinity substrates (see Table). The mean $K_m$ values of SDA for L1210/CPA and liver enzyme were 41.6/$\mu$M and 48.5 $\mu$M, respectively. The specific activity of ALDH (on per mg protein basis) was 1.5 times higher in the liver, as compared to L1210 cells (see Table). With propionaldehyde (1.0 mM) as the substrate for tumor cell and liver enzymes, the specific activity was much higher than the SDA-linked enzyme. Therefore, the specific isozyme(s) interacting with SDA and propionaldehyde may not necessarily be the same or the higher affinity of propionaldehyde for cytosolic ALDH (see Table) may account for the increased enzyme expression.

Cyclophosphamide sensitive L1210/0 cells did not exhibit any detectable enzyme activity with SDA or other aldehydes. Similarly, ALDH activity could not be measured with SDA (up to 2.5 mM) in the mitochondrial fraction of L1210/CPA or mouse liver.

Known inhibitors of ALDH were used to confirm the identity of the enzyme involved in the oxidation of SDA (see Table). Disulfiram and DEAB inhibited ALDH activity with mean $IC_{50}$ values of 4.3/$\mu$M and 0.055/$\mu$M, respectively. Pyrazole, an inhibitor of alcohol dehydrogenase, had no effect on L1210/CPA cytosolic enzyme with SDA as the substrate (data not shown). Acrolein, a highly reactive $\alpha,\beta$ unsaturated aldehyde was also a potent inhibitor of cytosolic ALDH ($IC_{50}$-2.5/$\mu$M, (see Table). The activity of NADP-linked cytosolic ALDH, measured in L1210/CPA cells with SDA as substrate, was in the range of 3.0–3.5 mU/mg protein. The NADP-linked ALDH was found to be far less sensitive to acrolein than the NAD-linked enzyme (50% inhibition at 50–100 mM acrolein).

Both disulfiram and acrolein were very toxic to tumor cells and hemopoietic progenitor cells ex vivo at concentrations much lower than that needed for complete inhibition of ALDH. On the other hand, DEAB, besides being the most potent ALDH inhibitor in vivo and in vitro, showed negligible cytotoxicity even up to 50 $\mu$M. Therefore, in subsequent experiments, DEAB was chosen to study the survival of leukemic cells and myeloid progenitor cells after treatment with SDA.

L1210/CPA and L1210/0 cells treated with SDA showed a concentration dependent decrease in [$^3$H]-thymidine incorporation. L1210/0 cells appeared to be more sensitive to SDA as compared to L1210/CPA, with mean $IC_{50}$ values of SDA being 4.66 $\mu$M and 8.3 $\mu$M, respectively. Pretreatment of cells with DEAB (20 $\mu$M) potentiated the cytotoxicity of SDA in L1210/CPA cells, while having little or no effect on L1210/0 cells. Cell viability estimated immediately after SDA treatment was the same as untreated cells (90%), except for higher concentrations (>25 $\mu$M) of SDA. However, the viability of SDA treated cells dropped sharply over a 12–24 hr period and it appeared as if most of the cells were "programmed to death" during SDA exposure. The remaining cells (<25% viability after 2 days) continued to proliferate and after 6 days of SDA treatment, [$^3$H-thymidine incorporation in these cells was similar to untreated cells, cultured for the same duration.

Murine bone marrow cells, treated with SDA in PBS based medium and cultured in RPMI-1640–10% FBS for 3 days, showed a dose dependent decrease in [$^3$H]-thymidine incorporation. DEAB (30/$\mu$M) pretreatment to these cells resulted in higher susceptibility at lower concentrations of SDA. Under our experimental conditions, ALDH activity could not be detected in homogenates of bone marrow cells. More sensitive conditions, such as specific antibody probes, are suggested to estimate the level of ALDH in these cells. SDA treatment (8–12/$\mu$M) abolished Con A-induced murine spleen cell proliferation, addition of DEAB (20/$\mu$M), however, had no significant effect on the potency of SDA.

Qualitatively similar observations on the role of ALDH were obtained with the bone marrow cell proliferation and the formation of myeloid colonies. SDA treatment caused almost total suppression of BFU-E and CFU-GM colonies at 50/$\mu$M concentration. However, at lower concentrations of SDA (10–25/$\mu$M), DEAB pretreatment further potentiated the sensitivity of myeloid colony forming cells after SDA exposure. Control colony formation ranged from 16–22 colonies and 170–210 colonies per 1×10$^5$ nucleated cells for BFU-E and CFU-GM, respectively.

| Substrate | L1210/CPA | | Mouse Liver | |
|---|---|---|---|---|
| | $K_m$ | $V_{max}$ | $K_m$ | $V_{max}$ |
| SDA | 41.6 ± 5.1 | 6.8 ± 1.6 | 48.5 ± 3.3 | 10.5 ± 3.2 |
| Propionaldehyde | 26.5 ± 4.9 | 10.5 ± 3.2 | 14.0 ± 2.8 | 22.5 ± 3.9 |

ADH activity was measured by monitoring the reduction of NAD at 340 nm, as described in experimental procedures. The $K_m$ and $V_{max}$ values are expressed in $\mu$M and mU/mg protein respectively. Values are ±SEM from 3–4 separate experiments.

PAN T-CELL PURGING ON NK/LAK FUNCTION COMPARED WITH SDA PURGING

EXPERIMENTAL PROCEDURES 3.1 Materials; SDA was prepared by acid hydrolysis of the corresponding bisacetal supplied by the Department of Pharmaceutical Development at The R. W. Johnson Pharmaceutical Research Institute (Raritan, N.J). OKT3 was supplied by Ortho Pharmaceutical (Canada) Ltd. (Don Mills, Ont.). Chromium-51 and [$^3$H]-thymidine were purchased from New England Nuclear, Boston, Mass. PHA-M was purchased from Cedarlane Laboratories, Hornby, Ont. Recombinant murine IL-2 was purchased from Genzyme (Boston, Mass).

3.2 Preparation of Leukocytes Heparinized human peripheral blood was centrifuged at 800 g for 10 minutes. The buffy-coat was removed, diluted 1:1 in sterile PBS and centrifuged for 30 minutes at 800 g over ficoll-hypaque. The PBMN band was removed, washed two times in sterile PBS and resuspended in PBS for SDA treatment or in RPMI-1640 supplemented with 10% FCS for OKT3 treatment. For SDA treatment, the PBMN cells were resuspended in PBS at a concentration of 2 ×10$^7$ cells/ml and a final hematocrit of 7%. The cell suspensions were prewarmed for 10 minutes at 37° C. in a shaking water bath (175 RPM). Appropriate volumes of SDA were then added to the equilibrated cells and the suspensions were incubated for an additional 10 minutes at 37° C. After treatment, the cells were placed on ice, washed in cold RPMI-1640 medium and centrifuged over ficoll-hypaque to remove red blood cells. After 2 additional washes, PBMN cells were resuspended in RPMI-1640 supplemented with 10% FCS and 50/μM 2-mercaptoethanol for counting and viability assessment. Viability as measured by trypan blue exclusion, was always found to be above 95%. Cell concentrations were adjusted to $2.5 \times 10^6$ viable cells for cytotoxic and proliferative assays.

3.4 OKT3 and complement treatment: PBMN cells ($5 \times 10^6$ cells/ml) were incubated with 10 μg/ml OKT3 at 4° C. for 45 min in a total volume of 1 ml. Antibody-coated cells were centrifuged at 800 g and resuspended in a 1:5 dilution of sterile filtered rabbit complement (Cedarlane Laboratories) for 60 rain at 37° C. After treatment, cells were washed twice in cold RPMI-1640, resuspended in RPMI-1640 supplemented with 10% FCS and 50 μM 2-mercaptoethanol and assayed for viability by trypan blue exclusion. Viable cell concentrations were adjusted to $2.5 \times 10^6$ PBMN cells/ml for cytotoxic and proliferative assays.

3.5 PHA-induced proliferation assay: Following SDA or antibody treatment, $2.5 \times 10^5$ cells were innoculated into triplicate wells of flat bottom microtitre plates in the presence or absence of 1 μg/ml PHA-M. The plates were incubated at 37° C. in 5% $CO_2$ for 1–4 days. During the last 18 hours of the incubation period, each well was pulsed with 0.4 μCi of $^3$H-thymidine. Cells were harvested in a Titretek Microharvester and $^3$H-thymidine incorporation was measured in a Beckman scintillation counter and calculated as:

PROLIFERATION (CPM)=PHA-INDUCED CPM—BACKGROUND CPM 3.5 LAK Cell Generation and Cytotoxic Assay: PBMN cells ($2.5 \times 10^6$ cells/ml) were cultured for various lengths of time in 96 well microtitre trays with 50 U/ml IL-2 in a total volume of 200 μl/well. On the day of assay, 1:2 serial dilutions were made producing a range of effector:target ratios, and 5000 $^{51}$Cr-labelled Daudi target cells (ATCC) were added to each well. After 4 hours of incubation, supernatants were removed and $^{51}$Cr content was measured in a gamma counter (Beckman Gamma-4000). Percent lysis was calculated as:

$$\% \text{ Lysis} = \frac{\text{Sample }^{51}\text{Cr release} - \text{spontaneous release}}{\text{Maximum release} - \text{spontaneous release}} \times 100$$

NK activity was assayed in the same manner except that PBMN cells were assayed just after treatment in the absence of IL-2. In addition, $^{51}$Cr-labelled K562 (ATCC) cells were used as the NK target. Lytic unit (LU) calculations were performed using an exponential curve regression program developed by Dr. H. Pross (Queen's University, Kingston, Ont.) [14] where 1 $LU_{15}$ was defined as the number of effector cells required to lyse 15% of the target cells.

4. RESULTS

To determine the effect of the T-cell purging agent SDA on NK and LAK activity, PBMVIN cells were incubated for 10 rain with 1.75 or 2.5 mM SDA, washed and then tested for NK and LAK activity. Treatment of PBMN cells with either 1.75 or 2.5 mM SDA resulted in complete abolition of NK activity as measured in the 4 hr $^{51}$Cr release assay against the NK target K562 (Table I). Similarly, LAK activity assayed against $^{51}$Cr-labelled Daudi target cells could not be generated following 1 or 2 days of culture of SDA-treated PBMN cells with 50 U/ml IL-2 (Table II); however, increased culture time resulted in a 15–50% dose-dependent recovery of LAK activity as compared to control cultures. As an index of T-cell activity, PBMN cells were also assayed for mitogen-induced proliferation. Table III shows that, similar to the recovery of LAK activity, recovery was also observed in response to the T-cell mitogen PHA in that proliferative activity was eliminated after SDA treatment but was partially restored after 3 and 4 days of culture.

In order to compare the effects of SDA and currently used bone marrow purging techniques on NK/LAK activity, we selected OKT3 and complement as an example of a pan T-cell purging agent. OKT3 and complement treatment of PBMN cells resulted in up to a 3 fold increase in NK activity (Table IV) and up to a 2 fold increase in LAK activity (Table V). PHA induced T-cell proliferation was, however, markedly reduced with OKT3 and complement treatment and did not recover appreciably with increased culture time (Table VI). These data suggest that OKT3, as a purging agent, is much more T-cell specific than SDA, and has no inhibitory activity against non-T cell effectors.

5. Discussion

In previous studies, we have shown that SDA, at concentrations above 1 mM, completely eliminated murine NK activity and greater than 90% of con A-induced T-cell proliferation [1]. Similar concentrations of SDA have been shown to prevent GVHD and allow high rates of engraftment in murine allogeneic bone marrow transplantation [1]. In this study, we have shown that, as in the murine system, SDA not only inhibited the PHA-induced proliferation of human PBMN cells, but also inhibited NK activity and the ability to generate LAK activity in the presence of IL-2. This inhibition appeared to be transient for at least some of the human PBMN populations since both IL-2-activated cytolytic and PHA-induced proliferative activities began to recover after 3 to 4 days of culture. The significance of this finding is that SDA may be able to eliminate mature, differentiated effector cells (CTL and NK cells) capable of causing GVHD and graft rejection yet spare immature populations of cells capable of immunosurveillance, antileukemic responses and successful engraftment.

The results presented in this report also show a clear difference between the effects of SDA purging and pan T-cell purging on human PBMN cell populations. SDA transiently inhibited LAK activity and the PHA response of PBMN cells and totally eliminated spontaneous NK activity. While OKT3 and complement lysis significantly reduced the PHA response of PBMN cells, this treatment had no inhibitory effect on NK and LAK activities. In fact, NK and LAK activities appeared to be enhanced, possibly due to cytokine release from residual T-cells stimulated with OKT3. Double OKT3 depletion reduced the stimulation to control levels (dam not shown) suggesting that some activated lymphocytes may have survived the initial depletion. Pan T-cell depletion methods, although clinically effective in the prevention of GVHD, have shown high failure rates for engraftment [3, 15, 16]. In addition, even with successful engraftment in human allogeneic transplants using pan T-cell depletion methods, a leukemic relapse rate of up to 50% was observed [17]. The results from these studies emphasize once more the complexity of the engraftment process. Successful transplantation appears to depend not so much on the elimination of specific cell phenotypes, but rather the suppression of the functions mediated by heterogeneous populations.

The findings in this study support in vivo work with both SDA and OKT3 and suggest that SDA may be a promising alternative to pan T-cell depletion methods due to its efficacy in suppressing those cells which mediate the deleterious phenomena associated with bone marrow transplantation (GVHD, rejection and leukemic relapse) while sparing those cells required for engraftment and hematological/immunological reconstitution.

REFERENCES

[1] Wang, E., Conant, J., Li, D., Visconti, V., Chourmouzis, E. and Lau, C. (1990) Bone Marrow Transplant. 6, 235.
[2] Conant, J., Kimsto, L., Wang, E. and Lau, C. (1990) Blood 76, 534a.
[3] Vallera, D. and Blazar, B. (1989) Transplant. 47, 751.
[4] Blazar, B., Soderling, C. Koo, G. and Vailera, D. (1988)Transplant. 45,876.
[5] Ghayur, T., Seemayer, T. and Lapp, W. (1988) Transplant. 45,586.
[6] Azuma, E., Yaxnamoto, H. and Kaplan, J. (1989)J. Immunol. 143, 1524.
[7] Azuma, E. and Kaplan, J. (1988) J. Immunol. 141, 2601.
[8] Naglet, A. and Greenberg, P.(1990) Int. J. Cell Clon. 8, 183.
[9] Andriole, G., Mulé, J., Hansen, C., Lineban, W. and Rosenberg, S. (1985) J. Immunol. 135, 2911.
[10] Rosenberg, S. (1988)Annal. Surg. 208, 121.
[11] Van den Brink, M., Voogt, P., Marijt, W., Van Luxemburg-Heys, S. and van Rood, J. (1989) Blood 74, 354.
[12] Tratkiewicz, J. and Szer, J. (1990) Clin. Exp. Immunol. 80, 241.
[13] Hauch, M., Gazzola, M., Small, T., Bordignon, C., Barnett, L., Cunningham, I., Castro-Malaspinia, H., O'Reilly, R. and Keever, C. (1990) Blood 75, 2250.
[14] Pross, H., Baines, M., Rubin, P., Shragge, P. and Patterson, M. (1981) J. Clin. Immunol. 1, 51.
[15] Kolb, H. J., Rodt, H., Netzel, B., Hale, G., Haas, R. J., Bender-Götze, Ch., Witrearms, W., Waldman, H. and Thierfelder, S. (1988) Exp. Hematol. 13,147 (suppl 17).
[16] Mitsuyasy, R. T., Champlin, R. E., Ho, W. G., Winston, D., Feig, S., Wells, J., Terasaki, P., Billing, R., Weaver, M. and Gale, R. P. (1985) Transplant. Proc. 17, 482.
[17] Hervé, P., Cahn, J. Y., Flesch, M., Plouvier, E., Racadot, E., Noir, A., Couteret, Y., Goldstein, G., Bernard, A., Lenys, R., Bresson, J. L., Leconte de Floris, R. and Peters, A. (1987) Blood 69, 388.

TABLE I

| The effect of SDA on the NK activity of human PBMN cells | |
|---|---|
| Treatment[a] | $LU_{15}/10^6$ PBMN[b] (% control) |
| EXP. 1 | |
| Control | 20.3 |
| SDA 1.5 mM | 0 (0) |
| SDA 2.5 mM | 0 (0) |
| EXP. 2 | |
| Control | 14.4 |
| SDA 1.5 mM | 0 (0) |

TABLE I-continued

| The effect of SDA on the NK activity of human PBMN cells | |
|---|---|
| Treatment[a] | $LU_{15}/10^6$ PBMN[b] (% control) |
| SDA 2.5 mM | 0 (0) |

[a]PBMN cells (2 × 10⁷ cells/ml) were incubated with appropriate concentrations of SDA for 10 minutes at 37° C.
[b]Lytic units per 10⁶ cells tested against ⁵¹Cr-Labelled K562 target cells in a 4 hr NK assay.

TABLE II

| The effect of SDA on the generation of LAK activity in human PBMN cells | | | | |
|---|---|---|---|---|
| | $LU_{15}/10^6$ PBMN Cells (% Control)[b] | | | |
| Treatment[a] | 24 H | 48 H | 72 H | 96 H |
| EXP. 1 | | | | |
| Control | 156.6 | 204.3 | 501.6 | 368.4 |
| 1.75 mM SDA | 0 (0) | 19.4 (10) | 100.8 (20) | 178.7 (48) |
| 2.5 mM SDA | 0 (0) | 0 (0) | 3.8 (1) | 6.9 (2) |
| EXP. 2 | | | | |
| Control | 29.4 | 141.7 | 218.2 | 463.6 |
| 1.75 mM SDA | 0 (0) | 0 (0) | 15.9 (7) | 49.5 (14) |
| 2.5 mM SDA | 0 (0) | 0 (0) | 0 (0) | 0 (0) |

[a]PBMN cells (2 × 10⁷ cells/ml) were incubated with appropriate concentrations of SDA for 10 minutes at 37° C.
[b]Lytic units per 10⁶ cells tested against ⁵¹Cr-labelled Daudi target cells in a 4 hr LAK assay at times indicated.

TABLE III

| The effect of SDA on the PHA-induced proliferation of human PBMN cells | | | | |
|---|---|---|---|---|
| | PHA-Induced Proliferation[b] (CPM [PHA-induced] - CPM [background]) | | | |
| Treatment[a] | 24 H | 48 H | 72 H | 96 H |
| EXP. 1 | | | | |
| Control | 0 | 28950 | 35265 | 46729 |
| 1.75 mM SDA | 0 | 185 | 2307 | 21252 |
| 2.5 mM SDA | 0 | 14 | 882 | 2112 |
| EXP. 2 | | | | |
| Control | 0 | 10847 | 54565 | 66699 |
| 1.75 mM SDA | 0 | 110 | 4950 | 31222 |
| 2.5 mM SDA | 0 | 1 | 292 | 2127 |

[a]PBMN cells (2 × 10⁷ cells/ml) were incubated with appropriate concentrations of SDA for 10 minutes at 37° C.
[b]Proliferation of PBMN cells cultured with 1 μg/ml PHA as measured by ³H-thymidine incorporation at times indicated.

TABLE IV

| The effect of OKT3 and complement treatment on the NK activity of human PBMN cells | |
|---|---|
| Treatment[a] | $LU_{15}/10^6$ PBMN[b] (% Control) |
| EXP. 1 | |
| C' Control | 12.4 |
| OKT3 + C' | 28.0 (226) |
| EXP. 2 | |
| C' Control | 1.9 |
| OKT3 + C' | 6.8 (358) |

[a]PBMN cells (5 × 10⁶ cells/ml) were incubated with or without 10 μg/ml OKT3 for 45 minutes followed by complement for 60 minutes.
[b]Lytic units per 10⁶ cells tested against ⁵¹Cr-labelled K562 target cells in a 4 hr NK assay.

TABLE V

| The effect of OKT3 and complement treatment on the generation of LAK activity in human PBMN cells | | | | |
|---|---|---|---|---|
| | $LU_{15}/10^6$ PBMN Cells[b] (% Control) | | | |
| Treatment[a] | 24 H | 48 H | 72 H | 96 H |
| EXP. 1 | | | | |
| C' Control | 79.5 | 170.7 | 385.7 | 337.4 |

TABLE V-continued

The effect of OKT3 and complement treatment
on the generation of LAK activity in human PBMN cells

| Treatment[a] | $LU_{15}/10^6$ PBMN Cells[b] (% Control) | | | |
|---|---|---|---|---|
| | 24 H | 48 H | 72 H | 96 H |
| OKT3 + C' | 92.2 | 313.9 | 655.6 | 631.4 |
| | (116) | (184) | (170) | (188) |
| EXP. 2 | | | | |
| C' Control | 41.2 | 195.3 | 174.4 | 310.1 |
| OKT3 + C' | 81.9 | 194.0 | 237.1 | 340.8 |
| | (199) | (99) | (136) | (110) |

[a]PBMN cells (5 × 10$^6$ cells/ml) were incubated with or without 10 μg/ml OKT3 for 45 minutes followed by complement for 60 minutes.
[b]Lytic units per 10$^6$ cells tested against $^{51}$Cr-labelled Daudi target cells in a 4 hr LAK assay at times indicated.

TABLE VI

The effect of OKT3 and complement treatment
on the PHA-induced proliferation of human PBMN cells

| Treatment[a] | PHA-Induced Proliferation[b] (CPM [PHA-induced] - CPM [background]) | | | |
|---|---|---|---|---|
| | 24 H | 48 H | 72 H | 96 H |
| EXP. 1 | | | | |
| C' Control | ND[c] | 11,218 | 46,946 | 65,890 |
| OKT3 + C' | ND | <BKGD[d] | <BKGD | <BKGD |
| EXP. 2 | | | | |
| C' Control | 253 | 10,019 | 53,159 | 68,984 |
| OKT3 + C' | <BKGD | <BKGD | 3376 | 13694 |

[a]PBMN cells (5 × 10$^6$ cells/ml) were incubated with or without 10 μg/ml OKT3 for 45 minutes followed by complement for 60 minutes.
[b]Proliferation of PBMN cells cultured with 1 μg/ml PHA as measured by $^3$H-thymidine incorporation at times indicated.
[c]ND = not determined
[d]<BKGD = Below background

SDA AS A PURGING AGENT: SELECTIVE SUPPRESSION OF T CELL AND NK CELL POTATIONS WITHOUT ADVERSE AFFECT ON MYELOID CELLS

Materials and Methods

Spermine dialdehyde (SDA)

SDA is formulated as a sterile 20 mM (4 mg/ml) aqueous solution. Spermine bisacetal was initially hydrolyzed in 1N HCl (37° C., 1 hour) as a 100 mM solution. After hydrolysis, pH of the solution was titrated to 4–4.5 with 1N NaOH while the final concentration of SDA was adjusted to 20 mM with water, USP. The bisacetal is supplied by R. W. Johnson Pharmaceutical Research Institute (US).

Animals and husbandry

All mice were obtained from Jackson Laboratories. BALB/cByJ (H-2$^d$, 7–12 weeks) and C3H/HeJ (H-2$^k$, 8–12 weeks) were used as donor and recipients respectively in all experiments.

Bone marrow, spleen and red blood cells

Blood was taken via the orbital sinus of the donor mice and collected into a test tube containing sterile Alsever solution. Animals were then sacrificed by cervical dislocation. Bone marrow cells were flushed from femurs and tibias with RPMI 1640 (Gibco) using a tuberculin syringe fitted with a 25 g needle. Single cell suspensions of spleen cells were made by forcing the spleens through a fine wire mesh. All cells were washed 3 times in RPM11640 prior to use. Viability was determined by using a trypan blue exclusion test.

Ex vivo incubation with SDA

Spleen cells, bone marrow cells or spleen and marrow mixtures (ratio 1:4) were incubated at 2×10$^7$ cells/ml with varying concentrations of SDA for 10 minutes at 37° C. in a moderately (175 rpm/minute) shaking water bath. In some experiments, donor mouse red cells were added to the cell mixture to adjust the final hematocrit (Hct) to between 2–8%. Incubation was stopped by adding ice-cold RPMI 1640 and the cell mixtures were centrifuged at 2000 rpm (850 g) for 10 minutes. At the end of the first wash, the red cells were lysed by ammonium chloride buffer; cells were then washed 2 more times before assay and/or infusion. Cells treated with up to 2.4 mM of SDA showed viabilities close to that of the control group. The carryover of SDA into the transplanted mice after ex vivo treatment was less than 0.5% as estimated by using radioactive SDA.

Transplant experiments

After ex vivo treatment, the concentrations of the SDA treated BALB/c bone marrow/spleen cell suspensions were adjusted to 6×10$^6$ cells/ml in RPMI 1640 and 1 ml volumes were injected intravenously into lethally irradiated C3H mice (9.5 Gy). After transplantation, the animals were observed daily, up to 63 days, for signs of GVHD such as diarrhea, hunched posture, roughened haircoat, dermatitis and poor physical condition associated with emaciation. They were also weighed every 3 days up to day 21 and once weekly thereafter. Blood samples were drawn from the animals 4 weeks post transplantation to monitor engraftment. The parameters measured were white blood count CWBC), red blood count (RBC) and hemoglobin (Hb).

Myeloid progenitor cell assay

Cell cultures for erythroid and myeloid precursors were carried out in methylcellulose according to the modified method of Iscove & Sieber (25). After SDA treatment, 10$^5$ bone marrow/spleen cells were plated in plastic 35 mm tissue culture dishes (Lux suspension dishes, Flow Laboratories) in murine hematopoietic culture media (Terry Fox Laboratory, Vancouver, Canada). The cultures were incubated at 37° C. in a humidified atmosphere with 5% CO$_2$ in air. Colonies were scored on day 2 for CFU-E and on day 10 for BFU-E, CFU-G/M and CFU-GEMM. Colony types were confirmed with Wright/Giemsa stain (26).

Con A stimulated proliferation assay

The washed bone marrow/spleen cell mixture was suspended in RPMI 1640 supplemented with 10% fetal bovine serum and Con A induced proliferation was performed as described previously (22). To estimate log T cell depletions, limiting dilution experiments were carried out according to the method described by Rozans et at. (27).

Assessment of chimerism

On day 120 post transplantation, surviving animals from groups with a survival rate of greater than 60% were bled from orbital sinus for H-2 typing. The H-2 specificity of the peripheral blood mononuclear cells (PMNs) were monitored using H-2 specific monoclonal antibody in an in vitro complement dependent microcytotoxicity assay (28). In brief, PMNs from each individual mouse was separated on a Ficoll-Paque (Pharmacia) gradient and resuspended in RPMI 1640 at $2\times10^6$/ml. 50 μl of the cells were incubated with 50 μl of the properly diluted (1/50) H-$2^d$ or H-$2^k$ antiserum (PharMingen) at 4° C. for 60 minutes in round bottom microtiter wells. 100 μl of rabbit complement in RPMI 1640+5% FBS was then added to each well. The mixtures were further incubated for 1 hour at 37° C. At the end of this incubation period, cytotoxicity was determined by monitoring the cell viability using a trypan blue exclusion test.

Assessment of natural killer cell activity

BALB/c mice were injected intraperitoneally 16 hours prior to assay with 100 μg polyinosinic polycytidylic acid (POLY I:C). At the time of assay, spleen cells were prepared and treated with SDA as described earlier. SDA-treated cells were counted and dispensed into triplicate wells of round bottom microtrays to give 100:1, 50:1, and 25:1 effector:target (E:T) ratios. Target cells were YAC-1 cells which had been incubated for 1 hour with sodium $^{51}$Chromate, washed twice with PBS and resuspended in culture medium. All wells contained $5\times10^3$ target cells in a final volume of 200/μl. Plates were centrifuged for 5 minutes at 50 xg and incubated at 37° C. in 5% $CO_2$ for 4 hours. Supernatants were harvested using the Skatron supernatant harvesting system and counted in a gamma counter. Maximum release was obtained by counting $5\times10^3$ target cells. Minimum release was obtained from wells containing medium instead of effector cells. The percentage lysis was calculated as $$\frac{\text{cpm of sample} - \text{minimum release}}{\text{maximum release} - \text{minimum release}} \times 100\%$$

Results

Effect of SDA on T cells and bone marrow myeloid cells

Bone marrow cells (containing 20% spleen cells) from BALBc mice were treated with different concentrations of SDA for 30 minutes at 37° C. Cells were then injected into lethally irradiated C3H mice. Irradiated mice receiving no marrow died within 15 days post transplantation. Mice in the control group, receiving saline treated cells, developed severe GVHD (as assessed by the criteria described in Materials & Methods) around day 17–20 and they all died before day 35 post transplantation. Mice receiving 0.1 mM SDA treated cells developed severe GVHD and showed similar survival patterns as mice receiving cells without SDA treatment. Significant prolongation of survival was observed with groups receiving marrow treated with 0.3–0.45 mM SDA. Animals receiving cells treated with 0.6 mM or higher concentrations of SDA did not survive past day 15. They showed no signs of engraftment.

After SDA ex vivo incubation, part of the treated marrow cell mixtures were reserved for in vitro assay. Results for the Con A induced proliferation assay and the myeloid colony assay are listed in Table 1. Total suppression in the proliferation assay was observed with cells treated with 0.3 mM of SDA while the myeloid colony count at that concentration was still approx. 15% of that of the control group.

Effect of hematocrit (Hct) on the selectivity of SDA

The data described above suggest that SDA, although effective in controlling GVHD after ex vivo usage, might have a narrow therapeutic window. However, during the course of the investigation, it was found that the effective dose range of SDA was strongly influenced by the presence of red cells. In the presence of red cells, higher concentrations of SDA were required to mediate T cell suppression while myeloid toxicity was significantly reduced. Studies performed with different red cell concentrations showed that a Hct range of 5–8% appeared to provide the best therapeutic window (T cell inactivation vs myeloid toxicity Table 2). 4-Hydroperoxycyclophosphamide (4HC), another purging agent, also appeared to work optimally at this Hct (29).

Bone marrow cells from BALB/c mice spiked with 20% spleen cells were treated with SDA for 10 minutes at 37° C. in the presence of 6% Hct. Treated cells were then injected to irradiated C3H mice as described previously. In vitro data and in vivo survival results at day 120 after ¢x vivo purging with SDA demonstrates that all the animals receiving cells without SDA treatment died by day 25 post transplantation. Most of the animals that received 0.8 mM or 1.0 mM SDA treated cells developed fatal GVHD similar to the control group and died before termination of the study. About 60–100% of animals in groups receiving marrow treated with 1.2–2.2 mM of SDA were alive 120 days after transplantation. Mice in these groups exhibited little or no GVHD. Cells treated within this range of SDA doses had no Con A inducible proliferation. Limiting dilution studies performed indicated that SDA depleted T cells by 1.3 & 2 logs at 1.4 & 1.8 mM respectively. Residual myeloid colony counts in these groups however still ranged anywhere from 4–40% of the control value. Groups receiving cells treated with 2.4 mM SDA had a lower percentage of survival (40%). Mice that died in these groups manifested signs of lack of engraftment (anemia and bone marrow aplasia). This experiment was performed 3 times with similar results.

On day 28 post transplantation, orbital sinus blood samples were taken from the surviving animals to obtain a hematological profile. Orbital sinus bleeding could not be performed on earlier days due to the fragile physical condition of the animals. The mean value for RBC, WBC, and Hb of the animals receiving cells treated with 1.5–2.0 mM SDA are summarized in Table 3. All test values from these groups fall within the normal range for 2-3 month old BALB/c mice (30).

Evaluation of chimerism

At the end of the study, H-2 specificity of the peripheral blood mononuclear cells (PBMC) from surviving animals was assessed by microcytotoxicity tests to determine the cellular origin of these reconstituted mice. As shown in Table 4, when treated with anti H-$2^d$ antiserum plus complement, the percentage of viable cells in the PBMC of surviving mice receiving bone marrow treated with different concentrations of SDA, ranges from 6–13%. At least 85% of the PBMC from each group were lysed with H-$2^d$ specific antiserum. Thus, it is believed that the cellular origin of these reconstituted animals is predominantly of the donor strain (H-$2^d$).

Effect of SDA on NK cell activity

Spleen cells from BALBc mice primed with poly IC were spiked with autologous red cells to attain a final Hot of 6%. Cells were treated with different concentrations of SDA, described in the previous paragraph, and NK activity was assessed. As can be seen in Table 5, 1 mM of SDA reduced NK activity by over 90% with no detectable activities at any of the higher doses tested. Con A induced T cell proliferation of the same samples was also measured in parallel for comparison.

Effect of SDA On cells required for long term engraftment (stem cells)

When bone marrow was treated with SDA at concentrations of 1.5 mM or higher, myeloid recovery as estimated by a 14 day methylcellulose culture was around 0–20%. However, animals receiving marrow treated with these concentrations of SDA reconstituted promptly and became long term survivors. To assess the impact of SDA on cells required for long term reconstitution, we took advantage of the observation that BALB/c marrow, prepared carefully to avoid peripheral blood contamination, would reconstitute C3H mice in an allogeneic BMT with only mild and non-lethal GVHD. To estimate the minimum number of cells required for reconstitution, lethally irradiated C3H mice were given decreasing numbers of BALB/c maxrow cells and survivors were scored on day 60 (Table 6). Injection of $4 \times 10^5$ cells per mouse allowed 80–100% of animals to survive past day 60. However, only 40% of the mice receiving $10^5$ cells were reconstituted. SDA up to 1.75 mM did not affect the minimum number of BALb/c marrow cells (between $10^5$ and $4 \times 10^5$) required for engraftment, suggesting that the marrow progenitors necessary for reconstitution were spared from SDA treatment.

In this experiment we described the use of a novel ex vivo purging agent, spermine dialdehyde (SDA), for abrogating GVHD after histoincompatible transplantation. Long term survivors were observed in those groups which received marrow treated ex vivo for 10 minutes with 1.2–2.2 mM of SDA. Full chimerism was established in these survivors, displaying cellular origin predominantly of the donor strain on day 120 post transplantation.

In vitro assays showed that T cells and NK cells were more sensitive to SDA mediated suppression than myeloid cells (Tables 2 and 5). Marrow treated with 1.2 mM of SDA showed no detectable T cell proliferation upon Con A stimulation. NK activity of spleen cells treated with corresponding concentrations of SDA under the same conditions (10 minute incubation at 37° C. in the presence of 6% Hct) was also reduced to an almost non-measurable level at 1.0 mM. Mice receiving marrow treated with 1.2–2.2 mM of SDA ex vivo exhibited little GVHD and became long term survivors. Myeloid growth in vitro in these groups ranged from 0–20% of the control response. Lack of reconstitution however was observed only at around 2.4 mM suggesting long term engraftment could be achieved in groups whose myeloid component showed little or no growth in vitro, an observation that had been reported before in human clinical situations (31,32). The presence of a 5–8% Hct appeared to provide the optimal condition for purging. Presumably red cells might be playing a scavenger role, protecting myeloid cells from the toxic effect of SDA (see below).

It has been shown by several investigators that donor NK cells might be partly responsible for the development of GVHD in recipients (33,34). SDA treatment appeared to remove effectively both T cell and NK cell activities. Bone marrow samples with both activities purged, reconstituted lethally irradiated animals and prevented GVHD. Earlier studies performed using a similar combination (BALB/c-CBA) showed that irradiated recipients receiving anti-Thy 1.2 and complement treated marrow cells did not become long term survivors suggesting that non-T-cells might be involved in GVHD induction (24). Thus the removal of NK activity in addition to T cell depletion might be an important feature for the alleviation of GVHD. SDA, which is capable of inactivating both populations might be a potent ex vivo purging agent.

The surviving mice from the SDA treated groups also exhibited full chimefism at day 120 post transplantation. Unlike anti-Thy 1.2+C' treatment which prevented GVHD at the expense of donor cell engraftment (35) ex vivo treatment of BALB/c cells with SDA allowed fully allogeneic reconstitution without depressing the donor cell engraftment. The recipients exhibited predominantly donor type H-2 specificity at day 120.

By injecting a limiting number of maxrow cells to reconstitute the irradiated mice, we found that SDA at concentrations up to 1.75 mM did not appear to affect the early progenitor cells required for reconstitution. The minimum number of cells in the SDA treated group needed for long term engraftment was the same as the control group.

Our recent data with human bone marrow suggested that cells treated with SDA showed 1–2 log T cell depletion as estimated by a limiting dilution assay. Using limiting dilution assays, our data showed that the degree of log T cell depletion could be controlled by adjusting the concentrations of SDA used for ex vivo treatment. Since several clinical groups have demonstrated that controlled or partial depletion is better than complete T cell removal (19,21), it is suggested that the SDA treatment dose be adjusted in certain situations, to substantially reduce GVHD without provoking graft rejection or high relapse rate.

In this experiment, we described a novel ex vivo agent spermine dialdehyde, that could effectively suppress GVHD in a histoincompatible mouse model. The procedure which would involve only the treatment of bone marrow buff coat (which usually contains around 5–8% Hct) with this agent for 10–15 minutes is simpler than other purging methods utilizing monoclonal antibodies, density gradient or physical separation. For 1 liter of marrow, the total treatment time was about 2 hours.

TABLE 1

In vitro assay data of marrow cell mixture used in BMT

| Dose | Con-A Induced Proliferation* cpm | | Day 10 Myeloid Colony Count | |
|---|---|---|---|---|
| Vehicle Control | 29,314 | | 558 | |
| 0.1 mM | 28,769 | (98)+ | 572 | (103) |
| 0.3 mM | 0 | (0) | 85 | (15) |
| 0.6 mM | 0 | (0) | 0 | (0) |

*Proliferation is calculated as (cpm for the test sample) − (cpm background)

+% Control response is calculated as $\frac{\text{cpm for test sample} - \text{cpm background}}{\text{cpm for control sample} - \text{cpm background}} \times 100$

TABLE 2

Effect of red cells on SDA activity

| Group | Dose (mM) | Con-A-induced Proliferation Assay* | | Total Myeloid CFU Number | |
|---|---|---|---|---|---|
| Hct 1% | Control | 8037 | (100)+ | 255 | |
| | 0.1 | 7152 | (87) | 232 | (91)+ |
| | 0.2 | 3109 | (30) | 74 | (29) |

TABLE 2-continued

Effect of red cells on SDA activity

| Group | Dose (mM) | Con-A-induced Proliferation Assay* | | Total Myeloid CFU Number | |
|---|---|---|---|---|---|
| | 0.3 | 0 | (0) | 15 | (6) |
| | 0.4 | 0 | (0) | 0 | (0) |
| Hct 5% | Control | 18866 | (100) | 295 | |
| | 0.8 | 1355 | (8.3) | 109 | (37) |
| | 1.0 | 862 | (5) | 122 | (41) |
| | 1.2 | 0 | (0) | 57 | (19) |
| | 1.4 | 0 | (0) | 26 | (9) |
| | 1.6 | 0 | (0) | 24 | (8) |
| | 1.8 | 0 | (0) | 27 | (9) |
| | 2.0 | 0 | (0) | 4 | (1) |
| Hct 8% | Control | 10030 | | 245 | |
| | 1.0 | 565 | (6)° | 61 | (25) |
| | 1.4 | 172 | (2)° | 31 | (13) |
| | 1.6 | 0 | (0) | 33 | (13) |
| | 1.8 | 0 | (0)° | 29 | (12) |
| | 2.0 | 0 | (0) | 11 | (4) |
| | 2.4 | 0 | (0) | 2 | (1) |

*Proliferation (see Table 1 for detail).
Total myeloid CFU = total BFU-E, CFU-G/M and CFU-GEM colony number on Day 10.
+% Control response (see Table 1 for detail).
°Limiting dilution studies done in separate experiments showed that the frequency of T cells in control, 1.4 mM & 1.8 mM treated samples were 1/75, 1/1400 & 1/7000 respectively. Experiments have been repeated 3 times with reproducible results.

TABLE 3

Hematology profile day 28 post transplantation

| Dose (mM) | RBC ($10^6$/mm$^3$) | WBC ($10^3$/mm$^3$) | Hb (g/dl) |
|---|---|---|---|
| 1.5 | 10.1 ± 0.5 | 11.6 ± 3.8 | 14.5 ± 0.7 |
| 1.6 | 8.5 ± 2.2 | 8.4 ± 4.3 | 14.3 ± 0.6 |
| 1.8 | 9.0 ± 2.8 | 9.3 ± 2.6 | 14.7 ± 0.5 |
| 2.0 | 10.8 ± 0.9 | 9.7 ± 2.4 | 15.4 ± 0.2 |
| BALB/c Control | 10.5 ± 0.6 | 8.7 ± 1.0 | 15.0 ± 0.2 |

Number/group = 5

TABLE 4

H-2 specific cytotoxicity on PBMC of C3H survivors transplanted with BALB/c marrow

| SDA Dose (mM) | Viability (%) | Number/group |
|---|---|---|
| a) H-$2^d$ specific toxicity | | |
| 1.2 | 7.2 ± 1.4 | 3 |
| 1.3 | 6.0 ± 1.4 | 5 |
| 1.5 | 9.5 ± 3.3 | 5 |
| 1.6 | 12.5 ± 3.7 | 4 |
| 1.8 | 13.0 ± 2.8 | 4 |
| 2.0 | 7.0 ± 2.8 | 4 |
| 2.2 | 8.0 ± 1.8 | 3 |
| Normal BALB/c | 7.0 ± 1.5 | 5 |
| Normal C3H | 90 ± 1.8 | 5 |
| Complement Control | 93 ± 3.0 | 5 |
| b) H-$2^k$ specific toxicity | | |
| SDA treated survivors* | 93.8 ± 4.2 | 10 |
| Normal C3H | 5.6 ± 4.6 | 5 |
| Normal Balb/C | 92.6 ± 1.9 | 5 |

*10 surviving animals from varying doses of SDA treated groups were randomly chosen for H-$2^k$ typing.

TABLE 5

Effect of SDA on NK activity

| Concentration SDA (mM)$^a$ | % Lysis of YAC-1 at E:T ratio$^b$ | | | Con-A-induced Proliferation (c.p.m.)$^{a,c}$ |
|---|---|---|---|---|
| | 100:1 | 50:1 | 25:1 | |
| 0 | 25.5 ± 0.7 | 20.4 ± 2.1 | 13.3 ± 1.5 | 115,112 |
| 0.5 | 9.2 ± 0.4 | 8.0 ± 1.5 | 4.4 ± 1.2 | 33,534 |
| 1.0 | 1.8 ± 0.1 | 1.1 ± 0.6 | 1.0 ± 0 | 1,849 |
| 1.5 | 0 | 0 | 0 | 151 |
| 2.0 | 0 | 0 | 0 | 27 |
| 2.5 | 0 | 0 | 0 | 0 |

$^a$Spleen cells from BALB/c mice pretreated with poly I:C were treated with SDA for 10 minutes and assayed for ability to lyse YAC-1 target cells. Con A induced proliferation was also measured as described in Materials & Methods.
$^b$Mean SD of values for 3 separate experiments.
$^c$cpm of Con A samples - cpm of no Con A samples.

TABLE 6

Effect of SDA on long term engraftment (Balb/C → C3H)

| Treatment | Cell Number | | |
|---|---|---|---|
| | $10^{6*}$ | $4 \times 10$ | $10^5$ |
| Control | 5/5# | 4/5 | 2/5 |
| 1.3 mM | 5/5 | 4/5 | 3/5 |
| 1.75 mM | 5/5 | 5/5 | 3/5 |

*Cell viabilities of both SDA or control group were all over 80% after ex vivo treatment.
Number of animals that survived past day 60/total number per group.

References

1. MARTIN P J, HANSEN J A, STORB R, et al. Human marrow transplantation: an immunological perspective. Adv. Immunol. 1987, 40:379–438.
2. BEATTY P C, CLIFF R A, MICKELSON E M, et al. Effects of in vitro depletion of T cells in HLA-identical allogeneic marrow grafts. Blood 1985, 66: 664–672.
3. BORTIN M M, Gale R P, Rimm A A. Allogeneic bone marrow transplantation for 144 patients with severe aplastic anemia. JAMA 1981, 245: 1132–1139.
4. RINGDEN O, NILSSON B. Death by graft-versus host disease associated with HLA mismatch, high recipient age, low marrow cell dose, and splenectomy. Transplantation 1985, 40: 39–43.
5. LAZARYS H M, COCCIA P F, HERZIG R H, et at. Incidence of acute graft-versus-host disease with and without methotrexate prophylaxis in allogeneic bone marrow transplant patients. Blood 1984, 64:215–220.
6. EDITORIAL. Graft-versus-host disease after marrow transplantation. Lancet 1984, 1:491–492.
7. BROSS D S, TUTSCHKA P J, FARMER E R et al. Predictive factors for acute graft-versus-host disease in patients transplanted with HLA-identical bone marrow. Blood 1984, 63: 1265–1270.
8. VOSSEN J M, HEIDT P J, GUIOT H F L et al. Prevention of acute graft versus host disease in clinical bone marrow transplantation: Complete versus selective intestinal alecontamination. In: Recent Advances in Germfree Research. Sasaki S, Ozawa A, Hashimoto K (eds). Tokai University Press, Tokyo 1983, p 573.
9. STORB R, PRENTIVE R L, BUCKNER C D et at. Graft-versus-host disease and survival in patients with aplastic anemia treated by marrow graft from HLA-identical siblings. Beneficial effects of a protective environment. N Engl J Med 1983, 308:302–307.
10. WITHERSPPON R, DEEG H J, LUM L et al. Immunological recovery in human marrow graft recipients given cyclosporin or methotrexate for the prevention of graft vs host disease. Transplantation 1984, 37:456–461.

11. RAMSAY N K C, KERSEY J H. Conditioning of bone marrow recipients with cyclophosphamide and total lymphoid irradiation. In: Slavin S (ed): Ibid, 1984, p 167.
12. REISNER Y, KAPOOR N, KIRKPATRICK D. Transplantation for severe combined immunodeficiency with HLA-A,B,D,DR incompatible parenteral marrow cells fractionated by soybean agglutinin and sheep red blood cells. Blood 1983, 61:341–348.
13. CUNNINGHAM I, CASTRO-MALASPINA H, FLOMENBERG N. T cell depleted bone marrow transplant (BMT) for chronic myelogenous leukemia (CML). Blood 1988, 72(5):384a.
14. O'REILLY R J, COLLINS N H, KERNAN N et al. Transplantation of marrow-depleted T cells by soybean lectin agglutination and E-rosette depletion: major histocompatibility complex-related graft resistance in leukemic transplant patients. Transplant Proc 1985, 17:455–459.
15. KERNAN N A, FLOMENBERG N, DUPONT B et al. Graft rejection in recipients of T-cell-depleted HLA-nonidentical marrow transplants for leukemia. Transplantation 1987, 43: 842–847.
16. FILIPOVICH A H, VALLERA D A, YOULE R J et al. Ex vivo T cell depletion with immunotoxins in allogeneic bone marrow transplantation: The pilot clinical study for prevention of graft-versus-host disease. Transplant Proc 1986, 17:442–444.
17. MITSUYASU R T, CHAMPLIN R E, GALE R P et al. Treatment of donor bone marrow with monoclonal anti-T cell antibody and complement for the prevention of graft-versus-host disease. Ann Intern Med 1985, 105:20–26.
18. WAGER J E, DONNENBERG A D, NOGA S J et al. Lymphocyte depletion of donor bone marrow by counterflow centrifugal elutriation: Results of a Phase I clinical trial. Blood 1988, 72:1168–1176.
19. KERNAN N A, BORDIGNON C, HELLER G et al. Graft failure after T-cell-depleted human leukocyte antigen identical marrow transplants for leukemia: I. Analysis of risk factors and results of secondary transplants. Blood 1989, 74:2227–2236.
20. MARTIN P J, HANSEN J A, TOROK-STORB B et al. Graft failure in patients receiving T cell-depleted HLA-identical allogeneic marrow transplants. Bone Marrow Transplant. 1988, 3:445–456.
21. CHAMPLIN R, GAJEWSKI J, LEE K et al. Selective depletion of CD8 positive T lymphocytes and post transplant cyclosporine for prevention of GVHD following bone marrow transplantation
22. LAU C, STANOJEV D, VISCONTI V et al. Purification, characterization and structural elucidation of the active moiety of the previously called "Suppressor Activating Factor (SAF)". Cell Immunol 1990, 125(1):92–106.
23. GAUGAS J. M. Biogenic aliamines and polyamines in support and in inhibition of lymphocyte proliferation. In: Polyamines in Biomedical Research. Gaugas JM (ed.). Wiley J & Sons: Chichester, 1980, pp 474–362.
24. GORCZYNSKI R M, LAU C Y, ROBILLARD M: Graft-versus-host disease in murine bone marrow transplantation. II. Modulation of acute and chronic GVHD in mice receiving bone marrow allografts pretreated with immunosuppressive factor derived from a human T cell line. Immunology Letters 1985, 11:293–299.
25. ISCOVE N N, SIEBER F. Erythroid progenitors in mouse bone marrow detected by macroscopic colony formation in culture. Exp Hemat 1975, 3:32–43.
26. GALLICCHIO V S, MURPHY Jr M I. In vitro erythropoiesis. II Cytochemical enumeration of erythroid stem cells from normal mouse and human hematopoietic tissues. Exp Hemat 1979, 7:219–224.
27. ROZANS M K, SMITH B R, EMERSON S, CRIMMINS M, LAURENT G, REICHERT T, BURAKOFF S J, MILLER R A. Functional assessment of T cell depletion from bone marrow prior to therapeutic transplantation using limiting dilution culture methods. Transplantation 1986, 42:380–387.
28. VALLERA D A, SODERLING C C B, CARLSON G J, KERSEY J H. Bone marrow transplantation across major histocompatibility barriers in mice. Transplantation 1981, 3:218–222.
29. JONES R J, ZUEHLSDORF M, ROWLEY S D, HILTON J, SANTOS G W, SENSEN BRENNER L L, COLVIN O M. Variability in 4-hydroperoxycyclophosphamide activity during clinical purging for autologous bone marrow transplantation. Blood 1987, 70: 1490–1494.
30. FOSTER H L, SMALL J D, FOX J G. The Mouse in Biomedical Research. Academic Press, 1983, Vol III, p 302.
31. YEAGER A M, KEIZER H, SANTOS G W, SARAL R et al. Autologous bone marrow transplantation in patients with acute nonlymphocytic leukemia, using ex vivo marrow treatment with 4-hydroperoxy- cyclophosphamide. New England J Med 1986, 315: 141–147.
32. CIOBANU N, PAIETFA E, ANDREEFF M, et at. Etoposide as an in vitro purging agent for the treatment of acute leukemias and lymphomas in conjunction with autologous bone marrow transplantation. Exp Hematol 1986, 14: 623–635.
33. MURPHY W J, KUMAR V, BENNETT M. Acute rejection of murine bone marrow allografts by NK cells and T cells: differences in kinetics and target antigens recognized. J Exp Med 1987, 166:1499–1507.
34. GHAYUR T, SEEMAYER T A, LAPP W S. Prevention of murine graft-versus-host disease by inducing and eliminating ASGM1 cells of donor origin. Transplantation 1988, 45:586–590.
35. VALLERA D A, CARROLL S F, BLAZAR B R. Experimental approaches for GVHD therapy and rejection in the mouse. J Cell Blochem 1990, Suppl. 14A:258 (abstract no. C 018).
36. HELANDER A, TOTTMAR O. Cellular distribution and properties of human blood aldehyde dehydrogenase. Alcoholism: Clin Exp Res 1986, 10:71–76.
37. KOHN F R, LANDKAMER G J, MANTHEY C L. Effect of aldehyde dehydrogenase inhibitors on the ex vivo sensitivity of human multipotent and committed hematopoietic progenitor cells and malignant blood cells to oxazaphosphorines. Cancer Res 1987, 47:3180–3185.

SDA ANIONIC/NON-ANIONIC BUFFER FORMULATIONS

Spermine Dialdehyde (SDA)

SDA was formulated from its diethyl acetyl bis nitrate salt as a sterile 20 mM (4 mg/ml) aqueous solution provided by The R. W. Johnson Pharmaceutical Research Institute (Raritan, N.J.). The drug was stored at −70° C., and allowed to equilibrate at room temperature prior to use.

Buffers used

The phosphate buffer saline used was Dulbecco's Phosphate-Buffered Saline from Gibco Laboratories [KCl (0.2 gm/L), $KH_2PO_4$ (0.2 gm/L), $MgCl_2$ anhyd. (0.047 gm/L), Nacl (8 gm/L) and $Na_2HPO_4$ (1.15 gm/L)]. Modified PBS was prepared according to a formula published by Low et al. (11) [$CaCl_2$ (0.1 m/L), KCl (0.2 gm/L), $MgCl_2 \cdot 6H_2O$ (0.1 gm/L), $KH_2PO_4$ (0.042 gm/L), $Na_2PO_4 \cdot 7H_2O$ (0.4 gm/L) and NaCl (8.6 gm/L)]. RPMI 1640 was purchased from Gibco Laboratories containing $Ca(NO_3)_2 \cdot 4H_2O$ (0.19 gm/L), KCl (0.4 gm/L), $MgSO_4$ (0.04 gm/L), NaCl (6 gm/L) and $Na_2HPO_4$ (0.8 gm/L).

Preparation of the Bis-2,4-Dinitropheylhydrazine Trifluoroacetate of SDA 2,4-Dinitrophenylhydrazine (27.7 mmol) was added to 50 ml of concentrated sulfuric acid, followed by the addition of 250 ml of ethanol followed and 150 ml of water. With stirring, SDA bis diethyl acetal bis nitrate (2.2 g, 4.6 mmol) was added to obtain a homogeneous solution. To ensure complete reaction, the mixture was stirred overnight. The yellow precipitate formed was filtered and washed with water followed by absolute ethanol and dry ether. The solid was converted into the free base form by dissolving it in a mixture consisting of 60 g of potassium carbonate dissolved in 400 ml of water and 700 ml of dichloromethane. The trifluoroacetate salt was formed by adding the solution dropwise to 200 ml of dichloromethane containing 3 ml of trifluoroacetic acid. After 2 hr stirring, the yellow precipitate was collected. NMR showed the final product to be more than 98% pure.

High Performance Liquid Chromatography (HPLC) Assay

Since SDA did not show measurable absorbance at wavelengths from 210–500 nm, a HPLC assay for the 2,4-dinitrophenylhydrazine (DNP) derivative of SDA was developed. Briefly, 1.6 ml of the derivation solution (359 mg of DNP dissolved in 90 ml DMSO, 10 ml $H_2O$ and 0.5 ml of 2N HCL) was mixed with 160 μl of 20 mM SDA and 80 μl of normal saline. The mixture was allowed to stand at room temperature for 60 min. For analysis by HPLC, 80 μl of the mixture was transferred to an autosample vial containing 1.5 ml of DMSO::ACN:$H_2O$ (64%: 11%:25%). After mixing, samples were sitting for 3 hr before being loaded onto a reverse phase ODS column. Absorbance at 360 nm was measured using a UV monitor. A bis-dinitrophenylhydrazine trifluoroacetate derivative of SDA, SDA(DNP)$_2$[$CF_3COO^-$]$_2$ synthesized as an internal standard was included in every run for quantitation. The molar concentrations of SDA in different preparations were calculated by comparing their peak areas to that of the internal standard. The lowest limit of detection was 14 ng of SDA loaded onto the column.

Acrolein Assay

The release of acrolein from SDA was monitored in a Gilford Model 2400 automatic recording spectrophotometer equipped with a Haake constant temperature circulator to maintain a reaction temperature of 37° C. The reaction mixture routinely contained 1 mM SDA. Buffers tested included phosphate buffer, modified phosphate buffer, normal saline (0.9% NaCl) and bicarbonate. Reaction mixtures were sealed in 1 cm quartz cuvettes and monitored at 210 nm. Authentic acrolein was used as the standard.

Animals and Husbandry

Male $CDF_1$ (Charles River, Canada) and male DBA mice (Jackson Laboratories), 7 to 10 weeks of age, were used in all experiments. Animals in transplant experiments were housed in sterile microisolator cages and fed acidified water and sterilized Lab Chow (Purina Mills Inc.) ad libitum.

Bone Marrow and Spleen Cella

Donor animals were sacrificed by cervical dislocation. Bone marrow cells were flushed from femurs and tibia with RPMI 1640 (Gibco) using a tuberculin syringe fitted with a 25 gauge needle. Single cell suspensions of spleen cells were made by forcing the spleens through a fine wire mesh. All cells were resuspended in enriched RPMI 1640 and washed twice with PBS or saline prior to drug treatment. Viability was assessed by a Trypan blue exclusion assay.

Ex vivo Incubation with SDA

Murine bone marrow cells, tumor cells in early log phase, bone marrow spleen cell mixtures (4:1), or bone marrow tumor cell mixtures were incubated at $2 \times 10^7$ cells/ml in either PBS or saline with varying concentrations of SDA for 10 min or 30 min at 37° C. in a moderately shaking water bath. PBS or saline was used as vehicle in all untreated controls. Incubation was stopped by adding cold medium. The cells were centrifuged at 850 g for 10 rain and then washed twice more before infusion and/or in vitro assay.

In vitro Assays

Murine myeloid progenitor cell assays were performed according to the modified method of Iscove & Sieber (15), to assess the toxicity of SDA on erythroid and myeloid precursors. After SDA treatment, $10^5$ bone marrow cells were plated in 35 mm suspension culture dishes (Lux) in murine hematopoietic media containing 0.9% methylcellulose CFerry Fox Laboratories, Vancouver). Duplicate cultures were incubated at 37° C. in a humidified atmosphere with 5% $CO_2$ in air. Colonies were scored on day 10 for BFU-E, CFU-G/M and CFU-GEM.

The tumor cell proliferation following SDA treatment in saline was determined by $^3$H-thymidine uptake. Briefly, $2 \times 10^4$ tumor cells were plated in triplicate microtitre wells in growth medium supplemented with 10% FCS. After 2 days, 0.4 μCi $^3$H-thymidine was added to each well. Cells were harvested 8 hr later, and radioactivity measured in a liquid scintillation counter (Beckman). Percent survival of control response was calculated as:

$$\% \text{ Survival} = \frac{\text{SDA-treated cultures (CPM)}}{\text{untreated control cultures (CPM)}}$$

and used to generate dose-response curves. Each data point represents the mean % survival±SD of 2-3 separate experiments.

T-cell response of drug treated bone marrow spleen cell mixtures in PBS was determined by the Concanavalin A (Con A) stimulated proliferation assay as previously described (3).

Syngeneic Transplant Experiments

After ex vivo treatment, the tumor bone marrow mixtures were adjusted to $3 \times 10^6$ nucleated cells/ml in RPMI-1640 and 1 ml volumes were infused intravenously into lethally irradiated (9.5 Gy) syngeneic recipients. Each $CDF_1$ mouse received mixtures containing $3 \times 10^4$ L1210 leukemia cells (1% of total cell mixture). DBA mice on the other hand were inoculated with syngeneic marrow mixed with 300 P815 mastocytoma cells per mouse (0.3% of total cell mixture). After transplantation, the animals were observed daily for event-free survival up to 60 days. Autopsies were performed at the time of death to determine the degree of tumor infiltration.

RESULTS

HPLC Quantitation of SDA Preparations

SDA was labelled with dinitrophenylhydrazine (DNP) as described above and loaded onto the reverse phase ODS column. Freshly labelled SDA eluted as a sharp peak at 4.35 min. The internal standard, synthesized $SDA(DNP)_2[CF_3COO^-]_2$ also eluted at 4.35 min, the same time as freshly labelled SDA. The molar concentration of SDA in the peak was calculated using the internal standard as a reference. When stored at $-70°$ C., SDA was stable for up to 5 months, after which time, it deteriorated at a rate of about 5% per month. All SDA preparations were used within 3 months of synthesis.

Stability of SDA in Different Buffers

SDA was incubated in the presence of different buffers as indicated in FIG. 11. At various times after incubation, the reaction was stopped by cooling and the incubation mixtures were then labeled with DNP before loading onto a reverse phase ODS column. The amount of SDA left in the preparations after incubation was measured by calculating respective peak areas and comparing to that of the internal standard (FIG. 11). Incubation of SDA in normal saline at 37° C. for up to 60 min did not decrease the amount of SDA in the preparation. However when buffers containing anionic salts such as phosphates and bicarbonates were used, SDA disappeared from the incubation mixture in a time related manner. Of the 4 buffers tested, SDA appeared to be most unstable in RPMI 1640 which contained both phosphates and bicarbonates. SDA also degraded faster in PBS than in modified PBS which contained about half as much phosphate ion as PBS.

Longer term stability of SDA, as monitored by the HPLC assay (data not shown) indicated that the disappearance of SDA followed general base catalysis. The catalytic activity varied directly with pH, ionic strength, temperature and concentration of the base. The most favorable pH for SDA was 2-4. The half-life of SDA at 20° C. was 60 days at pH 4. This was reduced to 40 days when the pH was raised to 6-6.5. SDA also disappeared rapidly upon increasing the temperature. The half-life decreased from 60 days at 4° C. to 12 hr when the temperature was raised to 40° C. SDA was found to be most stable when maintained in normal saline at pH 4-4.5 and stored at $-70°$ C. Preparations stored at that temperature maintained full potency after 5 months of storage (data not shown).

Detection of Acrolein Released from the Incubation Mixture

It has been demonstrated by Kimes et al. (16) that, at low concentrations, decomposition of the oxidized polyamines followed apparent first order kinetics through $\beta$-elimination to give rise to acrolein. Following the method published by Low et al. (11) in which they measured the release of acrolein from 4HC, we could not detect the release of acrolein from either dilute (0.1 mM, data not shown) or concentrated solutions of SDA (1 mM, FIG. 12) incubated in phosphate or bicarbonate buffers at 37° C. for 60 min. Acrolein alone gave a good absorption spectrum at 210 mM (FIG. 12, Insert). However, solutions of SDA did turn yellow after incubation, suggesting that some chromophore had been generated upon heating.

Effect of SDA on Different Lymphoid Populations in Buffers with Different Ionic Strengths We have previously reported that in RPMI 1640 and PBS, SDA is a potent and irreversible inhibitor of murine T cell functions (5). However, SDA was myelotoxic at the concentrations used in the studies. Since the presence of increasing concentrations of red cells appeared to offer myeloid protection, an acceptable therapeutic window could be achieved at a hematocrit (Hct) of 5-7%. Under these conditions, SDA could inactivate T cells over a wide dose range without damaging all of the myeloid cells required for reconstitution of an irradiated recipient. Further investigation using HPLC analysis indicated that SDA was rapidly degraded upon incubation in PBS or RPMI 1640. Thus, degradation products of SDA might be partially responsible for T cell inhibition. On the other hand, no degradation of SDA occurred in normal saline at up to 60 min of incubation (FIG. 11).

To evaluate the activities of SDA and its breakdown products, we compared the effect of ex vivo incubation in PBS or normal saline buffers on the inhibition of T cell and myeloid function. Con-A-induced T cell proliferation was inhibited 90% following incubation in PBS containing 2 mM SDA. In normal saline, however, T cell proliferation was relatively unaffected by 2 mM SDA, and maximal suppression was observed only at 4-5 mM SDA. Myeloid cells were more resistant than T cells to the inhibition of proliferation induced by SDA in PBS. In contrast, dose dependent myeloid growth inhibition by SDA in normal saline was very similar to the profile of T cells treated with SDA in the same buffer. After 30 min of incubation, 50% suppression of growth was found for each population at around 3.5 mM (FIG. 13). Thus, in the presence of normal saline, the differential effect of SDA on T cells and myeloid cells was not observed and SDA was less myelotoxic in saline than in PBS.

Effect of SDA on Murine Leukemic Cell Lines in the Presence of Normal Saline It has been reported previously (17-19) that oxidized products of spermine are potent inhibitors of tumor growth. In our earlier studies, SDA was evaluated as an ex vivo purging agent for autologous BMT in PBS or RPMI 1640. We found that at concentrations where SDA was inhibitory to tumor cells, severe myelotoxicity was also observed (dam not shown). In light of our new data that SDA was much less myelotoxic in saline, we decided to assess the possibility of using SDA as an ex vivo purging agent to remove residual tumor cells in the bone marrow for autologous BMT. FIG. 14 shows the effect of SDA on the proliferation of 4 mouse tumor cell lines as compared to myeloid cell growth measured by methylcellulose cultures. YAC-1 lymphoma and P815 mastocytoma were most sensitive to SDA with over 2 log depletion at 1 mM. The L1210 leukemia and WEHI-164 fibrosarcomas were less susceptible to the inhibitory effect of SDA with a 2 log depletion around 4 mM. Myeloid cells were least affected with a 1 log depletion at 4 mM. This observation led us to further pursue saline SDA as an ex vivo purging agent in two murine autologous BMT models.

Ex vivo Effect of SDA in Autologous BMT

The two tumor models chosen were L1210 leukemic cells into syngeneic CDF1 mice and P815 mastocytoma cells into syngeneic DBA mice. We first performed dose response studies to determine the minimum lethal number of L1210 cells and P815 cells required.

FIG. 15 shows the mean number of days of survival after tumor cell injection plotted as a function of the number of L1210 or P815 cells injected into the animals. The minimum number of L1210 cells required for 100% lethality was 100. For P815 mastocytoma cells, a dose of 100 cells killed all the mice within 15 days and only 10 cells were required to kill 25% of the mice. To evaluate the tumor purging ability of SDA, in the L1210 model, we have used $3 \times 10^4$ cells per mouse. With the P815 model, because of the higher tumorigenicity of the line, we have chosen to inject 300 tumor cells per mouse.

Results of the survival studies are shown in FIGS. 16 and 17. The irradiation control group died within $10 \pm 2$ days in the case of CDF, mice and $11 \pm 1$ days for DBA mice. Reconstitution was observed in all control animals receiving syngeneic marrow grafts who went on to become long term survivors (>60 days). Tumor control animals inoculated with vehicle-treated tumor-marrow mixtures exhibited 100% morbidity by day 19 in $CDF_1$ mice and by day 17 in DBA animals. As can be seen from the survival curves, at 3-3.5 mM SDA, 80% of the mice became long term survivors. We have carried out these experiments with up to 10 mM SDA and found that all long-term survivors showed hemopoietic reconstitution (dam not shown). Although the results from the in vitro CFU assay indicated that no myeloid colonies could be detected at 5 mM (data not shown), mice treated with higher doses of SDA became long term survivors. This difference highlights the limitation of the CFU assay as a predicator of engraftment and subsequent myeloid reconstitution following autograft purging. Since it has been reported that as little as 30 stem cells could reconstitute a mouse (20), and assuming SDA spares the early multipotent progenitor cells, it is not surprising that mice survived even after receiving maxrow treated with high doses of SDA.

DISCUSSION

We have shown previously that synthetic SDA is a potent inhibitor of T cells and NK cell proliferation (5). Ten rain of incubation at 37° C. in the presence of RPMI 1640 could irreversibly inactivate T cells and NK cells as measured by Con A induced proliferation and cytolysis respectively. Lethally irradiated mice receiving SDA-treated allogeneic marrow survived as long term chimeras with no sign of GVHD.

The postulated mechanism of action mediated by SDA, as documented in literature, is both controversial and confusing. Alarcon et al. (9) suggested that acrolein was the major breakdown product of oxidized sperminc formed from the oxidation of sperminc by fetal calf serum. Kimes et al. (16), employing ion exchange chromatography and TLC, found sperminc monoaldehyde, acrolein and some unidentified products (possibly a polymerized form of oxidized spermine formed upon condensation) to be breakdown products upon decomposition of SDA. The amount of acrolein obtained however was not stoichiometric since the total acrolein released was only 30-40% of the predicted value. Israel et al. (10) failed to detect the release of any acrolein from synthetic SDA when subjected to similar treatments (incubation at 37° C. in the presence of fetal calf serum). Using a sensitive HPLC assay to monitor the presence of SDA, we found SDA to be an unstable compound especially in the presence of weak anionic bases such as phosphates or bicarbonates. SDA was highly unstable in growth medium such as RPMI 1640 which contains both phosphates and carbonates (see Materials and Methods). Similar to Israel et al. (10), we failed to detect the release of any acrolein from the degrading SDA. Since we synthesized our SDA according to the method of Israel et al. (10), it is possible that synthetic SDA might not dissociate to acrolein, but might instead polymerize to a high molecular weight product upon incubation due to the higher molar concentration of SDA present in the solution. The color observed upon decomposition (from colorless to yellow) suggests the formation of a complex chromophore.

We also have supporting evidence from our previous studies that the major breakdown product of SDA was probably not acrolein. We found SDA, like other aldehydes such as benzyl aldehyde, to be a good substrate for aldehyde dehydrogenase when tested in phosphate buffer at 37° C. (21). Acrolein, on the other hand, strongly inhibited the activity of aldehyde dehydrogenase. Since these assay conditions promote the decomposition of SDA, release of acrolein from SDA should result in the inhibition of enzyme activity which was not observed. Attempts made to further characterize the breakdown products responsible for immunosuppressive activities using radioactive SDA were not successful. Counts associated with the decomposed product eluted in the void volume of the HPLC column which might represent a polymerized form of SDA or aggregates of the breakdown products.

In the presence of saline, SDA remained intact after 60 min of incubation. Intact SDA mediated inhibitory profiles which were very different from SDA decomposing in artionic buffers. Proliferating T lymphocytes were resistant to intact SDA while tumorigenic lymphoid cells were sensitive. Moreover, SDA concentrations that suppressed myeloid cell growth by 60-70% arrested 99% of tumor cell growth. This differential growth inhibition in vitro was also reflected in vivo as lethally irradiated mice receiving bone marrow tumor mixture treated with SDA in saline became long term survivors. More than a 2 log depletion of L1210 tumorigenicity was achieved after ex vivo treatment with SDA. With the P815 model, due to the highly lethal nature of the tumor, experiments could be set up to detect only a 30 fold reduction of tumorigenicity. Thus, SDA acted as an efficient purging agent for both models, greatly reducing the number of tumors and generating long-term survivors.

Most other tumor purging agents are also toxic to T cells in bone marrow (22,23). The fact that SDA in saline did not inhibit T cells suggests that mature T cells that are playing an important immunosurveillance role against tumor cells might be spared by SDA treatment. The lack of an inhibitory effect of SDA on T cells might account for its relatively wide therapeutic window for autologous transplantation (3.5 mM to >10 mM).

SDA shows significant anti-tumor activity in vitro at doses which are not myelotoxic. Long term bone marrow culture of human myeloid precursors have been initiated (data not shown) and at the inhibitory dose for most tumor cell lines, the yield of CFU-G/M recovered was equal to, or greater than, untreated control marrow by week 8. The results from our murine models suggest that SDA is an effective ex vivo purging modality to reduce minimal residual disease and preserve normal multipotent progenitor cells in autologous marrow grafts.

We have successfully demonstrated that synthetic SDA could act as a ex vivo purging agent for both allogeneic and autologous BMT in murine models. In the presence of anionic buffers, SDA was effective in inhibiting T cell activities while sparing enough stem cells to reconstitute an irradiated allogeneic animal. In contrast, the presence of a non-anionic buffer such as saline, SDA remained intact during the incubation period and was effective in removing contaminating tumor cells from a bone marrow tumor cell mixture. Our results suggest that the same SDA preparation could be used as an effective prod rug for both allogeneic and autologous BMT. The finding that two potent therapeutic effects reside in one compound is novel. When these findings are extended to human clinical situations, SDA represents an opportunity to enhance the chance of success for both types of transplantation.

REFERENCES

1. Lau, C. Y., Wang, E. Y., Li, D., Budz-Tymkewycz, S., Visconti, V., and Ishaque, A., *J. Immunol.* 134, 3155, 1985.
2. Lau, C. Y., Budz-Tymkewycz, S., Wang, E. Y., and Ishaque, A., *Cell. Immunol.* 87, 35, 1984.
3. Lau, C., Stanojev, D., Visconti, V., Pang, H., Krepinsky, G., Grey, A., Wang, E., and Ishaque, A., *Cell. Immunol.* 125, 92, 1990.
4. Gorczynski, R. M., Lau, C. Y., and Robillard, M., *Immunol. Letters* 11, 293, 1985.
5. Wang, E., Conant, I. M., Li, D., Visconti, V., Chourmouzis, E., and Lau, C. *Bone Marrow Transplant.* 6, 235, 1990.
6. Bachtach, U., Menashe, M., Faber, J., Desser, H., and Seiler, N. *Advances in Polyamine Research* 3, 259, 1981.
7. Gaugas, J. M., and Dewey, D. L., *Br. J. Cancer* 39, 548, 1979.
8. Bachrach, U., and Eilon, G., *Biochim. Biophys. Acta* 179, 494, 1969.
9. Alarcon, R. A., *Arch. Biochem. Biophys.* 137, 365, 1970.
10. Israel, M., Zoll, E. C., Muhammad, N., and Modest, E. I., *J. Med. Chem.* 16, 1, 1973.
11. Low, J. E., Borch, R. F., and Sladek, N. E., *Cancer Research* 42, 830, 1982.
12. Struck, R. F., *Cancer Research* 34, 2933, 1974.
13. Low, J. E., Borch, R. F., and Sladek, N. E., *Cancer Research* 43, 5815, 1983.
14. Borch, R. F., and Millard, J. A., *J. Med. Chem.* 30, 427, 1987.
15. Iscove, N. N., and Sicbet, F., *Erp. Hematol.* 3, 32, 1975.
16. Kimes, B. W., and Morris, D. R., *Biochim. Biophys. Acta* 228, 223, 1971.
17. Israel, M., Rosenfield, J. S., and Modest, E. J., *J. Med. Chem.* 7, 710, 1964.
18. Israel, M., Maddock, C. L., and Modest, E. J., Abstracts of Papers, 9th Int. Cancer Congress, Tokyo, Japan, 1966, p. 320.
19. Israel, M., and Modest, E. J., Abstracts of Papers, 10th Int. Cancer Congress, Houston, Texas, 1970, p. 682.
20. Spangrude, G. J., Heimfeld, S., and Weissman, I. L., *Science* 241, 58, 1988.
21. Kazmi, S. M. I., Koop, K., Li, D., Conant, J. and Lau, C., *Pharm. Research, in press.*
22. Jones, R. J., Colvin, O. M., and Sensenbrenner, L. L., *Cancer Research* 48, 3394, 1988.
23. Sladek, N. E., *Meth. & Find. In Exp. & CLin. Pharmacol.*, 9, 617, 1987.

What is claimed is:

1. A method for the selective suppression of at least one subpopulation of deleterious cells within a graft population of mammalian cells which comprises administering to said graft population of mammalian cells, in substantially pure form, a therapeutically effective amount of a compound having the formula:

to a mammal in need of such selective suppression for a period of time suitable to suppress phenomena deleterious to successful graft transplantation, without substantial suppression of other cells capable of facilitating engraftment.

2. The method of claim 1 wherein said deleterious phenomena comprise graft versus host disease.

3. The method of claim 1 wherein said deleterious phenomena comprise graft rejection.

4. The method of claim 1 wherein said deleterious phenomena comprise leukemic relapse.

5. The method of claim 1 wherein said other cells comprise cells suitable to mediate hematological reconstitution.

6. The method of claim 2 wherein said other cells further comprise those suitable to mediate hematological reconstitution.

7. The method of claim 5 wherein said other cells further comprise those suitable to mediate immunological reconstitution.

8. The method of claim 6 wherein said other cells further comprise those suitable to mediate immunological reconstitution.

9. The method of claim 2 wherein said deleterious cells axe mature, differentiated effector cells.

10. The method of claim 7 wherein said deleterious cells axe mature, differentiated effector cells.

11. The method of claim 10 wherein said effector cells comprise natural killer cells.

12. The method of claim 11 wherein said effector cells further comprise cytotoxic T lymphocytes.

13. The method of claim 1 wherein said deleterious cells axe cancerous cells.

14. The method of claim 13 wherein said cancerous cells axe tumor cells.

15. The method of claim 13 wherein said cancerous cells axe leukemic cells.

16. The method of claim 15 wherein said leukemic cells axe residual cells.

17. The method of claim 1 wherein said other cells axe red blood cells.

18. The method of claim 12 wherein said other cells axe red blood cells.

19. The method of claim 1 wherein said other cells comprise immature populations of cells capable of immunosurveillance, antileukemic responses, and successful engraftment.

20. The method of claim 18 wherein said other cells further comprise immature populations of cells capable of immunosurveillance, antileukemic responses, and successful engraftment.

21. The method of claim 19 wherein said other cells comprise early myeloid progenitor cells.

22. The method of claim 20 wherein said further other cells comprise early myeloid progenitor cells.

23. The method of claim 1 wherein said compound is 95%-97% pure, as measured by mass spectroanalysis.

24. The method of claim 23 wherein said compound is synthesized de nevo, using organic synthesis techniques.

25. The method of claim 2 wherein said compound is 95%-97% pure, as measured by mass spectroanalysis.

26. The method of claim 22 wherein said compound is 95%-97% pure, as measured by nuclear magnetic resonance.

27. The method of claim 26 wherein said compound is synthesized de novo using organic synthesis techniques.

28. The method of claim 1 wherein said transplantation is an allogeneic bone marrow transplantation.

29. The method of claim 28 wherein said compound is administered to said graff population of cells in a suitable physiologically compatible vehicle.

30. The method of claim 29 wherein said vehicle comprises an anionic buffer.

31. The method of claim 30 wherein said anionic buffer comprises a phosphate.

32. The method of claim 30 wherein said anionic buffer comprises a carbonate.

33. The method of claim 32 wherein said anionic buffer further comprises a phosphate.

34. The method of claim 33 wherein said anionic buffer is selected from the group consisting of RPMI 1640, α0 MEM, TRIS buffer, and serum.

35. The method of claim 34 wherein the concentration of said compound ranges from about 0.4 mm to about 2 mM.

36. The method of claim 35 wherein said administration to said graft population of cells takes place for about 10 minutes to about 30 minutes.

37. The method of claim 1 wherein said bone marrow transplantation is an autologous bone marrow transplantation.

38. The method of claim 37 wherein said compound is administered to said bone marrow population of cells in a suitable physiologically compatible vehicle.

39. The method of claim 38 wherein said vehicle comprises a non-anionic buffer.

40. The method of claim 39 wherein said buffer is saline.

41. The method of claim 40 wherein the concentration of said compound in saline is about 2mM to about 10 mM.

* * * * *

UNITED STATES PATENT AND TRADEMARK OFFICE
CERTIFICATE OF CORRECTION

PATENT NO. : 5,374,658
DATED : Dec. 20, 1994
INVENTOR(S) : Catherine Y. Lau

It is certified that error appears in the above-identified patent and that said Letters Patent is hereby corrected as shown below:

Column 50, claim 9, line 60  "axe" should be deleted and in its place should be "are"
Column 50, claim 10, line 62  "axe" should be deleted and in its place should be "are"
Column 50, claim 13, line 68  "axe" should be deleted and in its place should be "are"
Column 51, claim 14, line 2:  "axe" should be deleted and in its place should be "are"
Column 51, claim 15, line 4  "axe" should be deleted and in its place should be "are"
Column 51, claim 16, line 6  "axe" should be deleted and in its place should be "are"
Column 51, claim 24, line 28  "nevo" should be deleted and in its place should be "novo"
Column 52, claim 29, line 4  "graff" should be deleted and in its place should be "graft"
Column 52, claim 34, line 16  Greek character alpha is followed by "0"; the "0" should be deleted, leaving the Greek character alpha to stand alone
Column 52, claim 35, line 18  "0.4mm" should read "0.4 mM"

Signed and Sealed this

Eleventh Day of April, 1995

Attest:

BRUCE LEHMAN

*Attesting Officer*   *Commissioner of Patents and Trademarks*